United States Patent
Lois-Caballe et al.

(10) Patent No.: US 10,876,118 B2
(45) Date of Patent: *Dec. 29, 2020

(54) METHOD FOR EXPRESSION OF SMALL ANTIVIRAL RNA MOLECULES WITH REDUCED CYTOTOXICITY WITHIN A CELL

(71) Applicants: California Institute of Technology, Pasadena, CA (US); The Regents of the University of California, Oakland, CA (US)

(72) Inventors: Carlos Lois-Caballe, Cambridge, MA (US); David Baltimore, Pasadena, CA (US); Xiao-Feng Qin, Sugarland, TX (US); Irvin S. Y. Chen, Palos Verdes Estates, CA (US); Dong Sung An, Los Angeles, CA (US)

(73) Assignees: California Institute of Technology, Pasadena, CA (US); The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/028,262

(22) Filed: Jul. 5, 2018

(65) Prior Publication Data

US 2019/0002883 A1  Jan. 3, 2019

Related U.S. Application Data

(63) Continuation of application No. 15/395,348, filed on Dec. 30, 2016, now Pat. No. 10,041,072, which is a continuation of application No. 14/695,462, filed on Apr. 24, 2015, now Pat. No. 9,567,592, which is a continuation of application No. 13/749,319, filed on Jan. 24, 2013, now Pat. No. 9,034,577, which is a continuation of application No. 12/769,157, filed on Apr. 28, 2010, now Pat. No. 8,361,982, which is a continuation of application No. 11/683,962, filed on Mar. 8, 2007, now Pat. No. 7,737,124, which is a continuation-in-part of application No. 10/319,341, filed on Dec. 12, 2002, now Pat. No. 7,195,916, which is a continuation-in-part of application No. 10/243,553, filed on Sep. 13, 2002, now Pat. No. 7,919,309.

(60) Provisional application No. 60/347,782, filed on Jan. 9, 2002, provisional application No. 60/389,592, filed on Jun. 18, 2002, provisional application No. 60/406,436, filed on Aug. 27, 2002, provisional application No. 60/322,031, filed on Sep. 13, 2001.

(51) Int. Cl.
C12N 15/113 (2010.01)
C12N 15/11 (2006.01)
C12N 15/86 (2006.01)
C12N 15/63 (2006.01)
A61K 48/00 (2006.01)

(52) U.S. Cl.
CPC ........ *C12N 15/1132* (2013.01); *C12N 15/111* (2013.01); *C12N 15/113* (2013.01); *C12N 15/1138* (2013.01); *C12N 15/63* (2013.01); *C12N 15/86* (2013.01); *A61K 48/00* (2013.01); *C12N 2310/111* (2013.01); *C12N 2310/14* (2013.01); *C12N 2330/30* (2013.01); *C12N 2740/16043* (2013.01); *C12N 2740/16045* (2013.01); *C12N 2760/20122* (2013.01); *C12N 2799/027* (2013.01); *C12N 2810/609* (2013.01); *C12N 2830/003* (2013.01); *C12N 2830/008* (2013.01); *C12N 2830/48* (2013.01); *C12N 2840/203* (2013.01)

(58) Field of Classification Search
CPC . C12N 15/1132; C12N 15/631; C12N 15/111; C12N 15/113; C12N 2310/14; C12N 2740/16043; A61K 48/00
USPC ......... 435/6.1, 91.1, 91.31, 320.1, 455, 458; 514/55 A; 536/23.1, 24.3, 24.5
See application file for complete search history.

(56) References Cited

U.S. PATENT DOCUMENTS

| 5,258,289 A | 11/1993 | Davis et al. |
| 5,650,309 A | 7/1997 | Wong-Stall et al. |
| 5,859,310 A | 1/1999 | Bujard et al. |

(Continued)

FOREIGN PATENT DOCUMENTS

| WO | WO 2001/029059 | 4/2001 |
| WO | WO 2004/039957 | 5/2004 |

OTHER PUBLICATIONS

U.S. Appl. No. 15/944,562 (filed Apr. 3, 2018) (Year: 2018).*

(Continued)

*Primary Examiner* — Jane J Zara
(74) *Attorney, Agent, or Firm* — Knobbe, Martens, Olson & Bear, LLP

(57) ABSTRACT

In one aspect, the invention provides methods and compositions for the expression of small RNA molecules within a cell using a retroviral vector (FIG. 1A). Small interfering RNA (siRNA) can be expressed using the methods of the invention within a cell. In a further aspect, the invention provides methods for producing siRNA encoding lentivirus where the siRNA activity may interfere with the lentiviral life cycle. In yet a further aspect, the invention provides methods for expression of a small RNA molecule within a cell, such as an siRNA capable of downregulating CCR5, wherein expression of the small RNA molecule is relatively non-cytotoxic to the cell. The invention also includes small RNA molecules, such as an siRNA capable of downregulating CCR5, that are relatively non-cytotoxic to cells.

20 Claims, 27 Drawing Sheets

Specification includes a Sequence Listing.

(56) References Cited

U.S. PATENT DOCUMENTS

| | | | |
|---|---|---|---|
| 5,883,081 A | 3/1999 | Kraus et al. | |
| 6,022,962 A | 2/2000 | Chowrira et al. | |
| 6,060,317 A | 5/2000 | Malech | |
| 6,074,836 A | 6/2000 | Bordignon et al. | |
| 6,096,538 A | 8/2000 | Kingsman et al. | |
| 6,100,087 A | 8/2000 | Rossi et al. | |
| 6,218,186 B1 | 4/2001 | Choi et al. | |
| 6,255,071 B1 | 7/2001 | Beach et al. | |
| 6,274,788 B1 | 8/2001 | Kumar et al. | |
| 6,312,956 B1 | 11/2001 | Lane | |
| 6,482,618 B2 | 11/2002 | Mueller et al. | |
| 6,506,559 B1 | 1/2003 | Fire et al. | |
| 6,566,083 B1 | 5/2003 | Thastrup | |
| 6,586,208 B2 | 7/2003 | Donahue | |
| 6,635,472 B1 | 10/2003 | Lauermann | |
| 6,664,107 B1 | 12/2003 | Mak et al. | |
| 7,195,916 B2 | 3/2007 | Qin et al. | |
| 7,732,193 B2 * | 6/2010 | Lois-Caballe | C12N 15/867 435/320.1 |
| 7,732,207 B2 | 6/2010 | Qin et al. | |
| 7,737,124 B2 * | 6/2010 | Lois-Caballe | C12N 15/63 514/44 R |
| 7,919,309 B2 * | 4/2011 | Lois-Caballe | C12N 15/1132 435/320.1 |
| 8,361,787 B2 | 1/2013 | Lois-Caballe et al. | |
| 8,361,982 B2 | 1/2013 | Lois-Caballe et al. | |
| 8,969,076 B2 * | 3/2015 | Lois-Caballe | C12N 7/00 435/320.1 |
| 9,034,577 B2 * | 5/2015 | Lois-Caballe | C12N 15/63 435/6.1 |
| 9,551,011 B2 * | 1/2017 | Lois-Caballe | A61P 31/12 |
| 9,567,592 B2 | 2/2017 | Lois-Caballe et al. | |
| 9,963,717 B2 | 5/2018 | Lois-Caballe et al. | |
| 10,041,072 B2 * | 8/2018 | Lois-Caballe | C12N 15/86 |
| 2003/0059944 A1 | 3/2003 | Lois-Caballe et al. | |
| 2003/0084471 A1 | 5/2003 | Beach et al. | |
| 2003/0124513 A1 | 7/2003 | McSwiggen | |
| 2003/0143204 A1 | 7/2003 | Lewis et al. | |
| 2003/0219823 A1 | 11/2003 | Alsobrook et al. | |
| 2004/0072771 A1 | 4/2004 | Symonds et al. | |
| 2005/0221354 A1 | 10/2005 | Mounts | |
| 2010/0267146 A1 | 10/2010 | Lois-Caballe et al. | |
| 2015/0218564 A1 | 4/2015 | Lois-Caballe et al. | |

OTHER PUBLICATIONS

Canadian Office Action dated Jul. 10, 2014 for Canadian Patent Application No. 2,680,129.

"Mutant Gene Produces Strong Natural Resistance to HIV-1 Infection in 1 in 100 People", University of Pennsylvania Health System, News and Periodicals, Aug. 8, 1996, pp. 1-3.

"Pushing the Envelope" Howard Hughes Medical Institute (HHMI) News, Nov. 21, 1997, pp. 1-2.

"Scientists suggest new approaches for development of AIDS drugs and vaccines" National Cancer Institute, Charity Wire, Article 01853, Jun. 21, 1999, pp. 1-3.

An et al., "Optimization and functional effects of stable short hairpin RNA expression in primary human lymphocytes via lentiviral vectors," Mol. Ther. 14:494-504 (2006).

Arendt et al., "Vector Systems for the Delivery of Small Interfering RNAs: Managing the RISC" ChemBioChem 2003, 4, pp. 1129-1136.

Baltimore, "Gene therapy. Intracellular immunization," Nature 335:395-396 (1988).

Banerjea et al., "Inhibition of HIV-1 by lentiviral vector-transduced siRNAs in T lymphocytes differentiated in SCID-hu mice and CD34+ progenitor cell-derived macrophages", Molecular Therapy : The Journal of American Society of Gene Therapy, Jul. 2003, vol. 8, No. 1, pp. 62-71.

Barton et al., "Retroviral delivery of small interfering RNA into primary cells", PNAS, Nov. 12, 2002, vol. 99, No. 23, pp. 14943-14945.

Brummelkamp et al., "A system for stable expression of short interfering RNAs in mammalian cells." Apr. 19, 2002, vol. 296, pp. 550-553.

Caplen et al., Specific inhibition of gene expression by small double-stranded RNAs in invertebrate and vertebrate systems, PNAS, Aug. 14, 2001, vol. 98, pp. 9742-9747.

Carmell et al., "The Argonaute family: tentacles that reach into RNAi, developmental control, stem cell maintenance, and tumorigenesis," Genes & Development, 2002, pp. 2733-2742.

Chatterjee et al. "Dual-target inhibition of HIV-1 in virto by means of an adeno-associated antisense vector." Science, Nov. 27, 1992, vol. 258, pp. 1485-1488.

Consiglio et al., "In vivo gene therapy of metachromatic leukodystrophy by lentiviral vectors: correction of neuropathology and protection against learning impairments in affected mice", Nature Medicine, Mar. 2001, vol. 7, No. 3, pp. 310-316.

Czauderna et al., "Inducible shRNA expression for application in a prostate cancer mouse model", Nucleic Acids Research, Nov. 1, 2003, vol. 31, No. 21, p. e127.

De Palma et al., "In Vivo Targeting of Tumor Endothelial Cells by Systemic Delivery of Lentiviral Vectors", Human Gene Therapy, Aug. 10, 2003, vol. 14, pp. 1193-1206.

Devroe E. & Silver P A, "Retrovirus-delivered siRNA", BMC Technology, Aug. 28, 2002, pp. 1-5.

Filipowicz et al., "Post-translational gene silencing by siRNAs and miRNAs," Structural Biology, pp. 331-341 (2005).

Fire et al., "Potent and specific genetic interference by double-stranded RNA in Caenorhabditis elegans," Nature, 391:806-811 (1998).

Fish and Kruithof, "Short-term cytotoxic effects and long-term instability of RNAi delivered using lentiviral vectors," BMC. Mol. Biol. 5:9 (2004).

Gatlin et al., "Long-term engraftment of nonobese diabetic/severe combined immunodeficient mice with human CD34+ cells transduced by a self-inactivating human immunodeficiency virus type I vector. Human Gene Therapy." vol. 12, pp. 1079-1089 (2001).

Godwin et al., "Detection of targeted GFP-Hox gene fusions during mouse embryogenisis." PNAS, vol. 95, pp. 13042-10347 (1998).

Grimm et al., "Fatality in mice due to oversaturation of cellular microRNA/short hairpin RNA pathways," Nature, 441:537-541 (2006).

Ilves et al, "Retroviral Vectors designed for targeted expression of RNA polymerases III-driven transcripts: a comparative study," Gene, vol. 171, pp. 203-208 (1996).

Iwakuma et al., "Self-inactivating Lentiviral Vectors with U3 and U5 Modifications," Virology, vol. 261, pp. 120-132 (1999).

Jackson et al., "Widespread siRNA "off-target" transcript silencing mediated by seed region sequence complementarity," RNA. 12:1179-1187 (2006).

Jacque et al., "Modulation of HIV-1 replication by RNA interference," Nature, vol. 418, pp. 435-438 (2002).

Junker et al., "Reduction in replication of the human immunodeficiency virus type I in human T cell lines by polymerase III-driven transcription of chimeric tRNA-antisense RNA genes," Antisense Research and Development, vol. 4, pp. 165-172 (1994).

Kafri et al., Lentiviral Vectors: Regulated gene expression. Molecular Therapy, vol. 1, No. 6, pp. 516-521 (2000).

Lawrence, RNAi could hold promise in the treatment of HIV, The Lancet, vol. 359, p. 207 (2002).

Lee N S et al., "Expression of small interfering RNAs targeted against HIV-1 rev transcripts in human cells", Nature Biotechnology, vol. 19, pp. 500-505 (2002).

Li et al., "Inhibition of HIV-1 infection by lentiviral vectors expressing pol III-promoted anti-HIV RNAs", Molecular Therapy, Academic Press, Aug. 2003, vol. 8, No. 2, pp. 196-206.

Lieberman et al., "Interfering with disease: opportunities and roadblocks to harnessing RNA interference," Trends in Molecular Medicine, Sep. 2003, vol. 9, No. 9, pp. 397-403.

Lois Carlos et al., "Germline transmission and tissue-specific expression of transgenes delivered by lentiviral vectors", Science, Feb. 1, 2002, vol. 295, No. 5556, pp. 868-872.

Martinez, L.J., "Katy, bar the door! HIV entry inhibitors", Research Initiative/Treatment Action Article, Jun. 2000, 6(2):6-12.

(56) References Cited

OTHER PUBLICATIONS

Matsukura et al., "Establishment of conditional vectors for hairpin siRNA knockdowns", Nucleic Acids Research, Aug. 1, 2003, vol. 31, No. 15, pp. e77 (1-5).
Miyagishi et al., "U6 promoter-driven sirnas with four uridine 3' overhangs efficiently suppress targeted gene expression in mammalian cells", Nature Biotechnology, May 2002, vol. 19, No. 5, pp. 497-500.
Miyoshi et al., "Stable and efficient gene transfer into the retina using an HIV-based lentiviral vector", Medical Sciences, Sep. 1997, vol. 94, pp. 10319-10323.
Miyoshi et al. "Development of a self-inactivating lentivirus vector", Journal of Virology, 1998, pp. 8150-8157, vol. 72, No. 10.
Mummidi et al., "The human CC chemokine Receptor 5 (CCR5) gene" Jour. Biol. Chem., Dec. 5, 1997, vol. 272, p. 30662.
Naldini L. et al., "In Vivo Gene Delivery and Stable Transduction of Nondividing Cells by a Lentiviral Vector," Science, Apr. 12, 1996, vol. 272, pp. 263-267.
Novina et al., siRNA-directed inhibition of HIV-1 infection, Nature Medicine, vol. 8, pp. 681-686 (2002).
Ogueta et al., Design and in vitro characterization of a single regulatory module for efficient control of gene expression in both plasmid DNA and a self-inactivating lentiviral vector. Molecular Medicine, vol. 7, No. 8. pp. 569-579 (2001).
Ohkawa et al., "Control of the functional activity of an antisense RNA by a tetracycline-responsive derivative of the human U6 snRNA promoter", Human Gene Therapy, vol. 11, No. 4, pp. 577-585 (2000).
Paddison et al., Short hairpin RNAs (shRNAs) induce sequence-specific silencing in mammalian cells, Genes & Development, pp. 948-958, 2002.
Paul et al., "Effective expression of small interfering RNA in human cells", Nature Biotechnology, vol. 20, No. 5, pp. 505-508 (2002).
Qin et al., "Inhibiting HIV-1 infection in human T cells by lentiviral-mediated delivery of small interfering RNA against CCR5", Proceeding of the National Academy of Sciences of USA, vol. 100, No. 1, pp. 183-188 (2003).
Reiser et al., "Development of Multigene and Regulated Lentivirus Vectors," Journal Virol. vol. 74, No. 22, pp. 10589-10599 (2000).
Rocheleau et al. "Wnt signaling and an APC-related gene specify endoderm in early C. elegans embryos," Cell, 90:707-716 (1997).
Roger J. Pomerantz, RNA interference meets HIV-1: Will silence be golden? Nature Medicine, vol. 8, pp. 659-660 (2002).
Shankar, Premlata, "RNAi-Mediated Inhibition of HIV-1 Replication in Primary Macrophages", Biosino Genome, Presentation, pp. 1-28 (2003).
Shirane et al., "Enzymatic production of RNAi libraries from cDNAs," Nat. Genet. 36:190-196 (2004).
Sirven et al., "The human immunodeficiency virus type-1 central DNA flap is a crucial determinant for lentiviral vector nuclear import and gene transduction of human hematopoietic stem cells", W.B. Saunders Company, Dec. 15, 2000, pp. 4103-4110, vol. 96, No. 13, Orlando, Florida.
Sui et al., A DNA vector-based RNAi technology to suppress gene expression in mammalian cells, PNAS, vol. 99, pp. 5515-5520 (2002).
Timmons et al., "Specific interference by ingested dsRNA." Nature, vol. 395, p. 854 (1998).
Van De Wetering Marc et al., "Specific inhibition of gene expression using a stably integrated, inducible small-interfering-RNA vector", EMBO Reports, vol. 4, No. 6, pp. 609-615 (2003).
Yang Shi, "Mammalian RNAi for the masses," Trends in Genetics, vol. 19, No. 1, pp. 9-12 (2003).
Yu Jenn-Yah et al., "RNA interference by expression of short-interfering RNAs and hairpin RNAs in mammalian cells", Proceeding of the National Academy of Sciences of USA, vol. 99, No. 9, pp. 6047-6052 (2002).
Zamore, "Ancient Pathways Programmed by Small RNAs," Science, 296 (5571):1265-1269 (2002).
Zennou et al., "HIV-1 Genome Nuclear Import is Mediated by a Central DNA Flap," Cell, vol. 101, pp. 173-185 (2000).
Zufferey et al., "Woodchuck hepatitis virus posttranscriptional regulatory element enhances expression of transgenes delivered by retroviral vectors", Journal of Virology, vol. 74, No. 4 pp. 2886-2892 (1999).
International Search Report dated Mar. 25, 2003 for International Application No. PCT/US02/29214, filed Sep. 13, 2002.
International Search Report dated Aug. 23, 2004 for International Application No. PCT/US2003/28732, filed Sep. 10, 2003.
International Search Report and Written Opinion dated Sep. 3, 2008 for International Application No. PCT/US2008/056245, filed Mar. 7, 2008.
An et al. "Stable reduction of CCR5 by RNAi through hematopoietic stem cell transplant in non-human primates", Proc. Natl. Acad. Sci. U S A., 104(32):13110-13115 (2007).
Anderson and Akkina, "CXCR4 and CCR5 shRNA transgenic CD34+ cell derived macrophages are functionally normal and resist HIV-1 infection", Retrovirology, 2:53 (2005).
Butticaz et al., "Protection from HIV-1 infection of primary CD4 T cells by CCR5 silencing is effective for the full spectrum of CCR5 expression", Antivir Ther., 8(5):373-377 (2003).
Lee et al., "Inhibition of human immunodeficiency virus type 1 replication in primary macrophages by using Tat- or CCR5-specific small interfering RNAs expressed from a lentivirus vector", J. Virol., 77(22):11964-11972 (2003).
Li et al., "Downregulation of CCR5 expression on cells by recombinant adenovirus containing antisense CCR5, a possible measure to prevent HIV-1 from entering target cells", J. Acquir. Immune Defic. Syndr., 43(5):516-522 (2006).
Sanders DA, "No false start for novel pseudotyped vectors", Curr. Opin. Biotechnol., 13(5):437-442 (2002).
Office Action dated Apr. 12, 2016 in U.S. Appl. No. 14/622,064.
Examination Report dated Sep. 11, 2015 in Canadian patent application No. 2680129.
Examination Report dated Dec. 21, 2015 in Canadian patent application No. 2867981.
Fierro, et al., "Hepatitis E virus: An Ancient hidden enemy in Latin America" World J. Gastroenterol., Feb. 21, 2016; 22(7):2271-2283.
Reshetnyak, et al., "Hepatitis G Virus" World J. Gastroenterol., Aug. 14, 2008; 14(30):4725-4734.
European Extended Search Report dated Jan. 19, 2017 in European Patent Application No. 16179414.4.
Agrawal et al., "Antisense therapeutics: is it as simple as complementary base recognition?" Molecular Med. Today, vol. 6, pp. 72-81, 2000.
Bjorklund et al., "Embryonic stem cells develop into functional dopaminergic neurons after transplantation in a Parkinson rat model," Proc. Natl. Acad. Sci., vol. 99, No. 4, pp. 2344-2349, 2002.
Branch, Trends in Biochem. Sci., "A good antisense molecule is hard to find," vol. 23, pp. 45-50, 1998.
Chirila et al., "The use of synthetic polymers for delivery of therapeutic antisense oligodeoxynucleotides," Biomaterials, vol. 23, pp. 321-342, 2002.
Crooke, Antisense Res. and Application, pp. 1-50 Ed. By S. Crooker, Springer-Verlat, Publ., 1998.
Hemmati-Brivanlou et al., "Vertebrate Embryonic Cells Will Become Nerve Cells Unless Told Otherwise," Cell, vol. 88, pp. 13-17, 1997.
Kawasaki et al., "Induction of Midbrain Dopaminergic Neurons from ES Cells by Stromal Cell—Derived Inducing Activity," Neuron, vol. 28, pp. 31-40, 2000.
Michienzi et al., "RNA-Mediated Inhibition of HIV in a Gene Therapy Setting," Ann. N. Y. Acad. Sci., 1002:63-71 (2003).
Odorico et al., "Multilineage differentiation from human embryonic stem cell lines," Stem Cells, vol. 19, pp. 193-204, 2001.
Peracchi et al. "Prospects for antiviral ribozymes and deoxyribozymes," Rev. Med. Virol, vol. 14, pp. 47-64, 2004.
Pomerantz, "RNA interference meets HIV-1: Will silence be golden?" Nature Medicine, vol. 8, p. 659-660, Jul. 2002.
Rubinson et al., "A lentivirus-based system to functionally silence genes in primary mammalian cells, stem cells, and transgenic mice by RNA interference," Nature Genetics, vol. 33, pp. 401-407 (Mar. 2003).

(56) References Cited

OTHER PUBLICATIONS

Examination Report dated Feb. 3, 2017 in Canadian patent application No. 2680129.
Office Action dated Jul. 17, 2017 in U.S. Appl. No. 15/391,189.
Office Action dated Nov. 17, 2017 in U.S. Appl. No. 15/391,189.
Office Action dated Dec. 11, 2017 and issued in Canadian Patent Application No. 2,952,590.

* cited by examiner

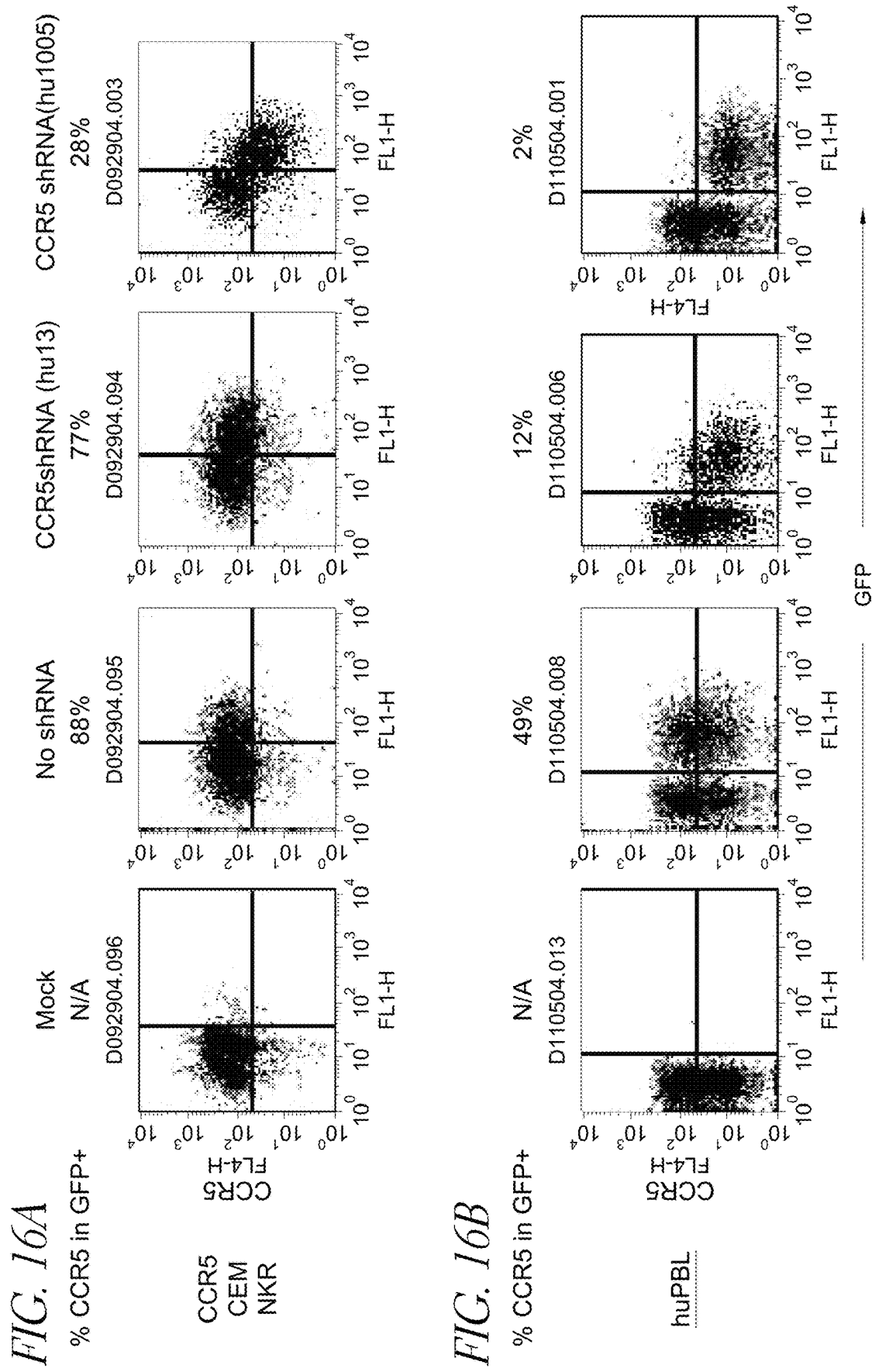

METHOD FOR EXPRESSION OF SMALL ANTIVIRAL RNA MOLECULES WITH REDUCED CYTOTOXICITY WITHIN A CELL

REFERENCE TO RELATED APPLICATIONS

The present application is a continuation of U.S. patent Ser. No. 15/395,348, filed on Dec. 30, 2016, which is a continuation of U.S. patent application Ser. No. 14/695,462, filed on Apr. 24, 2015, now U.S. Pat. No. 9,567,592, which is a continuation of U.S. patent application Ser. No. 13/749,319, filed on Jan. 24, 2013, now U.S. Pat. No. 9,034,577, which is in turn a continuation of U.S. patent application Ser. No. 12/769,157, now U.S. Pat. No. 8,361,982, filed on Apr. 28, 2010, which is in turn a continuation of U.S. patent application Ser. No. 11/683,962, now U.S. Pat. No. 7,737,124, filed on Mar. 8, 2007, which is in turn a continuation-in-part of U.S. application Ser. No. 10/319,341, now U.S. Pat. No. 7,195,916, filed on Dec. 12, 2002 which is in turn a continuation-in-part of U.S. application Ser. No. 10/243,553, now U.S. Pat. No. 7,919,309, filed on Sep. 13, 2002, which in turn claims priority under 35 U.S.C. § 119(e) from U.S. Provisional Application No. 60/322,031, filed on Sep. 13, 2001, U.S. Provisional Application No. 60/347,782, filed on Jan. 9, 2002, U.S. Provisional Application No. 60/389,592, filed on Jun. 18, 2002, and U.S. Provisional Application No. 60/406,436, filed on Aug. 27, 2002. All of the priority applications are hereby incorporated by reference in their entirety.

GOVERNMENT SUPPORT

This invention was made with government support under Grant Nos. GM039458, AI055281, and AI039975 awarded by the National Institutes of Health. The Government has certain rights in the invention.

BACKGROUND OF THE INVENTION

Field of the Invention

The present invention relates generally to methods for altering gene expression in a cell or animal using viral constructs engineered to deliver an RNA molecule, and more specifically to deliver double-stranded RNA molecules that can be used to down-regulate or modulate gene expression. Particular aspects of the invention relate to down-regulating a pathogenic virus gene or a gene necessary for a pathogenic virus life cycle through delivery of a viral construct engineered to express an RNA molecule. In some embodiments, the RNA molecule is not toxic to a target cell.

Description of the Related Art

RNA interference (RNAi) or silencing is a recently discovered phenomenon (A. Fire et al., Nature 391, 806 (1998); C. E. Rocheleau et al. Cell 90, 707 (1997)). Small interfering RNAs ("siRNAs") are double-stranded RNA molecules that inhibit the expression of a gene with which they share homology. siRNAs have been used as a tool to down regulate the expression of specific genes in a variety of cultured cells as well as in invertebrate animals. A number of such approaches have been reviewed recently (P. D. Zamore, Science 296, 1265 (2002)); however, such approaches have limitations. For example, no technique prior to the invention described herein allows for the generation of transgenic mammals having a specific gene down regulated through RNA interference. Similarly, there is a need for more robust methods for the introduction of small RNA molecules with regulatory function. The invention provided herein addresses these and other limitations in the field of RNA mediated gene regulation. Likewise, there is a need for improved methods and compositions for the treatment of viruses and diseases associated with viral infection.

Cytotoxicity and other adverse effects of small RNA molecules in target cells have been noted in the art and correlated with expression levels of the siRNA (D. S. An et al., Mol. Ther. 14, 494-504 (2006)). Utilizing weaker promoters to express the small RNA molecules has been shown to reduce apparent toxicities; however, the potency of the siRNAs was also attenuated.

Studies have reported adverse effects such as, for example, induction of interferon response genes (see R. J. Fish and E. K. Kruithof, B M C. Mol. Biol. 5, 9 (2004)), global change of mRNA expression profiles caused by off target effects (see A. L. Jackson et al., RNA. 12, 1179-1187 (2006)) and cytotoxic effects due to microRNA dysregulation (D. Grimm et al., Nature. 441, 537-541 (2006)). Cytotoxic effects have also been observed in in vitro cultured human T lymphocytes upon shRNA expression (D. S. An et al., Mol. Ther. 14, 494-504 (2006)). Any cytotoxic effects of siRNA could be particularly problematic in situations where siRNA expression is to be maintained in a living organism stably over long-term, for example, in order to achieve intra-cellular immunization against HIV-1 disease (D. Baltimore, Nature 335, 395-396 (1988)).

SUMMARY OF THE INVENTION

The invention relates generally to methods to express within a cell an RNA molecule or molecules. These methods can be used with a wide variety of cell types, and for a variety of purposes. For example, RNA molecules can serve as markers within a cell, can be antisense oligonucleotides or ribozymes for regulating gene expression, and can serve to down regulate genes through RNA interference.

In one aspect, methods are provided for the treatment or prevention of infection through the expression of one or more RNA molecules that inhibit one or more aspects of the life cycle of a pathogen through RNA interference with a target nucleic acid, such as a viral genome, a viral transcript or a host cell gene that is necessary for viral replication.

According to another aspect of the invention, a method of expressing an RNA molecule is provided which includes transfecting a packaging cell line with a retroviral construct and recovering recombinant retrovirus from the packaging cell line. A host cell is then infected with the recombinant retrovirus.

The recombinant retrovirus construct preferably has a first RNA polymerase III promoter region, at least one RNA coding region, and at least one termination sequence. The RNA coding region preferably comprises a sequence that is at least about 90% identical to a target sequence within the target nucleic acid. Preferably the target nucleic is necessary for the life cycle of a pathogen, for example, part of a pathogenic virus RNA genome or genome transcript, or part of a target cell gene involved in the life cycle of a pathogenic virus.

In one embodiment, the methods of the invention are used to disrupt the life cycle of a pathogen. In a particular embodiment the methods are used to disrupt the life cycle of a virus having an RNA genome, for example a retrovirus, by targeting the RNA genome directly. In another embodiment a viral genome transcript is targeted, including transcripts of individual viral genes. The methods also can be used to down regulate a gene in a host cell, where the gene is involved in the viral life cycle, for example, a receptor or co-receptor necessary for viral entry into the host cell.

In some embodiments, the RNA coding region encodes an siRNA, preferably a self-complementary "hairpin" RNA molecule having a sense region, an antisense region and a loop region. The loop region is generally between about 2 and about 15 nucleotides in length, and in a more preferred embodiment is about 6 to about 9 nucleotides in length. The double-stranded region of the hairpin molecule comprises a nucleotide sequence that is homologous to the target sequence. The sequence in the hairpin molecule is preferably at least about 90% identical to a target sequence, more preferably at least about 95% identical, even more preferably at least about 99% identical.

In other embodiments, the RNA coding region encodes a first RNA molecule, and the retroviral construct has a second RNA polymerase III promoter and a second RNA coding region operably linked to the second RNA polymerase III promoter. In such an embodiment, the second RNA coding region encodes an RNA molecule substantially complementary to the first RNA molecule. Upon expression of the first and second RNA coding regions, a double-stranded complex is formed within a cell.

In yet another embodiment, the retroviral construct can have a second RNA polymerase III promoter region operably linked to the RNA coding region, such that expression of the RNA coding region from the first RNA polymerase III promoter results in the synthesis of a first RNA molecule and expression of the RNA coding region from the second RNA polymerase III promoter results in synthesis of a second RNA molecule substantially complementary to the first RNA molecule. In one such embodiment, the RNA polymerase III promoters are separated from the RNA coding region by termination sequences.

In one embodiment of the invention, the target cell is an embryonic cell. An embryonic cell as used herein includes a single cell embryo, and embryo cells within an early-stage embryo. The target cell may be an embryogenic stem cell. When the target cell is an embryonic cell, the embryonic cell can be infected by injecting the recombinant retrovirus between the zona pellucida and the cell membrane of a mammalian embryonic cell. In another embodiment, the embryonic cell can be infected by removing the zona pellucida and incubating the cell in solution containing the recombinant retrovirus. In such an embodiment, the zona pellucida can be removed by enzymatic digestion. When the target cell is an embryonic cell or an embryogenic stem cell, the methods of the invention also include implanting the embryonic cell in a pseudopregnant female to generate a transgenic animal. In such a fashion, a transgenic animal can be generated that is resistant to a particular pathogen, such as a virus.

The methods of the invention can also be used with a variety of primary, ex vivo normal or diseased cells or cells adapted in various tissue culture conditions. The cells are preferably obtained from human, mouse or other vertebrates. The cells may include, without limitation, hematopoietic stem or precursor cells, central nerve system cells, cells with regenerative capacities for a variety of other tissues and organs, dendritic cells and other developing and mature myeloid and lymphoid cells, and cancer cells derived from different cell lineages.

In another aspect the invention provides retroviral constructs for the expression of an RNA molecule or molecules within a cell. The constructs preferably comprise an RNA polymerase III (pol III) promoter. In one embodiment the retroviral constructs have an RNA coding region operably linked to the RNA polymerase III promoter. The RNA coding region can be immediately followed by a pol III terminator sequence, which directs termination of RNA synthesis by pol III. The pol III terminator sequences generally have 4 or more consecutive thymidine ("T") residues. In a preferred embodiment, a cluster of 5 consecutive Ts is used as the terminator by which pol III transcription is stopped at the second or third T of the DNA template, and thus only 2 to 3 uridine ("U") residues are added to the 3' end of the coding sequence. A variety of pol III promoters can be used with the invention, including for example, the promoter fragments derived from H1 RNA genes or U6 snRNA genes of human or mouse origin or from any other species. In addition, pol III promoters can be modified/engineered to incorporate other desirable properties such as the ability to be induced by small chemical molecules, either ubiquitously or in a tissue-specific manner. For example, in one embodiment the promoter may be activated by tetracycline. In another embodiment the promoter may be activated by IPTG (lacI system).

The retroviral construct can be based on a number of retroviral vectors. In a preferred embodiment, the retroviral construct has the R and U5 sequences from a 5' lentiviral long terminal repeat (LTR) and a self-inactivating lentiviral 3' LTR. In another embodiment, the retroviral vector is derived from the murine stem cell virus (MSCV). In yet another embodiment, the retroviral construct is a hybrid of a lentiviral and a MSCV construct.

In a further embodiment, the RNA coding region encodes a self-complementary RNA molecule having a sense region, an antisense region and a loop region. Such an RNA molecule, when expressed, preferably forms a "hairpin" structure. A loop region is generally between about 2 to 15 nucleotides in length. In a preferred embodiment, the loop region is from 6 to 9 nucleotides in length. In one such embodiment of the invention, the sense region and the antisense region are between about 15 and about 30 nucleotides in length. In one embodiment, the RNA coding region of this embodiment of invention is operably linked downstream to an RNA polymerase III promoter in such that the RNA coding sequence can be precisely expressed without any extra non-coding nucleotides present at 5' end (ie., the expressed sequence is identical to the target sequence at the 5' end). The synthesis of the RNA coding region is ended at the terminator site. In one preferred embodiment the terminator has five consecutive T residues.

In another aspect of the invention, the retroviral vector can contain multiple RNA coding regions. In one such embodiment, the RNA coding region encodes a first RNA molecule, and the retroviral construct has a second RNA polymerase III promoter and a second RNA coding region operably linked to the second RNA polymerase III promoter. In this embodiment, the second RNA molecule can be substantially complementary to the first RNA molecule, such that the first and the second RNA molecules can form a double-stranded structure when expressed. The double stranded region of the RNA complex is at least about 90% identical to a target region of either a viral genome, a viral genome transcript or a target cell RNA encoding a protein necessary for the pathogenic virus life cycle. The methods of invention also include multiple RNA coding regions that encode hairpin-like self-complementary RNA molecules or other non-hairpin molecules.

In yet another embodiment of the invention, the retroviral construct has a second RNA polymerase III promoter operably linked to the same RNA coding region in the opposite direction, such that expression of the RNA coding region from the first RNA polymerase III promoter results in a synthesis of a first RNA molecule as the sense strand and expression of the RNA coding region from the second RNA polymerase III promoter results in synthesis of a second RNA molecule as antisense strand with substantial complementarity to the first RNA molecule. In such an embodiment, both RNA molecules can contain a 3' overhang of residues encoded by the termination sequence. In one embodiment, both RNA polymerase III promoters are separated from the RNA coding region by termination sequences. Preferably the termination sequences comprise five consecutive T residues.

According to another aspect of the invention, the 5' LTR sequences can be derived from HIV. The retroviral construct can also have a woodchuck hepatitis virus enhancer element sequence and/or a tRNA amber suppressor sequence.

In one embodiment of the invention, the self-inactivating 3' LTR can be a U3 element with a deletion of its enhancer sequence. In yet another embodiment, the self-inactivating 3' LTR is a modified HIV 3' LTR.

The recombinant retroviral construct can be pseudotyped, for example with the vesicular stomatitits virus envelope glycoprotein.

According to another aspect of the invention, the viral construct also can encode a gene of interest. The gene of interest can be linked to a Polymerase II promoter. A variety of Polymerase II promoters can be used with the invention, including for example, the CMV promoter. The RNA Polymerase II promoter that is chosen can be a ubiquitous promoter, capable of driving expression in most tissues, for example, the human Ubiquitin-C promoter, CMV β-actin promoter and PGK promoter. The RNA Polymerase II promoter also can be a tissue-specific promoter. Such a construct also can contain, for example, an enhancer sequence operably linked with the Polymerase II promoter.

In one embodiment, the gene of interest is a marker or reporter gene that can be used to verify that the vector was successfully transfected or transduced and its sequences expressed. In one such embodiment, the gene of interest is a fluorescent reporter gene, for example, the Green Fluorescent Protein. In yet another embodiment, the gene of interest is a drug resistant gene which can be used to select the cells that are successfully transduced. For example, the drug resistant gene can be the zeocin resistant gene (zeo). The gene of interest also can be a hybrid of a drug resistant gene and a fluorescent reporter gene, such as a zeo/gfp fusion. In another aspect of the invention, the gene of interest encodes a protein factor that can regulate the transcription activity of inducible pol III promoters. In one of such embodiment, the gene of interest is tetR (repressor for tet operon) which regulates tetracycline responsive pol III promoters.

It is another aspect of the invention to provide methods for expressing an RNA molecule or molecules within a cell. In one embodiment a packaging cell line is transfected with a retroviral construct of the invention, recombinant retroviral particles are recovered from the packaging cell line; and a target cell is infected with the recombinant retrovirus particles. According to such methods, the retroviral construct has the R and U5 sequences from a 5' lentiviral long terminal repeat (LTR), a self-inactivating lentiviral 3' LTR, a first RNA polymerase III promoter region and at least one RNA coding region. The retroviral construct also can have a termination sequence operably linked to the RNA coding region.

In a further aspect a method of treating a patient suffering from HIV infection is provided. In one embodiment, a CD34-positive target cell is isolated from the patient. The target cell is then infected with a recombinant retrovirus recovered from a packaging cell line transfected with a retroviral construct of the invention. Preferably, the recombinant retroviral construct comprises a first RNA polymerase III promoter region, at least one RNA coding region, and at least one termination sequence. In one embodiment the RNA coding region comprises a sequence that is at least about 90% identical to a target region of the HIV genome, an HIV genome transcript or a cellular gene that is involved in the HIV life cycle. The target region is preferably from about 18 to about 23 nucleotides in length.

In one embodiment the RNA coding region encodes a hairpin RNA molecule.

In a preferred embodiment, the RNA coding region is at least about 90% identical to a target region of the CCR5 gene or the CXCR4 gene.

In a still further aspect, a method of producing high titer siRNA encoding lentivirus is provided, particularly where the siRNA activity may interfere with the virus life cycle or a cellular gene.

In one embodiment a method of producing recombinant retrovirus comprises cotransfecting a packaging cell line with a retroviral construct comprising a first RNA coding region that is at least about 90% identical to a target region of a first gene and a first vector comprising a second RNA coding region that is at least about 90% identical to a target region of a second gene, wherein expression of the second gene mediates RNA interference. The first and second RNA coding regions preferably encode RNA molecules having a sense region, an antisense region and a loop region, wherein the sense region is substantially complementary to the antisense region.

The first RNA coding region is preferably at least about 90% identical to a gene selected from the group consisting of genes within the genome of a pathogenic virus, cellular genes that are involved in the lifecycle of a pathogenic virus and genes that mediate a disease or disorder. In a particular embodiment the first RNA coding region is at least about 90% identical to a gene from the HIV virus, such as gag, pol or rev.

The second gene is preferably selected from the group of genes that encode Dicer-1, Dicer-2, FMR1, eIF2C2, eIF2C1 (GERp95)/hAgo1, eIF2C2/hAgo2, hAgo3, hAgo4, hAgo5, Hiwi1/Miwi1, Hiwi2/Miwi2, Hili/Mili, Gemin3, P678 helicase, Gemin2, Gemin4, P115/slicer and VIG. More preferably the second gene encodes Dicer-1 or eIF2C2.

In one embodiment the second RNA coding region comprises a sequence that is at least about 90% identical to a portion of the gene encoding Dicer-1 or a portion of the gene encoding eIF2C2. In a particular embodiment the second RNA coding region comprises the sequence of SEQ ID NO: 8, while in another embodiment the second RNA coding region comprises the sequence of SEQ ID NO: 9.

The packaging cell line may additionally be cotransfected with a second vector comprising a third RNA coding region that is at least about 90% identical to a target region of a third gene, wherein expression of the third gene mediates RNA interference. The third gene is preferably selected from the group consisting of the genes encoding Dicer-1, Dicer-2, FMR1, eIF2C2, eIF2C1 (GERp95)/hAgo1, eIF2C2/hAgo2, hAgo3, hAgo4, hAgo5, Hiwi1/Miwi1, Hiwi2/Miwi2, Hili/

Mili, Gemin3, P678 helicase, Gemin2, Gemin4, P115/slicer and VIG. More preferably the third gene encodes Dicer-1 or eIF2C2.

In a further embodiment a method of producing recombinant retrovirus is provided comprising transfecting a packaging cell with a retroviral construct comprising a first RNA coding region that is at least about 90% identical to a portion of a target gene and inhibiting RNA interference in the packaging cell.

RNA interference is preferably inhibited by expressing siRNA in the packaging cell that is at least about 90% identical to a gene that mediates RNA interference. The siRNA may be transiently expressed in the packaging cell or stably expressed.

In another embodiment a method of producing siRNA encoding lentivirus is provided where the siRNA activity may interfere with an aspect of the virus lifecycle. A packaging cell is transfected with a vector encoding the lentivirus and siRNA activity is inhibited in the packaging cell.

In another embodiment, a method of expressing an RNA molecule within a cell is provided, including the steps of transfecting a packaging cell line with a retroviral construct, recovering a recombinant retrovirus from the packaging cell line, and infecting a target cell ex vivo with the recombinant retrovirus. The recombinant retrovirus construct can include a first RNA polymerase III promoter region, a first RNA coding region, and a first termination sequence. Expression of the RNA coding region can result in the down regulation of a target gene or genome transcript. The first RNA coding region can include an siRNA directed to CCR5 that is relatively non-cytotoxic to the target cell. In some embodiments, the RNA coding region includes the sequence of SEQ ID NO: 16. In some embodiments, the RNA coding region consistes of SEQ ID NO: 17. In some embodiments, the RNA coding region comprises a hairpin region. Expression of the RNA coding region within the target cell, in some embodiments, does not alter the growth kinetics of the target cell, which can be a human peripheral blood mononuclear cell, for at least about 10 days.

In some aspects, the retroviral construct further includes the R and U5 sequences from a 5' lentiviral long terminal repeat (LTR) and a self-inactivating lentiviral 3' LTR. In some embodiments, the RNA coding region encodes an RNA molecule having a sense region, an antisense region and a loop region. The sense region can be substantially complementary to the antisense region. The loop region can be about 2 to about 15 nucleotides in length. At least a portion of the RNA coding region can be substantially complementary to a target region. The target region can be from 15 to 30 nucleotides in length. In some embodiments, the RNA coding region is substantially complementary to a target region from 18 to 23 nucleotides in length.

In some embodiments, the packaging cell line is an HEK293 cell line. The 5' LTR sequences can be from HIV. The self-inactivating 3' LTR can include a U3 element with a deletion of its enhancer sequence, and can be a modified HIV 3' LTR. In some embodiments, the recombinant retrovirus is pseudotyped. The retrovirus can be pseudotyped with, for example, the vesicular stomatitis virus envelope glycoprotein. The 5' LTR sequences can be from Moloney Murine Leukemia Virus, or from murine stem cell virus (MSCV) in other embodiments.

The target cell is a human cell in some embodiments. The target cell can be a hematopoietic cell, which can be, for example, a CD34-positive hematopoietic cell. The target cell can be a cultured cell.

The methods can also include the step of isolating the target CD34-positive hematopoietic cells from a patient. In some aspects, the method can include the step of reintroducing the infected CD34-positive hematopoietic cell into the patient.

Also disclosed is a method of treating a patient infected with HIV. The method can include the steps of isolating a CD34-positive target cell from a patient, and infecting the target cell with a recombinant retrovirus recovered from a packaging cell line transfected with a retroviral construct. The recombinant retrovirus construct can include a first RNA polymerase III promoter region, a first RNA coding region, and a first termination sequence. Expression of the RNA coding region can result in the down regulation of CCR5.

In another aspect, a small RNA molecule is provided that includes an siRNA configured to downregulate CCR5 in a target cell. In some embodiments, the RNA coding region of the siRNA encodes SEQ ID NO: 17. The RNA coding region can include a hairpin region. The siRNA is preferably relatively non-cytotoxic with respect to the target cell. Expression of the RNA coding region within the target cell, which can be a human peripheral blood mononuclear cell, in some embodiments, does not alter the growth kinetics of the target cell for at least about 10 days. In some embodiments, the retroviral construct further includes the R and U5 sequences from a 5' lentiviral long terminal repeat (LTR) and a self-inactivating lentiviral 3' LTR. In some embodiments, the RNA coding region encodes an RNA molecule having a sense region, an antisense region and a loop region. The sense region can be substantially complementary to the antisense region. The target region can be from 18 to 23 nucleotides in length.

Also disclosed is a method of expressing an RNA molecule within a cell. The method includes the step of infecting a target cell in vitro with a recombinant retrovirus that includes a first RNA polymerase III promoter region, a first RNA coding region operably connected to the RNA polymerase III promoter region, and a first termination sequence. Expression of the RNA coding region can result in the down regulation of CCR5 in the target cell, and the RNA coding region can include the sequence of SEQ ID NO: 17.

Also disclosed is a method of downregulating CCR5 in a cell, including the step of transfecting a cell in vitro with a recombinant lentivirus comprising a first RNA polymerase III promoter region, a first RNA coding region, and a first termination sequence. The RNA coding region can include the sequence of SEQ ID NO: 17.

BRIEF DESCRIPTION OF THE DRAWINGS

FIG. 16A shows results of a study in which CEM-NKR-CCR5 cells were transduced with lentiviral vectors expressing randomly generated shRNAs against human CCR5 in 96 well plates, cultured for 3 days and analyzed by flow cytometry for CCR5 expression in a GFP-expressing population. Among the 400 shRNAs screened, human shRNA (hu1005)(SEQ ID NO: 17) reduced CCR5 more efficiently than a previously published human shRNA (hu13) (SEQ ID NO: 14), as shown in FIG. 16A. Unlike previously disclosed potent shRNAs expressed from the U6 promoter (D. S. An et al., Mol. Ther. 14, 494-504 (2006)), expression of human shRNA (hu1005)(SEQ ID NO: 17) did not alter the growth kinetics of transduced T-lymphocytes over a 12-day period of culture. As discussed below, while the hairpin form of siRNA were tested, siRNA can also include two distinct RNA molecules that are non-covalently associated to form a duplex.

FIG. 16B shows efficient reduction of endogenous CCR5 expression in human primary lymphocytes (huPBL) by siRNA (hu1005)(SEQ ID NO: 17). PHML2 activated huPBL were transduced with lentiviral vectors bearing shRNA (hu1005)(SEQ ID NO: 17) and analyzed 8 days post-infection by monoclonal antibody staining and flow cytometry for CCR5 expression in a GFP+ population. The percentage of CCR5 expression in the GFP+ population was calculated and indicated on the top of each panel. As depicted in FIGS. 16-17, the label "Mock" indicates no vector transduction. The label "No shRNA" indicates vector transduction without shRNA in the vector.

FIG. 19A shows CD45RA and CD95 (fas) expression in EGFP+ and EGFP-populations. CD45RA+/CD95(fas)− represents naïve cell type and CD45-/CD95(fas)+ represents memory cell type. FIG. 19B shows CD4/CD8 expression in EGFP+ or EGFP-populations. FIG. 19C illustrates CXCR4 expression in EGFP+ and EGFP+ populations. Quadrants were set based on isotype control staining. The percentage of positive stained cells is indicated in each quadrant.

DETAILED DESCRIPTION OF THE PREFERRED EMBODIMENT

Figure 1A:
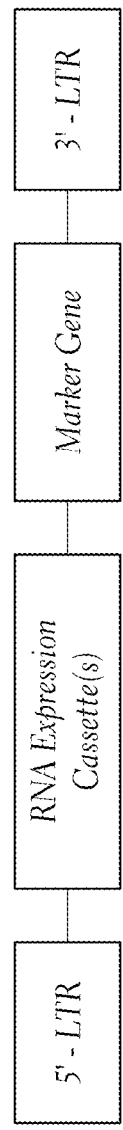
FIG. 1A shows a schematic diagram of a retroviral vector carrying an expression cassette for RNA expression, termed "RNA cassette" and a "Marker Gene" or gene of interest. The RNA expression cassette can be embedded at any permissible sites of the retroviral construct either as single copy or multiple tandem copies. In addition, although not indicated in the figure, more than one RNA expression cassette may be present in the retroviral construct.

The inventors have identified shRNA, such as shRNA hu(1005)(SEQ ID NO: 17) with particular properties that can be provided to target cells to treat, for example, HIV. Delivery of the shRNA to target cells can be accomplished in various ways. For example, methods for introducing a transgene of interest into a cell or animal are described, for example, in U.S. Patent Publication No. 2003/0101472 to Baltimore et al, the entire contents of which are incorporated herein by reference.

Unless defined otherwise, all technical and scientific terms used herein have the same meaning as commonly understood by one of ordinary skill in the art to which this invention belongs. Any methods, devices and materials similar or equivalent to those described herein can be used in the practice of this invention.

By "transgene" is meant any nucleotide sequence, particularly a DNA sequence, that is integrated into one or more chromosomes of a host cell by human intervention, such as by the methods of the present invention. In one embodiment, a transgene is an "RNA coding region." In another embodiment the transgene comprises a "gene of interest." In other embodiments the transgene can be a nucleotide sequence, preferably a DNA sequence, that is used to mark the chromosome where it has integrated. In this situation, the transgene does not have to comprise a gene that encodes a protein that can be expressed.

A "gene of interest" is a nucleic acid sequence that encodes a protein or other molecule that is desirable for integration in a host cell. In one embodiment, the gene of interest encodes a protein or other molecule the expression of which is desired in the host cell. In this embodiment, the gene of interest is generally operatively linked to other sequences that are useful for obtaining the desired expression of the gene of interest, such as transcriptional regulatory sequences.

A "functional relationship" and "operably linked" mean, without limitation, that the gene is in the correct location and orientation with respect to the promoter and/or enhancer that expression of the gene will be affected when the promoter and/or enhancer is contacted with the appropriate molecules.

An "RNA coding region" is a nucleic acid that can serve as a template for the synthesis of an RNA molecule, such as an siRNA. Preferably, the RNA coding region is a DNA sequence.

A "small interfering RNA" or "siRNA" is a double-stranded RNA molecule that is capable of inhibiting the expression of a gene with which it shares homology. The region of the gene or other nucleotide sequence over which there is homology is known as the "target region." In one embodiment the siRNA may be a "hairpin" or stem-loop RNA molecule, comprising a sense region, a loop region and an antisense region complementary to the sense region. Typically at least one of the sense and antisense regions are complementary to the target region. Such molecules can be referred to as small hairpin RNAs or "shRNAs." In other embodiments the siRNA comprises two distinct RNA molecules that are non-covalently associated to form a duplex.

The term "animal" is used in its broadest sense and refers to all animals including mammals, birds, fish, reptiles and amphibians.

The term "mammal" refers to all members of the class Mammalia and includes any animal classified as a mammal, including humans, domestic and farm animals, and zoo, sports or pet animals, such as mouse, rabbit, pig, sheep, goat, cattle and higher primates.

"Target cell" or "host cell" means a cell that is to be transformed using the methods and compositions of the invention.

The term "pathogenic virus" is used herein to indicate a virus capable of infecting an animal.

"Retroviruses" are viruses having an RNA genome.

"Lentivirus" refers to a genus of retroviruses that are capable of infecting dividing and non-dividing cells. Several examples of lentiviruses include HIV (human immunodeficiency virus: including HIV type 1, and HIV type 2), the etiologic agent of the human acquired immunodeficiency syndrome (AIDS); visna-maedi, which causes encephalitis (visna) or pneumonia (maedi) in sheep, the caprine arthritis-encephalitis virus, which causes immune deficiency, arthritis, and encephalopathy in goats; equine infectious anemia virus, which causes autoimmune hemolytic anemia, and encephalopathy in horses; feline immunodeficiency virus (FIV), which causes immune deficiency in cats; bovine immune deficiency virus (BIV), which causes lymphadenopathy, lymphocytosis, and possibly central nervous system infection in cattle; and simian immunodeficiency virus (SIV), which cause immune deficiency and encephalopathy in sub-human primates.

A "hybrid virus" as used herein refers to a virus having components from one or more other viral vectors, including element from non-retroviral vectors, for example, adenoviral-retroviral hybrids. As used herein hybrid vectors having a retroviral component are to be considered within the scope of the retroviruses.

A lentiviral genome is generally organized into a 5' long terminal repeat (LTR), the gag gene, the pol gene, the env gene, the accessory genes (nef, vif, vpr, vpu) and a 3' LTR. The viral LTR is divided into three regions called U3, R and U5. The U3 region contains the enhancer and promoter elements. The U5 region contains the polyadenylation signals. The R (repeat) region separates the U3 and U5 regions and transcribed sequences of the R region appear at both the 5' and 3' ends of the viral RNA. See, for example, "RNA Viruses: A Practical Approach" (Alan J. Cann, Ed., Oxford University Press, (2000)), 0 Narayan and Clements J. Gen. Virology 70:1617-1639 (1989), Fields et al. *Fundamental Virology Raven Press*. (1990), Miyoshi H, Blomer U, Takahashi M, Gage F H, Verma I M. *J Virol.* 72(10):8150-7 (1998), and U.S. Pat. No. 6,013,516.

Lentiviral vectors are known in the art, including several that have been used to transfect hematopoietic stem cells. Such vectors can be found, for example, in the following publications, which are incorporated herein by reference: Evans J T et al. *Hum Gene Ther* 1999; 10:1479-1489; Case S S, Price M A, Jordan C T et al. *Proc Nall Acad Sci USA* 1999; 96:2988-2993; Uchida N, Sutton R E, Friera A M et al. *Proc Natl Acad Sci USA* 1998; 95:11939-11944; Miyoshi H, Smith K A, Mosier D E et al. *Science* 1999; 283:682-686; Sutton R E, Wu H T, Rigg R et al. Human immunodeficiency virus type 1 vectors efficiently transduce human hematopoietic stem cells. *J Virol* 1998; 72:5781-5788.

"Virion," "viral particle" and "retroviral particle" are used herein to refer to a single virus comprising an RNA genome, pol gene derived proteins, gag gene derived proteins and a lipid bilayer displaying an envelope (glyco)protein. The RNA genome is usually a recombinant RNA genome and thus may contain an RNA sequence that is exogenous to the native viral genome. The RNA genome may also comprise a defective endogenous viral sequence.

A "pseudotyped" retrovirus is a retroviral particle having an envelope protein that is from a virus other than the virus from which the RNA genome is derived. The envelope protein may be from a different retrovirus or from a non-retroviral virus. A preferred envelope protein is the vesicular stomatitis virus G (VSV G) protein. However, to eliminate the possibility of human infection, viruses can alternatively be pseudotyped with ecotropic envelope protein that limits infection to a specific species, such as mice or birds. For example, in one embodiment, a mutant ecotropic envelope protein is used, such as the ecotropic envelope protein 4.17 (Powell et al. *Nature Biotechnology* 18(12):1279-1282 (2000)).

The term "provirus" is used to refer to a duplex DNA sequence present in a eukaryotic chromosome that corresponds to the genome of an RNA retrovirus. The provirus may be transmitted from one cell generation to the next without causing lysis or destruction of the host cell.

A "self-inactivating 3' LTR" is a 3' long terminal repeat (LTR) that contains a mutation, substitution or deletion that prevents the LTR sequences from driving expression of a downstream gene. A copy of the U3 region from the 3' LTR acts as a template for the generation of both LTR's in the integrated provirus. Thus, when the 3' LTR with an inactivating deletion or mutation integrates as the 5' LTR of the provirus, no transcription from the 5' LTR is possible. This eliminates competition between the viral enhancer/promoter and any internal enhancer/promoter. Self-inactivating 3' LTRs are described, for example, in Zufferey et al. *J. Virol.* 72:9873-9880 (1998), Miyoshi et al. *J. Virol.* 72:8150-8157 and Iwakuma et al. *Virology* 261:120-132 (1999).

The term "RNA interference or silencing" is broadly defined to include all posttranscriptional and transcriptional mechanisms of RNA mediated inhibition of gene expression, such as those described in P. D. Zamore, *Science* 296, 1265 (2002).

"Substantial complementarity" and "substantially complementary" as used herein indicate that two nucleic acids are at least 80% complementary, more preferably at least 90% complementary and most preferably at least 95% complementary over a region of more than about 15 nucleotides and more preferably more than about 19 nucleotides.

In one aspect of the invention, a recombinant retrovirus is used to deliver an RNA coding region of interest to a cell, preferably a mammalian cell. The cell may be a primary cell or a cultured cell. In one embodiment the cell is an oocyte or an embryonic cell, more preferably a one-cell embryo. In another embodiment the cell is a hematopoietic stem cell. The RNA coding region and any associated genetic elements are thus integrated into the genome of the host cell as a provirus. When the target cell is an embryo, the cell may then be allowed to develop into a transgenic animal by methods well known in the art.

The recombinant retrovirus used to deliver the RNA coding region is preferably a modified lentivirus, and thus is able to infect both dividing and non-dividing cells. The recombinant retrovirus preferably comprises a modified lentiviral genome that includes an RNA coding region. Further, the modified lentiviral genome preferably lacks endogenous genes for proteins required for viral replication, thus preventing undesired replication, such as replication in the target cells. The required proteins are preferably provided in trans in the packaging cell line during production of the recombinant retrovirus, as described below.

In another embodiment, the recombinant retrovirus used to deliver the RNA coding region is a modified Moloney virus, for example a Moloney Murine Leukemia Virus. In a further embodiment, the virus is a Murine Stem Cell Virus (Hawley, R. G., et al. (1996) Proc. Natl. Acad. Sci. USA 93:10297-10302; Keller, G., et al. (1998) Blood 92:877-887; Hawley, R. G., et al. (1994) Gene Ther. 1:136-138). The recombinant retrovirus also can be a hybrid virus such as that described in Choi, J K; Hoanga, N; Vilardi, A M; Conrad, P; Emerson, S G; Gewirtz, A M. (2001) Hybrid HIV/MSCV LTR Enhances Transgene Expression of Lentiviral Vectors in Human CD34+ Hematopoietic Cells. Stem Cells 19, No. 3, 236-246.

In one embodiment the transgene, preferably an RNA coding region, is incorporated into a viral construct that comprises an intact retroviral 5' LTR and a self-inactivating 3' LTR. The viral construct is preferably introduced into a packaging cell line that packages viral genomic RNA based on the viral construct into viral particles with the desired host specificity. Viral particles are collected and allowed to infect the host cell. Each of these aspects is described in detail below.

The Viral Construct

The viral construct is a nucleotide sequence that comprises sequences necessary for the production of recombinant viral particles in a packaging cell. In one embodiment the viral construct additionally comprises genetic elements that allow for the desired expression of a gene of interest in the host.

Generation of the viral construct can be accomplished using any suitable genetic engineering techniques well known in the art, including, without limitation, the standard techniques of PCR, oligonucleotide synthesis, restriction endonuclease digestion, ligation, transformation, plasmid purification, and DNA sequencing, for example as described in Sambrook et al. (Molecular Cloning: A Laboratory Manual. Cold Spring Harbor Laboratory Press, N.Y. (1989)), Coffin et al. (Retroviruses. Cold Spring Harbor Laboratory Press, N.Y. (1997)) and "RNA Viruses: A Practical Approach" (Alan J. Cann, Ed., Oxford University Press, (2000)).

The viral construct may incorporate sequences from the genome of any known organism. The sequences may be incorporated in their native form or may be modified in any way. For example, the sequences may comprise insertions, deletions or substitutions. In a preferred embodiment the viral construct comprises sequences from a lentivirus genome, such as the HIV genome or the SIV genome. In another preferred embodiment, the viral construct comprises sequences of a murine stem cell virus (MSCV).

The viral construct preferably comprises sequences from the 5' and 3' LTRs of a lentivirus, a moloney murine leukemia virus, a murine stem cell virus or hybrids thereof. In one embodiment, the viral construct comprises the R and U5 sequences from the 5' LTR of a lentivirus and an inactivated or self-inactivating 3' LTR from a lentivirus. The LTR sequences may be LTR sequences from any lentivirus from any species. For example, they may be LTR sequences from HIV, SIV, FIV or BIV. Preferably the LTR sequences are HIV LTR sequences. The virus also can incorporate sequences from MMV or MSCV.

The viral construct preferably comprises an inactivated or self-inactivating 3' LTR. The 3' LTR may be made self-inactivating by any method known in the art. In one embodiment the U3 element of the 3' LTR contains a deletion of its enhancer sequence, preferably the TATA box, Sp1 and NF-kappa B sites. As a result of the self-inactivating 3' LTR, the provirus that is integrated into the host cell genome will comprise an inactivated 5' LTR.

Optionally, the U3 sequence from the lentiviral 5' LTR may be replaced with a promoter sequence in the viral construct. This may increase the titer of virus recovered from the packaging cell line. An enhancer sequence may also be included. Any enhancer/promoter combination that increases expression of the viral RNA genome in the packaging cell line may be used. In one such embodiment the CMV enhancer/promoter sequence is used (U.S. Pat. No. 5,168,062; Karasuyama et al *J. Exp. Med.* 169:13 (1989).

The viral construct also comprises a transgene. The transgene, may be any nucleotide sequence, including sequences that serve as markers for the provirus. Preferably the transgene comprises one or more RNA coding regions and/or one or more genes of interest.

In the preferred embodiment the transgene comprises at least one RNA coding region. Preferably the RNA coding region is a DNA sequence that can serve as a template for the expression of a desired RNA molecule in the host cell. In one embodiment, the viral construct comprises two or more RNA coding regions.

The viral construct also preferably comprises at least one RNA Polymerase III promoter. The RNA Polymerase III promoter is operably linked to the RNA coding region and can also be linked to a termination sequence. In addition, more than one RNA Polymerase III promoter may be incorporated.

RNA polymerase III promoters are well known to one of skill in the art. A suitable range of RNA polymerase III promoters can be found, for example, in Paule and White. *Nucleic Acids Research.*, Vol 28, pp 1283-1298 (2000), which is hereby incorporated by reference in its entirety. The definition of RNA polymerase III promoters also include any synthetic or engineered DNA fragment that can direct RNA polymerase III to transcribe its downstream RNA coding sequences. Further, the RNA polymerase III (Pol III) promoter or promoters used as part of the viral vector can be inducible. Any suitable inducible Pol III promoter can be used with the methods of the invention. Particularly suited Pol III promoters include the tetracycline responsive promoters provided in Ohkawa and Taira Human Gene Therapy, Vol. 11, pp 577-585 (2000) and in Meissner et al. *Nucleic Acids Research*, Vol. 29, pp 1672-1682 (2001), which are incorporated herein by reference.

In one embodiment the viral construct further comprises a gene that encodes a protein that is desirably expressed in one or more of the target cells, for example, a reporter or marker protein. Preferably the gene of interest is located between the 5' LTR and 3' LTR sequences. Further, the gene of interest is preferably in a functional relationship with other genetic elements, for example transcription regulatory sequences such as promoters and/or enhancers, to regulate expression of the gene of interest in a particular manner once the gene of interest is incorporated into the target cell genome. In certain embodiments, the useful transcriptional regulatory sequences are those that are highly regulated with respect to activity, both temporally and spatially.

Preferably the gene of interest is in a functional relationship with an internal Polymerase II promoter/enhancer regulatory sequences. An "internal" promoter/enhancer is one that is located between the 5' LTR and the 3' LTR sequences in the viral construct and is operably linked to the gene that is desirably expressed.

The Polymerase II promoter/enhancer may be any promoter, enhancer or promoter/enhancer combination known to increase expression of a gene with which it is in a functional relationship. A "functional relationship" and "operably linked" mean, without limitation, that the transgene or RNA coding region is in the correct location and orientation with respect to the promoter and/or enhancer that expression of the gene will be affected when the promoter and/or enhancer is contacted with the appropriate molecules.

In another embodiment, the gene of interest is a gene included for safety concerns to allow for the selective killing of the treated target cells within a heterogeneous population, for example within an animal, or more particularly within a human patient. In one such embodiment, the gene of interest is a thymidine kinase gene (TK) the expression of which renders a target cell susceptible to the action of the drug gancyclovir.

In addition, more than one gene of interest may be placed in functional relationship with the internal promoter. For example a gene encoding a marker protein may be placed after the primary gene of interest to allow for identification of cells that are expressing the desired protein. In one embodiment a fluorescent marker protein, preferably green fluorescent protein (GFP), is incorporated into the construct along with the gene of interest. If a second reporter gene is included, an internal ribosomal entry site (IRES) sequence is also preferably included (U.S. Pat. No. 4,937,190). The IRES sequence may facilitate the expression of the reporter gene.

The viral construct may also contain additional genetic elements. The types of elements that may be included in the construct are not limited in any way and will be chosen by the skilled practitioner to achieve a particular result. For example, a signal that facilitates nuclear entry of the viral genome in the target cell may be included. An example of such a signal is the HIV-1 flap signal.

Further, elements may be included that facilitate the characterization of the provirus integration site in the genome of the animal. For example, a tRNA amber suppressor sequence may be included in the construct.

In addition, the construct may contain one or more genetic elements designed to enhance expression of the gene of interest. For example, a woodchuck hepatitis virus responsive element (WRE) may be placed into the construct (Zufferey et al. *J. Virol.* 74:3668-3681 (1999); Deglon et al. *Hum. Gene Ther.* 11:179-190 (2000)).

A chicken β-globin insulator (Chung et al. *Proc. Natl. Acad. Sci. USA* 94:575-580 (1997)) may also be included in the viral construct. This element has been shown to reduce the chance of silencing the integrated provirus in a target cell due to methylation and heterochromatinization effects. In addition, the insulator may shield the internal enhancer, promoter and exogenous gene from positive or negative positional effects from surrounding DNA at the integration site on the chromosome.

Any additional genetic elements are preferably inserted 3' of the gene of interest or RNA coding region.

In a specific embodiment, the viral vector comprises: an RNA pol III promoter sequence; the R and U5 sequences from the HIV 5' LTR; the HIV-1 flap signal; an internal enhancer; an internal promoter; a gene of interest; the woodchuck hepatitis virus responsive element; a tRNA amber suppressor sequence; a U3 element with a deletion of its enhancer sequence; the chicken β-globin insulator; and the R and U5 sequences of the 3' HIV LTR.

The viral construct is preferably cloned into a plasmid that may be transfected into a packaging cell line. The preferred plasmid preferably comprises sequences useful for replication of the plasmid in bacteria.

Figure 1B:
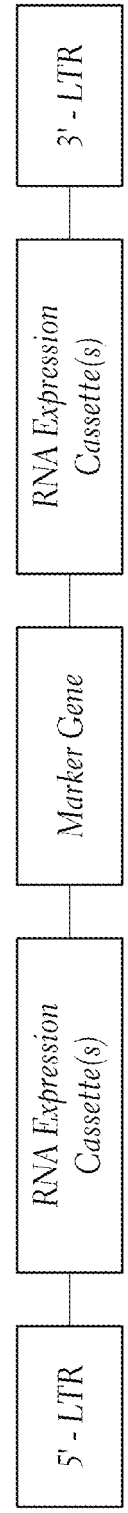
FIG. 1B shows a similar construct in which the RNA expression cassettes flank a marker gene.

Schematic diagrams of exemplary retroviral constructs are shown in FIGS. 1A and 1B.

Production of Virus

Any method known in the art may be used to produce infectious retroviral particles whose genome comprises an RNA copy of the viral construct described above.

Preferably, the viral construct is introduced into a packaging cell line. The packaging cell line provides the viral proteins that are required in trans for the packaging of the viral genomic RNA into viral particles. The packaging cell line may be any cell line that is capable of expressing retroviral proteins. Preferred packaging cell lines include 293 (ATCC CCL X), HeLa (ATCC CCL 2), D17 (ATCC CCL 183), MDCK (ATCC CCL 34), BHK (ATCC CCL-10) and Cf2Th (ATCC CRL 1430). The most preferable cell line is the 293 cell line.

The packaging cell line may stably express the necessary viral proteins. Such a packaging cell line is described, for example, in U.S. Pat. No. 6,218,181. Alternatively a packaging cell line may be transiently transfected with plasmids comprising nucleic acid that encodes the necessary viral proteins.

In one embodiment a packaging cell line that stably expresses the viral proteins required for packaging the RNA genome is transfected with a plasmid comprising the viral construct described above.

In another embodiment a packaging cell line that does not stably express the necessary viral proteins is co-transfected with two or more plasmids essentially as described in Yee et al. (*Methods Cell. Biol.* 43A, 99-112 (1994)). One of the plasmids comprises the viral construct comprising the RNA coding region. The other plasmid(s) comprises nucleic acid encoding the proteins necessary to allow the cells to produce functional virus that is able to infect the desired host cell.

The packaging cell line may not express envelope gene products. In this case the packaging cell line will package the viral genome into particles that lack an envelope protein. As the envelope protein is responsible, in part, for the host range of the viral particles, the viruses are preferably pseudotyped. Thus the packaging cell line is preferably transfected with a plasmid comprising sequences encoding a membrane-associated protein that will permit entry of the virus into a host cell. One of skill in the art will be able to choose the appropriate pseudotype for the host cell that is to be used. For example, in one embodiment the viruses are pseudotyped with the vesicular stomatitis virus envelope glycoprotein (VSVg). In addition to conferring a specific host range this pseudotype may permit the virus to be concentrated to a very high titer. Viruses can alternatively be pseudotyped with ecotropic envelope proteins that limit infection to a specific species, such as mice or birds. For example, in another embodiment, a mutant ecotropic envelope protein is used, such as the ecotropic envelope protein 4.17 (Powell et al. *Nature Biotechnology* 18(12):1279-1282 (2000)).

In the preferred embodiment a packaging cell line that does not stably express viral proteins is transfected with the viral construct, a second vector comprising the HIV-1 packaging vector with the env, nef, 5'LTR, 3'LTR and vpu sequences deleted, and a third vector encoding an envelope glycoprotein. Preferably the third vector encodes the VSVg envelope glycoprotein.

If the viral construct described above comprises siRNA that is directed against a cellular gene or a viral gene, particularly an essential gene such as a gene involved in the virus life cycle, viral production in the packaging cells may be severely reduced. Thus, in another embodiment of invention, RNA interference activity in the packaging cells is suppressed to improve the production of recombinant virus. By suppressing RNA interference in the packaging cell line, sufficient quantities of recombinant retrovirus that expresses siRNA targeting essential genes, such as Cis-regulatory elements required for the HIV-1 life cycle, can be produced to facilitate its therapeutic use.

Suppression of siRNA activity that reduces virus production may be accomplished, for example, by interfering with one or more components necessary for RNA interference. Such components include, for example, molecules in the pathway by which inactive, hairpin precursor siRNAs are processed into open-ended double-stranded mature siRNAs and molecules involved in the formation and function of the RNA-Induced-Silencing-Complex (RISC), which is essential for target RNA degradation. Exemplary components necessary for RNA interference include, but are not limited to RNase III family members such as Dicer-1 and Dicer-2 (Hammond et al. Nat. Rev. Genet. 2:110-119 (2001)), Dicer associated proteins such as FMR1 (Ishizuka et al. Genes Dev. 16:2497-2508 (2002); Caudy et al. Genes Dev. 16:2491-2496 (2002)), Argonaute proteins including members of the Ago1 subfamily of Argonaute proteins (Carmell et al. Genes Dev. 16(21):2733-2742 (2002)) such as eIF2C2, eIF2C1 (GERp95)/hAgo1, eIF2C2/hAgo2, hAgo3, hAgo4 and hAgo5, members of the Piwi subfamily of Argonaute proteins (Carmell et al. Genes Dev. 26:2733-2742 (2002)) such as Hiwi1/Miwi1, Hiwi2/Miwi2 and Hili/Mili, which are required for the assembly and activity of RISC (Mourelatos et al. Genes Dev. 16(6):720-728 (2002); Carmell et al. Genes Dev. 16(21):2733-2742 (2002)), RNA helicases such as Gemin3 (Mourelatos et al. Genes Dev. 16(6):720-728 (2002)) and P678 helicase (Ishizuka et al., supra) and other RISC/miRNP associated proteins such as Gemin2, Gemin4, P115/slicer and VIG (Mourelatos et al. Genes Dev. 16(6): 720-728 (2002); Schwarz and Zamore Genes Dev. 16:1025-1031 (2002); Caudy et al. Genes Dev. 16:2491-2496 (2002)). However, any component that is known in the art to be necessary for full siRNA activity may be targeted.

Suppression of RNA interference activity may be accomplished by any method known in the art. This includes, without limitation, the cotransfection or stable transfection of constructs expressing siRNA molecules in packaging cells to inhibit molecules that play a role in RNA interference.

In one embodiment production of virus from the packaging cell line is increased by cotransfection of one or more vectors that express an siRNA molecule that inhibits RNA interference, such as an siRNA molecule that inhibits Dicer activity and/or eIF2C2 activity. In a preferred embodiment, a packaging cell line is created that stably expresses one or more molecules that inhibit RNA interference, such as siRNAs that inhibit Dicer activity and/or eIF2C2 activity.

The recombinant virus is then preferably purified from the packaging cells, titered and diluted to the desired concentration.

Delivery of the Virus

The virus may be delivered to the cell in any way that allows the virus to infect the cell. Preferably the virus is allowed to contact the cell membrane. A preferred method of delivering the virus to mammalian cells is through direct contact.

In one embodiment, the target cells are preferably contacted with the virus in culture plates. The virus may be suspended in media and added to the wells of a culture plate. The media containing the virus may be added prior to the plating of the cells or after the cells have been plated. Preferably cells are incubated in an appropriate amount of media to provide viability and to allow for suitable concentrations of virus in the media such that infection of the host cell occurs.

The cells are preferably incubated with the virus for a sufficient amount of time to allow the virus to infect the cells. Preferably the cells are incubated with virus for at least 1 hour, more preferably at least 5 hours and even more preferably at least 10 hours.

In any such embodiments, any concentration of virus that is sufficient to infect the cell may be used. When the target cell is to be cultured, the concentration of the viral particles is at least 1 pfu/µl, more preferably at least 10 pfu/µl, even more preferably at least 400 pfu/µl and even more preferably at least $1 \times 10^4$ pfu/µl.

Following infection with the virus, the cells can be introduced into an animal. The location of introduction of cultured cells will depend on the cell type used. For example, when the cells are hematopoietic cells, the cells can be introduced into the peripheral blood stream. The cells introduced into an animal are preferably cells derived from that animal, to avoid an adverse immune response. Cells also can be used that are derived from a donor animal having a similar immune makeup. Other cells also can be used, including those designed to avoid an immunogenic response.

In another embodiment, a suitable amount of virus is introduced into an animal directly, for example though injection into the body. In one such embodiment, the viral particles are injected into the animal's peripheral blood stream. Other injection locations also are suitable. Depending on the type of virus, introduction can be carried out through other means including for example, inhalation, or direct contact with epithelial tissues, for example those in the eye, mouth or skin.

The cells and animals incorporating introduced cells may be analyzed, for example for integration of the RNA coding region, the number of copies of the RNA coding region that integrated, and the location of the integration. Such analysis may be carried out at any time and may be carried out by any methods known in the art. Standard techniques are described, for example, in Hogan et al. (supra).

The methods of infecting cells disclosed above do not depend upon species-specific characteristics of the cells. As a result, they are readily extended to all mammalian species.

As discussed above, the modified retrovirus can be pseudotyped to confer upon it a broad host range. One of skill in the art would also be aware of appropriate internal promoters to achieve the desired expression of a gene of interest in a particular animal species. Thus, one of skill in the art will be able to modify the method of infecting cells derived from any species.

Down-Regulating Gene Expression in a Target Cell

The methods described herein allow the expression of RNA molecules in cells, and are particularly suited to the expression of small RNA molecules, which cannot be readily expressed from a Pol II promoter. According to a preferred embodiment of the invention, an RNA molecule is expressed within a cell in order to down-regulate the expression of a target gene. The ability to down-regulate a target gene has many therapeutic and research applications, including identifying the biological functions of particular genes. Using the techniques and compositions of the invention, it will be possible to knock-down (or down-regulate) the expression of a large number of genes, both in cell culture and in mammalian organisms. In particular, it is desirable to down-regulate genes in a target cell that are necessary for the life cycle of a pathogen, such as a pathogenic virus.

In preferred embodiments of the invention, an RNA expression cassette comprises a Pol III promoter and an RNA coding region. The RNA coding region preferably encodes an RNA molecule that is capable of down-regulating the expression of a particular target gene or genes. The RNA molecule encoded can, for example, be complementary to the sequence of an RNA molecule encoding a gene to be down-regulated. In such an embodiment, the RNA molecule is designed to act through an antisense mechanism.

A more preferred embodiment involves the expression of a double-stranded RNA complex, or an RNA molecule having a stem-loop or a so-called "hairpin" structure. As used herein, the term "RNA duplex" refers to the double stranded regions of both the RNA complex and the double-stranded region of the hairpin or stem-lop structure. An RNA coding region can encode a single stranded RNA, two or more complementary single stranded RNAs or a hairpin forming RNA.

Double stranded RNA has been shown to inhibit gene expression of genes having a complementary sequence through a process termed RNA interference or suppression (see, for example, Hammond et al. Nat. Rev. Genet. 2:110-119 (2001)).

According to the invention, the RNA duplex or siRNA corresponding to a region of a target gene to be down-regulated is expressed in the cell. The RNA duplex is substantially identical (typically at least about 80% identical, and more typically at least about 90% identical) in sequence to the sequence of the gene targeted for down regulation. siRNA duplexes are described, for example, in Bummelkamp et al. Science 296:550-553 (2202), Caplen et al. Proc. Natl. Acad. Sci. USA 98:9742-9747 (2001) and Paddison et al. Genes & Devel. 16:948-958 (2002).

The RNA duplex is generally at least about 15 nucleotides in length and is preferably about 15 to about 30 nucleotides in length. In some organisms, the RNA duplex can be significantly longer. In a more preferred embodiment, the RNA duplex is between about 19 and 22 nucleotides in length. The RNA duplex is preferably identical to the target nucleotide sequence over this region.

When the gene to be down regulated is in a family of highly conserved genes, the sequence of the duplex region can be chosen with the aid of sequence comparison to target only the desired gene. If there is sufficient identity among a family of homologous genes within an organism, a duplex region can be designed that would down regulate a plurality of genes simultaneously.

Figure 2:
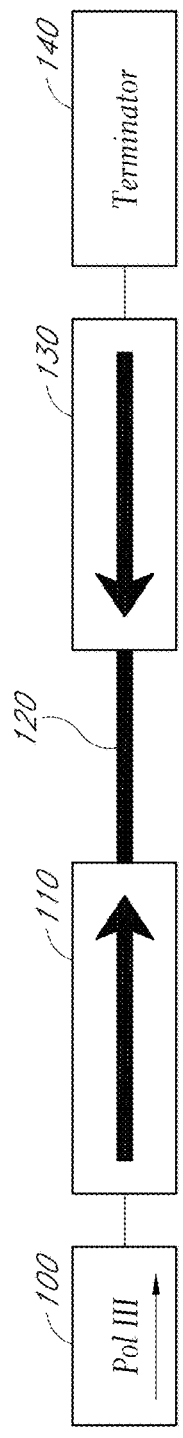
FIG. 2 shows a schematic view of an RNA expression cassette having a RNA polymerase III promoter 100 linked to an siRNA region 110-130, having a sense region 110, a loop region 120, and an antisense region 130, and a terminator sequence 140.

The duplex RNA can be expressed in a cell from a single retroviral construct. In the preferred embodiment, a single RNA coding region in the construct is a serves as a template for the expression of a self-complementary hairpin RNA, comprising a sense region, a loop region and an antisense region. This embodiment is illustrated in FIG. 2, which shows a schematic view of an RNA expression cassette having an RNA Pol III promoter 100 operatively linked to an RNA coding region, having a sense region 110, a loop region 120, an antisense region 130 and a terminator region 140. The sense 110 and antisense 130 regions are each preferably about 15 to about 30 nucleotides in length. The loop region 120 preferably is about 2 to about 15 nucleotides in length, more preferably from about 4 to about 9 nucleotides in length. Following expression the sense and antisense regions form a duplex.

Figure 3:
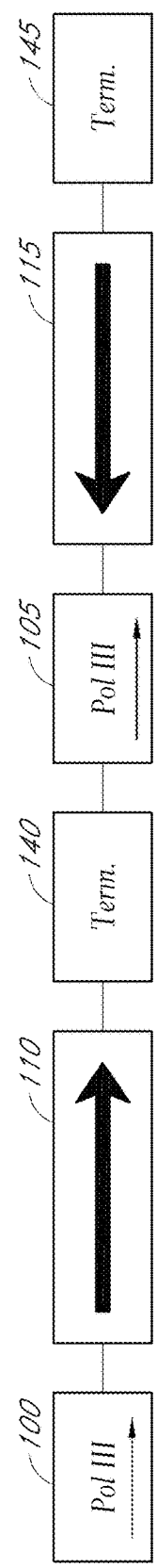
FIG. 3 shows a schematic view of an RNA expression cassette having a RNA polymerase III promoter 100 linked to a first RNA coding region 110 and a first terminator sequence 140 and a second RNA polymerase III promoter 105 linked to a second RNA coding region 115 and a second terminator 145.

In another embodiment, the retroviral construct comprises two RNA coding regions. The first coding region is a template for the expression of a first RNA and the second coding region is a template for the expression of a second RNA. Following expression, the first and second RNA's form a duplex. The retroviral construct preferably also comprises a first Pol III promoter operably linked to the first RNA coding region and a second Pol III promoter operably linked to the second RNA coding region. This embodiment is illustrated in FIG. 3, which shows a schematic view of an RNA expression cassette having an RNA Polymerase III promoter 100 linked to a first RNA coding region 110 and a first terminator sequence 140 and a second RNA polymerase III promoter 105 linked to a second RNA coding region 115 and a second terminator 145.

Figure 4:
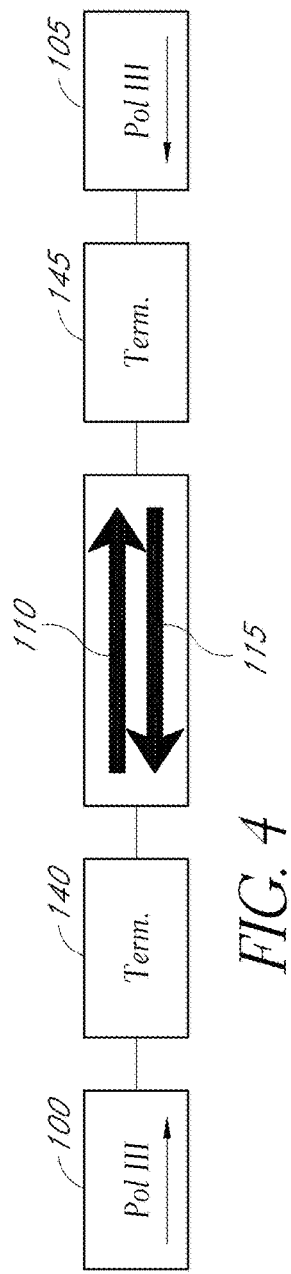
FIG. 4 shows a schematic view of an RNA expression cassette having a first RNA polymerase III promoter 100 linked to an RNA coding region 110 and a first terminator sequence 145. The expression cassette has a second RNA polymerase III promoter 105 linked to the RNA coding region 115, the same sequence as 110 in reverse, and a second terminator 140.

In yet another embodiment of the invention, the retroviral construct comprises a first RNA Pol III promoter operably linked to a first RNA coding region, and a second RNA Pol III promoter operably linked to the same first RNA coding region in the opposite direction, such that expression of the RNA coding region from the first RNA Pol III promoter results in a synthesis of a first RNA molecule as the sense strand and expression of the RNA coding region from the second RNA Pol III promoter results in synthesis of a second RNA molecule as an antisense strand that is substantially complementary to the first RNA molecule. In one such embodiment, both RNA Polymerase III promoters are separated from the RNA coding region by termination sequences, preferably termination sequences having five consecutive T residues. FIG. 4 shows a schematic view of an RNA expression cassette having a first RNA Polymerase III promoter 100 linked to an RNA coding region 110 and a first terminator sequence 145. The expression cassette has a second RNA polymerase III promoter 105 linked to the RNA coding region 115, the same sequence as 110 in reverse, and a second terminator 140.

In further embodiments an RNA duplex is expressed using two or more retroviral constructs. In one embodiment, a first retroviral construct is used that directs the expression of a first RNA and a second retroviral construct is used that directs expression of a second RNA that is complementary to the first. Following expression the first and second RNAs form a duplex region. It is preferred, however, that the entire duplex region is introduced using retroviral particles derived from a single retroviral construct. As discussed above, several strategies for expressing a duplex RNA from a single viral construct are shown in FIGS. 2-4.

The RNA duplexes may be flanked by single stranded regions on one or both sides of the duplex. For example, in the case of the hairpin, the single stranded loop region would connect the duplex region at one end.

The RNA coding region is generally operatively linked to a terminator sequence. The pol III terminators preferably comprise of stretches of 4 or more thymidine ("T") residues. In a preferred embodiment, a cluster of 5 consecutive Ts is linked immediately downstream of the RNA coding region to serve as the terminator. In such a construct pol III transcription is terminated at the second or third T of the DNA template, and thus only 2 to 3 uridine ("U") residues are added to the 3' end of the coding sequence.

The sequence of the RNA coding region, and thus the sequence of the RNA duplex, preferably is chosen to be complementary to the sequence of a gene whose expression is to be downregulated in a cell or organism. The degree of down regulation achieved with a given RNA duplex sequence for a given target gene will vary by sequence. One of skill in the art will be able to readily identify an effective sequence. For example, in order to maximize the amount of suppression, a number of sequences can be tested in cell culture prior to treating a target cell or generating a transgenic animal. As an understanding of the sequence requirements for RNA interference is determined, the RNA duplex can be selected by one of skill in the art.

Inhibition of Viral Replication and/or Gene Expression in a Target Cell

According to one aspect of the invention, the target of the RNA duplex is a sequence that is necessary for the life cycle or replication of a virus, including for example, gene expression of the virus and the expression of a cellular receptor or co-receptor necessary for viral replication. In one embodiment of the invention, the virus to be inhibited is the human immunodeficiency virus (HIV). In particular embodiments the target sequence is selected from the group consisting of Rev, Gag, Pol, LTRs, TAR, RRE, ψ, att, pbs, ppt and other essential DNA and RNA cis-regulatory elements.

The invention also includes methods of treating a patient having a viral infection. In one embodiment the method comprises administering to the patient an effective amount of a recombinant retroviral particle (or particles) encoding at least one double stranded RNA having at least 90% homology and preferably identical to a region of at least about 15 to 25 nucleotides in a nucleotide that is important for normal viral replication. For example, the double stranded RNA may have homology to a nucleic acid in a viral genome, a viral gene transcript or in a gene for a patient's cellular receptor that is necessary for the life cycle of the virus.

In one embodiment, the patient to be treated is infected with the human immunodeficiency virus. A target cell is removed from a patient prior to treatment with the recombinant virus particle. In a preferred embodiment, the target cell is a CD34-positive hematopoietic stem cell. Such stem cells can be purified by one of skill in the art. Methods for such purification are known and taught for example in U.S. Pat. Nos. 4,965,204; 4,714,680; 5,061,620; 5,643,741; 5,677,136; 5,716,827; 5,750,397 and 5,759,793. One method for purifying such CD34-positive stem cells involves centrifugation of peripheral blood samples to separate mononuclear cells and granulocytes and sorting by fluorescence activated cell sorting (FACS). Sorted cells can be enriched for CD34+ cells through any of the above techniques. In a particular embodiment, the cells are enriched for CD34+ cells through a magnetic separation technology such as that available from Miltenyi Biotec and described in the following publications: Kogler et al. (1998) Bone Marrow Transplant. 21: 233-241; Pasino et al. (2000) Br. J. Haematol. 108: 793-800. The isolated CD34-positive stem cell is treated with a recombinant retroviral particle having an RNA coding region encoding a double stranded RNA directed against one or more targets within the viral genome and/or cellular targets that are necessary for the viral life cycle, including, for example, receptors or co-receptors necessary for entry of the pathogenic virus. The treated stem cells are then reintroduced into the patient.

The methods of the invention can be used to treat a variety of viral diseases, including, for example, human immunodeficiency virus (HIV-1 and HIV-2), hepatitis A, B, C, D, E, and G, human pailloma virus (HPV), and herpes simplex virus (HSV).

It is also possible to treat a patient with an anti-viral recombinant retrovirus in order to confer immunity or increased resistance for the patient to a desired pathogen, such as a virus.

Cellular Targets

According to the invention, one of skill in the art can target a cellular component, such as an RNA or an RNA encoding a cellular protein necessary for the pathogen life cycle, particularly a viral life cycle. In a preferred embodiment, the cellular target chosen will not be a protein or RNA that is necessary for normal cell growth and viability. Suitable proteins for disrupting the viral life cycle include, for example, cell surface receptors involved in viral entry, including both primary receptors and secondary receptors, and transcription factors involved in the transcription of a viral genome, proteins involved in integration into a host chromosome, and proteins involved in translational or other regulation of viral gene expression.

A number of cellular proteins are known to be receptors for viral entry into cells. Some such receptors are listed in an article by E. Baranowski, C. M. Ruiz-Jarabo, and E. Domingo, "Evolution of Cell Recognition by Viruses," Science 292: 1102-1105, which is hereby incorporated by reference in its entirety. Some cellular receptors that are involved in recognition by viruses are listed below: Adenoviruses: CAR, Integrins, MHC I, Heparan sulfate glycoaminoglycan, Siliac Acid; Cytomegalovirus: Heparan sulfate glycoaminoglycan; Coxsackieviruses: Integrins, ICAM-1, CAR, MHC I; Hepatitis A: murine-like class I integral membrane glycoprotein; Hepatitis C: CD81, Low density lipoprotein receptor; HIV (Retroviridae): CD4, CXCR4, Heparan sulfate glycoaminoglycan; HSV: Heparan sulfate glycoaminoglycan, PVR, HveB, HveC; Influenza Virus: Sialic acid; Measles: CD46, CD55; Poliovirus, PVR, HveB, HveC; Human papillomavirus: Integrins. One of skill in the art will recognize that the invention is not limited to use with receptors that are currently known. As new cellular receptors and co-receptors are discovered, the methods of the invention can be applied to such sequences.

Human Immunodeficiency Virus (HIV)
HIV Viral Targets:

In one embodiment of the invention, the retroviral construct has an RNA coding region that encodes a double stranded molecule having at least 90% homology to the HIV viral RNA genome, an expressed region of the HIV viral genome, for example, to any region of about 19-25 nucleotides in length of the 9-kb transcript of the integrated HIV virus, or any of the variously spliced mRNA transcripts of HIV (Schwartz, S; Felber, B K; Benko, D M; Fenya, E M; Pavlakis, G N. Cloning and functional analysis of multiply spliced mRNA species of human immunodeficiency virus type 1. *J. Virol.* 1990; 64(6): 2519-29). Target regions within the HIV transcripts can be chosen to correspond to any of the HIV viral genes, including, for example, HIV-1 LTR, vif, nef, and rev. In another embodiment, the RNA coding region encodes a double stranded region having at least 90% homology to a receptor or co-receptor of the HIV virus. For example, the primary receptor for HIV entry into T cells is CD4. In a preferred embodiment, the co-receptors CXC chemokine receptor 4 (CXCR4) and CC chemokine receptor 5 (CCR5) are down-regulated according to the methods of the invention. CXCR4 (Feddersppiel et al. *Genomics* 16:707-712 (1993)) is the major co-receptor for T cell trophic strains of HIV while CCR5 (Mummidi et al. *J. Biol. Chem.* 272: 30662-30671 (1997)) is the major co-receptor for macrophage trophic strains of HIV. Other cellular targets against HIV include the RNA transcripts for proteins involved in the HIV life cycle, including cyclophilin, CRM-1, importin-β, HP68 (Zimmerman C, et al. Identification of a host protein essential for assembly of immature HIV-1 capsids. *Nature* 415 (6867): 88-92 (2002)) and other as yet unknown cellular factors. CCR5 is a preferred target because it is not an essential human gene yet it is essential for infection by most strains of HIV-1. Individuals who are homozygous for the CCR5 delta 32 allele that prevents CCR5 cell surface expression are resistant to HIV-1 infection but otherwise apparently normal (See, e.g., R. Liu et al., *Cell* 86, 367-377 (1996); M. Samson et al., *Nature* 382, 722-725 (1996); M. Dean et al., *Science* 273, 1856-1862 (1996); Y. Huang et al., *Nat Med* 2, 1240-1243 (1996)). Because HIV-1 infects predominately T-cells and macrophages, hematopoietic stem cell transplant can be utilized to stably express siRNA to CCR5 and down-regulate CCR5 in progeny cells that are targets for HIV-1 infection. Furthermore, a non-toxic siRNA to CCR5, for example, can provide the foundation for further optimization of potency, both alone and in combination with other "genetic immunization" reagents directed against HIV. When applied therapeutically in an in vivo setting, the intense HIV-1 driven selection pressures can result in selection over time of resistant cells expressing low levels of CCR5.

Reduction of Target Cell Cytotoxicity

In some embodiments, a small RNA molecule, for example, a small hairpin RNA (shRNA) is not associated with significant target cell cytotoxicity or other adverse effects after being expressed in the target cell. In one embodiment, a small RNA molecule is configured to have an acceptable level of cytotoxicity to a cellular target, while also able to stably down-regulate a target gene in vitro or when introduced ex vivo or in vivo into a living organism. By screening various libraries of small RNA molecules, such as siRNA directed to a particular target sequence of a target gene, small RNA molecules can be identified that: (1) have relatively low levels of toxicity to a target cell and (2) are able to stably down-regulate a target gene of a target cell. An example of such a screen is described in Example 9 below.

In some embodiments, a relatively non-cytotoxic small RNA molecule is directed to a gene within the genome of a pathogenic virus (e.g., HIV), a cellular gene that is involved in the life cycle of a pathogenic virus, or a gene that mediate a disease or disorder. In one embodiment, an siRNA is identified that can downregulate CCR5 without resulting in significant cytotoxicity to a transduced peripheral blood mononuclear cell (PBMC). The relatively non-cytotoxic siRNA (also referred to herein as a non-cytotoxic siRNA), which can be an shRNA in some embodiments, can be expressed in the PBMC, preferably using the H1 promoter in combination with a lentiviral vector. In a preferred embodiment, expression of a non-cytotoxic small RNA molecule within a transduced target cell does not alter the growth kinetics of the target cell for at least about 1, 2, 3, 4, 5, 6, 8, 10, 12, 15, 30, 60, 90, 180, 360, 720 days, or more. In this or other embodiments, a small RNA molecule has an acceptable cytotoxicity, or in other words, is relatively non-cytotoxic to a target cell, if it does not cause, or causes relatively less of the following effects compared to other known siRNAs such as previously described shRNA (hu13) (D. S. An et al., Mol. Ther. 14, 494-504 (2006): induction of interferon response genes (see R. J. Fish and E. K. Kruithof, BMC. Mol. Biol. 5, 9 (2004)), global change of mRNA expression profiles caused by off target effects (see A. L. Jackson et al., RNA. 12, 1179-1187 (2006)) or cytotoxic effects due to miRNA disregulation (D. Grimm et al., Nature. 441, 537-541 (2006)). A non-limiting example of such shRNAs, directed toward CCR5, is the shRNA provided in SEQ ID NO: 17 (hu1005).

Anti-CCR5 shRNAs

As discussed in Example 9 below, in a screen of over 400 shRNAs, shRNA (hu1005)(SEQ ID NO: 17) reduced CCR5 more efficiently than a previously published shRNA (hu13) (SEQ ID NO: 14), as shown in FIG. 16A. An siRNA against cCCR5 preferably comprises a region complementary or substantially complementary to a target region of CCR5, for example, the region of SEQ ID NO: 16. In some embodiments, the siRNA is an shRNA and thus includes a hairpin region. In one embodiment, the siRNA has a sense region, an antisense region, and a loop region. The sense region is preferably substantially complementary to the antisense region. The loop region can be from about 2 nucleotides to about 15 nucleotides in length in some embodiments. In a preferred embodiment of an siRNA directed to CCR5, a small RNA molecule comprises a region from, e.g., between about 1 to about 50 nucleotides in length, preferably between about 10 to about 30 nucleotides in length, more preferably between about 15 to about 25 nucleotides in length, such as about 20 nucleotides in length; the region being at least about 70%, 80%, 90%, 95%, or more identical to SEQ ID NO: 17.

The following examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

All patent and literature references cited in the present specification are hereby incorporated by reference in their entirety.

EXAMPLES

Example 1

Figure 5:
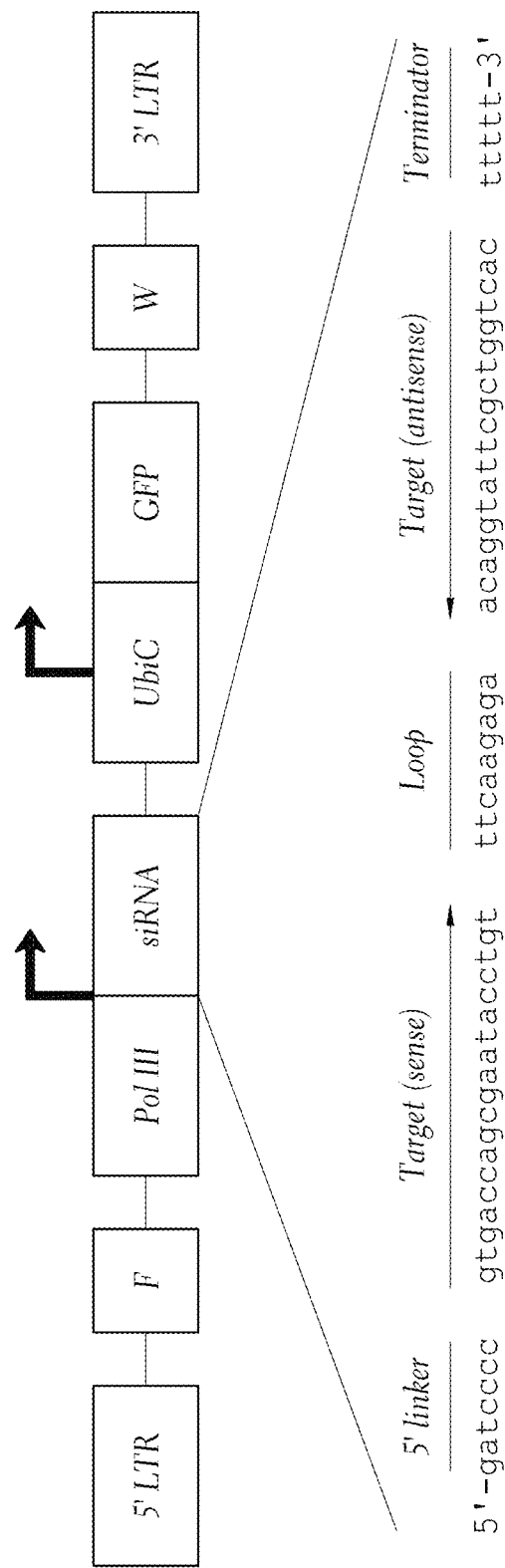
FIG. 5. Schematic illustration of a lacZ siRNA encoding lentiviral vector. 5'LTR: an HIV based lentiviral vector 5' LTR; F: an HIV Flap element; pol III: a human H1-RNA pol III promoter (−240 to −8); siRNA: a lacZ specific small hairpin RNA coding region and its structure and detailed sequence are illustrated below. UbiC: an internal human ubiquitinC promoter; GFP: a GFP marker gene driven by UbiC promoter. W: a woodchuck RNA regulatory element. 3'LTR: an HIV based self inactivating lentiviral 3' LTR.

According to this example, an siRNA lentiviral construct against lacZ gene was constructed by insertion of the siRNA expression cassette into the PacI site of HC-FUGW vector (FIG. 5). HC-FUGW vector (SEQ ID NO: 3) contains a GFP marker gene driven by human Ubiquitin promoter for tracking transduction events. The vector also contains an HIV DNA Flap element to improve the virus titers, and WPRE for high level expression of viral genes. The siRNA expression cassette is composed of a pol III promoter and a small hairpin RNA coding region followed by a pol III terminator site. The pol III promoter is derived from −240 to −8 region of human H1-RNA promoter and is connected to the downstream RNA coding region through a 7 base pair linker sequence to ensure that the transcription is precisely initiated at the first nucleotide of the RNA coding sequence. The small hairpin RNA coding region contains a 19 nt sequence corresponding to 1915-1933 region of the sense strand of lacZ gene coding sequence and the 19 nt perfect reverse complementary sequence separated by a 9 nt loop region. The terminator is comprised of 5 consecutive thymidine residues linked immediately downstream of the RNA coding sequence.

Example 2

Figure 6:
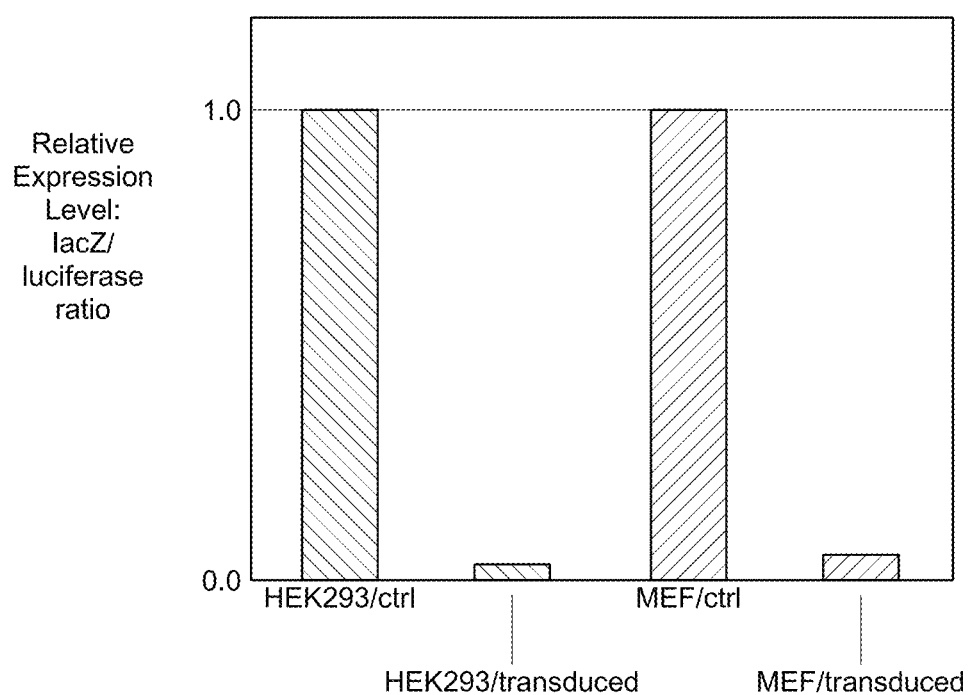
FIG. 6. A lacZ specific siRNA encoded by a lentiviral vector can efficiently inhibit the expression of lacZ reporter gene in virus transduced mammalian cells. MEF: mouse embryonic fibroblasts; HEK293: human embryonic kidney cells. Both of the test cell lines harbor lacZ and firefly luciferase reporter genes, and the expression levels of the reporter genes can be measured by chemiluminescent assays. Ctrl: the ratio of lacZ activity versus Luc activity of the uninfected parental cells, which was arbitrarily set to 1. Transduced: the specific inhibition of lacZ expression calculated as the reduction of lacZ to Luc ratio.

This example demonstrates the transduction of cultured mammalian cells with a retroviral vector (FIG. 6). The retroviral vector encoding a small hairpin RNA molecule described in Example 1, was used to transfect cultured mammalian cells that express lacZ, and caused a profound decrease in the expression of the test gene lacZ. The lacZ siRNA virus was produced by cotransfection of the retroviral vector, a helper virus plasmid (pRSV-Rev) and VSVg expression plasmid in HEK293 cells. The virus particles were harvested from the cell culture supernatants and concentrated by ultracentrifugation. The concentrated virus preparations were used to infect either mouse embryonic fibroblasts (MEF) or HEK293 cells which harbor both lacZ and firefly luciferase (Luc) reporter genes. Infection was monitored by the GFP signal which is expressed from the marker gene cassette of the viral vector. Under the conditions of this experiment, >98% of the test cells were GPF+ and thus successfully transduced. The expression levels of lacZ and Luc reporter genes were measured by chemiluminescent assays using commercially available kits (lacZ assay kit from Roche and Luc from Promega). The lacZ siRNA virus only inhibited the expression of lacZ but not Luc. The specific inhibition was determined by the ration of lacZ activity versus Luc activity. The lacZ/Luc ration of the uninfected parental cells was arbitrarily set to 1 and the values of the infected cells were calculated accordingly. As shown in FIG. 6, transfection with the virus resulted in dramatic reduction in the amount of expression of the lacZ gene in both MEK and HEK293 cells.

Figure 8:
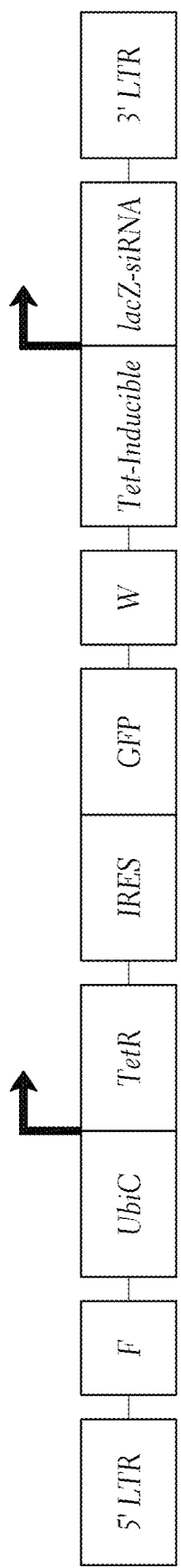
FIG. 8 shows a schematic illustration of a Tet-inducible lacZ siRNA lentiviral vector. A Tet repressor gene (TetR; SEQ ID NO: 7) is the under the control human UbiquitinC promoter and its expression can be monitored by the downstream GFP marker coupled by IRES element (internal ribosomal entry site). The anti-lacZ siRNA cassette is driven by a Tet-inducible pol III promoter derived from human U6-promoter (−328 to +1) containing a single TetR binding site (TetOI) between the PSE and TATA box (SEQ ID NO: 6). In the absence of tetracycline, TetR binds to the promoter and its expression is repressed. Upon the addition of tetracycline, TetR is moved from the promoter and transcription starts.

A tet-inducible lacZ siRNA lentiviral vector was also prepared as illustrated in FIG. 8. A Tet repressor gene (TetR; SEQ ID NO: 7) was placed the under the control of the human UbiquitinC promoter so that its expression could be monitored by the downstream GFP marker. The anti-lacZ siRNA cassette was driven by a Tet-inducible pol III promoter derived from human U6-promoter (−328 to +1) containing a single TetR binding site (TetOI) between the PSE and TATA box (SEQ ID NO: 6). The TetR coding sequence was PCR amplified from genomic DNA from the TOP10 strain of E. coli adn cloned into a modified version of FUIGW as a Bgl2-EcoR1 fragment. In the absence of tetracycline, TetR binds to the promoter and its expression is repressed. Upon the addition of tetracycline, TetR is moved from the promoter and transcription starts.

Figure 9:
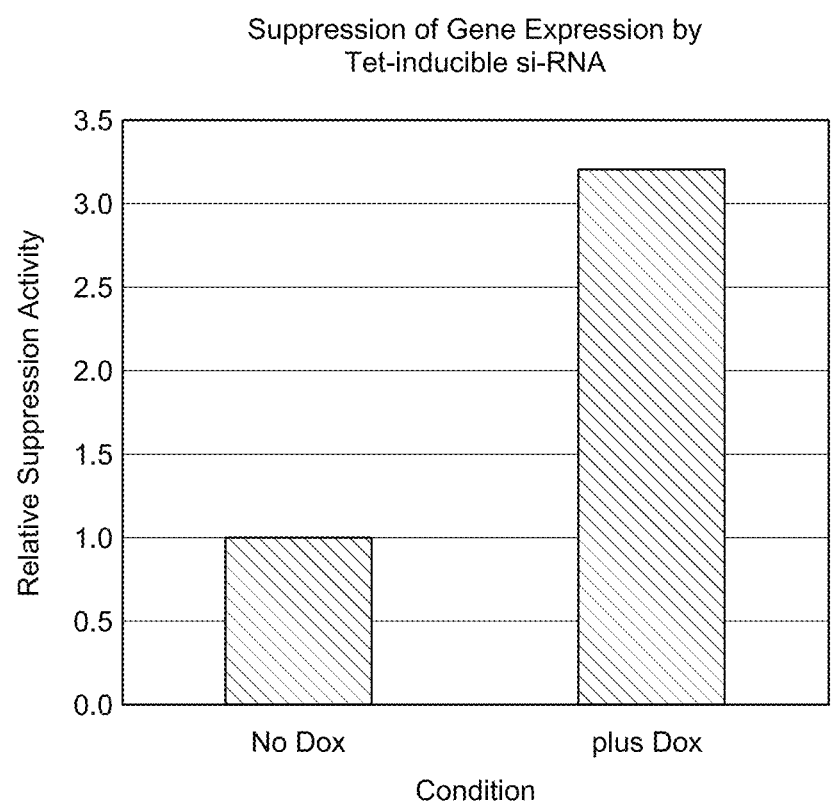
FIG. 9 shows the results of an experiment that demonstrated that a Tet-inducible siRNA expression cassette can regulate gene expression in response to Doxycycline treatment. lacZ and luciferase double expressing HEK293 cells (293Z+Luc) were transduced with lentiviral vector carrying a Tet-inducible lacZ-siRNA cassette and a Tet repressor under the control of a UbiquitinC promoter (FIG. 8). The transduced cells were treated with 10 ug/ml Doxycycline (Plus Dox) for 48 hr or without the Doxycycline treatment as a control (No Dox). LacZ and luciferase activities were measured as described in the previous figures. The relative suppression activity is calculated as the ratio of lacZ versus luciferase and No Dox control was arbitrarily set to 1.

The Tet-inducible siRNA expression cassette was able to regulate gene expression in response to Doxycycline treatment. Virus was prepared from the retroviral construct carrying the Tet-inducible lacZ-siRNA cassette and a Tet repressor under the control of a UbiquitinC promoter and used to transduce HEK293 cells expressing both lacZ and luciferase (293Z+Luc). The transduced cells were treated with 10 ug/ml Doxycycline (Plus Dox) for 48 hr or without the Doxycycline treatment as a control (No Dox). LacZ and luciferase activities were measured as described in the previous figures. The relative suppression activity is calculated as the ratio of lacZ versus luciferase and No Dox control was arbitrarily set to 1. As can be seen in FIG. 9, in the presence of doxycycline suppression of lacZ activity was significantly enhanced.

Example 3

Figure 7:
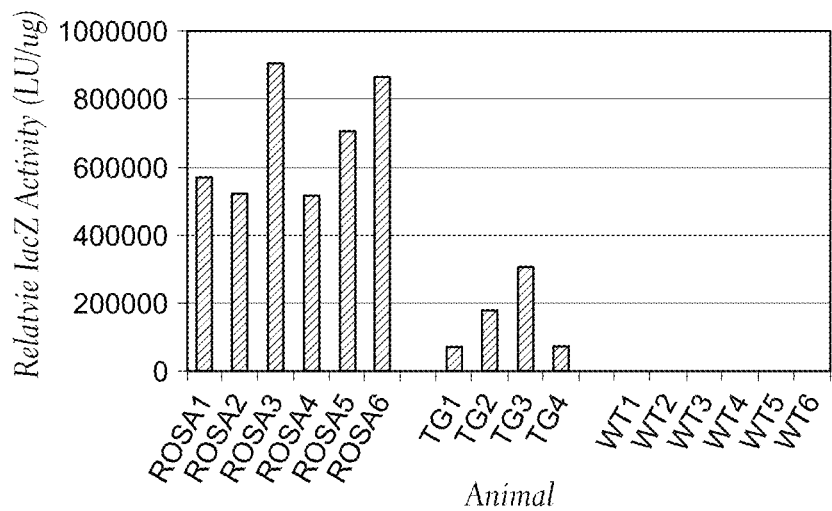
FIG. 7. Transgenic animals that express a lacZ specific siRNA molecule encoded by a lentiviral vector can successfully suppress the expression of the ubiquitous lacZ reporter gene in a ROSA26+/− background. ROSA1-6: the lacZ activities in the limb tissues of six E17.5 ROSA26+/− embryos which served as positive controls. The difference in lacZ activity between individual ROSA26+/− embryos may result from variable protein extraction efficiency. TG1-4: the lacZ activities in the limb tissues of four E17.5 transgenic embryos expressing a lentiviral vector-encoded lacZ siRNA molecule in ROSA+/− background. WT1-6: lacZ activity in the limb tissues of six E17.5 C57Bl/6 wildtype embryos, included as the negative control. The background levels of endogenous beta-galactosidase activity are general below 1,000 LU/ug, thus the columns are not visible.

This example demonstrates the generation of transgenic animals that express an siRNA molecule encoded by a lentiviral vector. The expression of the lacZ specific siRNA construct described in Example 1 resulted in extensive suppression of lacZ activity in ROSA26+/− mice. ROSA26+/− animals carry one copy of an ubiquitously expressed lacZ reporter gene. The lacZ siRNA virus preparations described in Example 2 were used for perivitelline injection of ROSA26+/− single cell embryos obtained from hormone primed C57Bl/6 female donors×ROSA26+/+ stud males. The injected single cell embryos were subsequently transferred into the oviduct of timed pseudopregnant female recipients. Embryonic day 15.5 to 17.5 (E15.5-17.5) fetuses were recovered from the surrogate mothers. Successful transgenesis was scored by positive GFP signal observed with the fetuses under fluorescent microscope. Protein extracts prepared from the limb tissues of the fetuses were used for the LacZ chemiluminescent assay according to the manufacturer's instruction (Roche), and protein concentrations of the tissue extracts were determined by the Bradford assay (BioRad). The lacZ expression levels were expressed as light units (LU) per ug of proteins (LU/ug). The E15.5-17.5 fetuses from the timed mating of C57Bl/6 females× ROSA26+/+ males and C57Bl/6 females×C57Bl/6 males were served as the positive and negative controls respectively. The results are shown in FIG. 7. In animals G1-G4 (those treated with lentiviral vector encoding the siRNA construct), the animals showed markedly decreased expression of the lacZ gene as compared with untreated control animals.

Example 4

Figure 10:
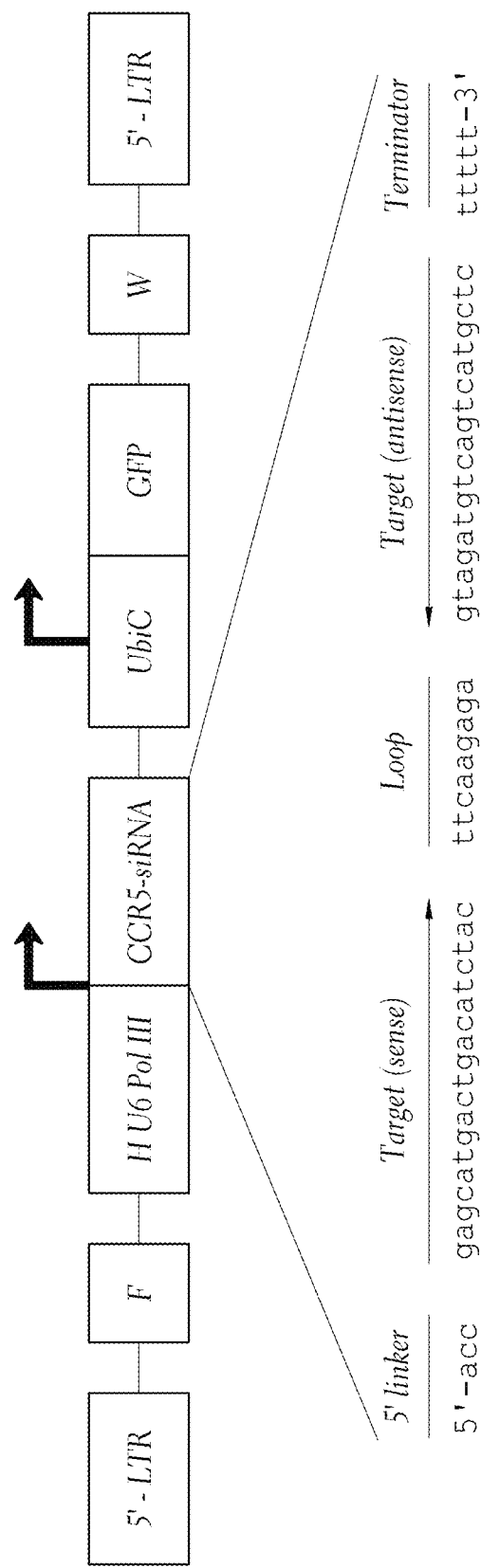
FIG. 10 shows a schematic illustration of an anti-human CCR5 siRNA encoding lentiviral vector. 5'LTR: an HIV based lentiviral vector 5' LTR; F: an HIV Flap element; a human U6-RNA pol III promoter (−328 to +1); siRNA: a human CCR5 specific short hairpin cassette and its structure and detailed sequence are illustrated below. UbiC: an internal human ubiquitinC promoter; GFP: a GFP marker gene driven by UbiC promoter. W: a woodchuck RNA regulatory element. 3'LTR: an HIV based self-inactivating lentiviral 3' LTR.

A lentiviral construct comprising an RNA coding region encoding an anti-human CCR5 siRNA was prepared. As illustrated in FIG. 10, the vector comprised an HIV based lentiviral vector 5' LTR, an HIV Flap element, a human U6-RNA pol II promoter (−328 to +1; SEQ ID NO: 4), a human CCR5 specific short hairpin RNA cassette, an internal ubiquitin promoter, a GFP marker gene operably linked to the ubiquitin promoter a WRE regulatory element and an HIV based self-inactivating lentiviral 3' LTR. The structure and sequence of the anti-CCR5 siRNA are provided in FIG. 10 and SEQ ID NO: 1.

Figure 11:
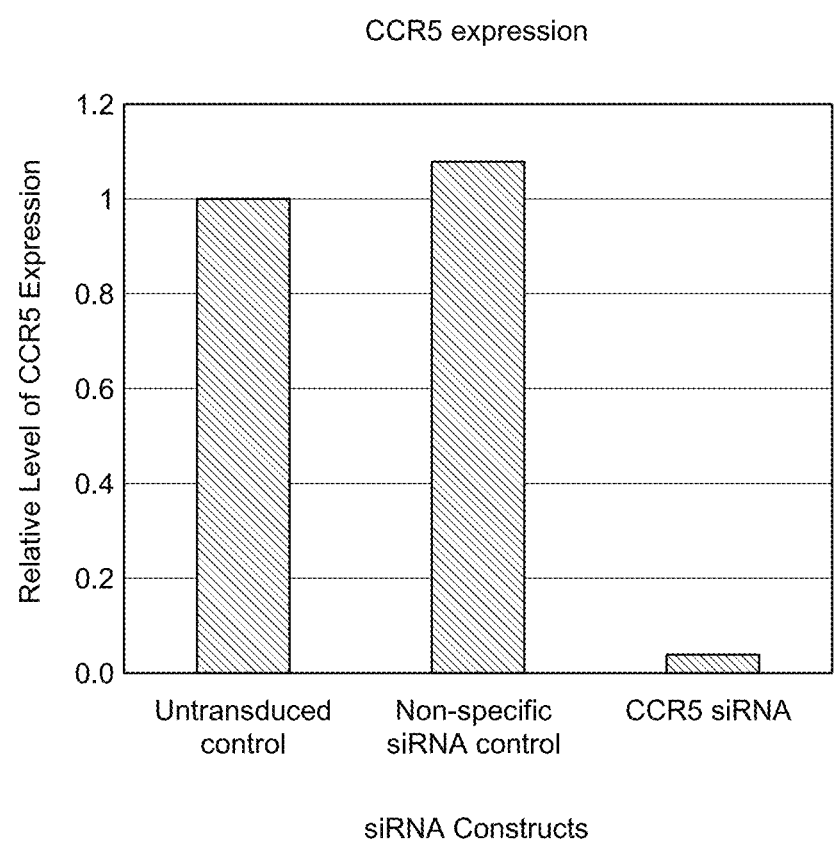
FIG. 11. A anti-human CCR5 specific siRNA encoded by a lentiviral vector can efficiently suppress the expression of CCR5 in transduced human cells. Cell surface expression of CCR5 on transduced or untransduced MAGI-CCR5 (Deng, et al., Nature, 381, 661 (1996)) was measured by flow cytometric analysis (FACS) and the relative expression levels were calculated by mean fluorescence intensity. A non-specific siRNA was also included as a control.

Recombinant retrovirus was prepared from the anti-CCR5 siRNA vector construct as described above. Human MAGI-CCR5 cells (Deng et al., *Nature* 381:661 (1996)) were infected with the recombinant virus or a retrovirus encoding a non-specific control siRNA and cell surface expression of CCR5 was measured by flow cytometric analysis. Relative expression levels were calculated by mean fluorescence intensity. As can be seen in FIG. 11, the anti-CCR5 siRNA reduced the level of CCR5 expression almost completely, while the non-specific siRNA did not suppress expression at all.

Example 5

Figure 12:
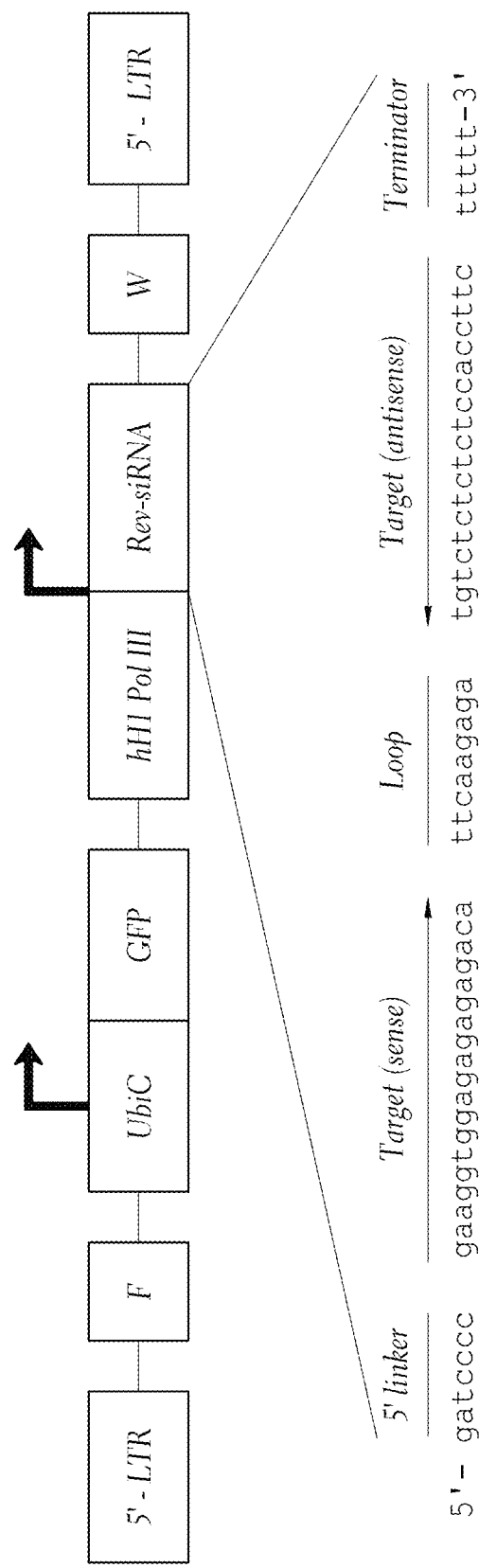
FIG. 12. Schematic illustration of an anti-HIV-1 siRNA encoding lentiviral vector. 5'LTR: an HIV based lentiviral vector 5' LTR; F: an HIV Flap element; a human H1-RNA pol III promoter (−240 to −9); siRNA: a HIV-1 Rev gene specific short hairpin cassette and its structure and detailed sequence are illustrated below. UbiC: an internal human ubiquitinC promoter; GFP: a GFP marker gene driven by UbiC promoter. W: a woodchuck RNA regulatory element. 3'LTR: an HIV based self inactivating lentiviral 3' LTR.

A further anti-HIV-1 siRNA encoding lentiviral vector was constructed, as illustrated in FIG. 12. This vector comprised an RNA coding region encoding an anti-HIV-1 Rev gene specific short hairpin siRNA (SEQ ID NO: 2). The anti-HIV-1 Rev siRNA targeted the 8420 to 8468 region of the Rev coding of HIV-1 (nucleotide coordinate of NL4-3 strain; Salminen et al. Virology 213:80-86 (1995)). The sequence and structure of the siRNA coding region are illustrated in FIG. 12 as well. Expression of the anti-HIV-1 Rev siRNA was driven by a human H1-RNA pol III promoter (−240 to −9; SEQ ID NO: 5).

The ability of the anti-HIV-1 Rev siRNA to suppress HIV transcription in human cells was measured. The transcriptional activity of HIV-1 was measured based on the activity of a firefly luciferase reporter gene inserted at the env/nef region, essentially as described in Li et al. J. Virol. 65:3973 (1991)).

Recombinant retrovirus was prepared from the vector construct as described above and used to infect human cells comprising HIV-1 with the reporter construct. The luciferase activity of untransduced parental cells was arbitrarily set to 1 and the relative HIV transcription levels of the transduced cells were calculated accordingly. A non-specific siRNA was used as a control.

Figure 13:
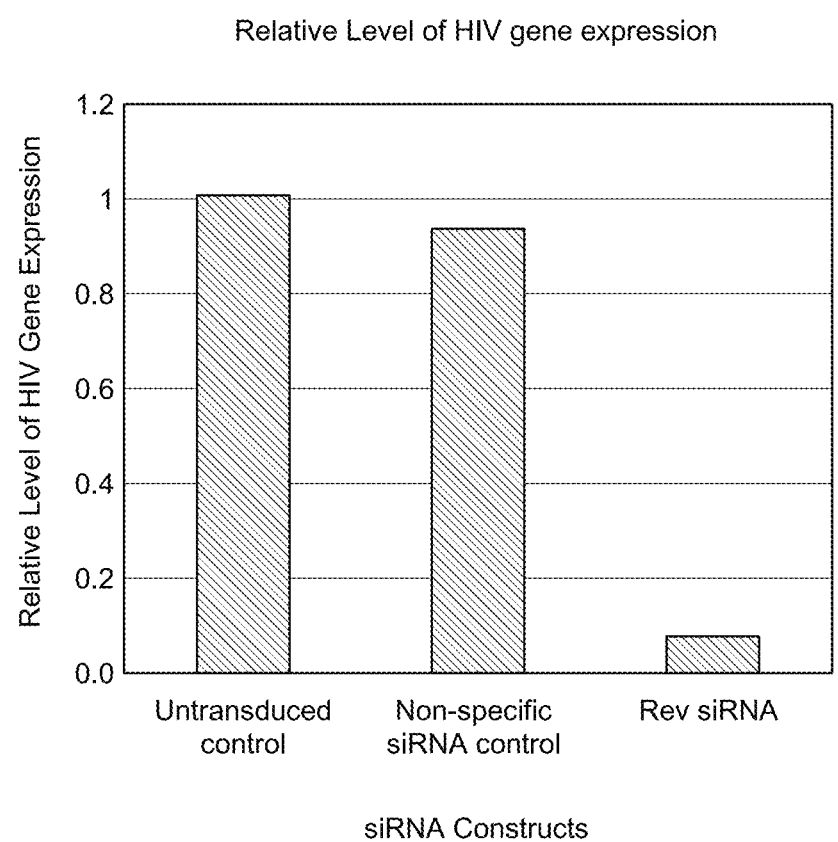
FIG. 13 demonstrates that an anti-HIV-1 Rev gene specific siRNA encoded by a lentiviral vector can efficiently suppress the expression of HIV transcription in human cells. The transcription activity of HIV-1 virus is measured a firefly luciferase reporter gene inserted at the env/nef region (Li, et al J Virol., 65, 3973 (1991)). The luciferase activity of the untransduced parental cells was arbitrarily set to 1 and the relative HIV transcription levels of the transduced cells were calculated accordingly. A non-specific siRNA containing vector was included as a control.

As can be seen in FIG. 13, HIV-1 transcription was significantly suppressed in cells infected with the recombinant retrovirus comprising the anti-HIV-1 Rev siRNA coding region, while the non-specific siRNA had no significant effect.

Example 6

According to this example, an siRNA lentiviral construct against the HIV genome is constructed by insertion of an siRNA expression cassette into the PacI site of HC-FUGW vector. HC-FUGW vector contains a GFP marker gene driven by human Ubiquitin promoter for tracking transduction events. The vector also contains an HIV DNA Flap element to improve the virus titers, and WPRE for high level expression of viral genes. The siRNA expression cassette is composed of a pol III promoter and a small hairpin RNA coding region followed by a pol III terminator site. The pol III promoter is derived from −240 to −8 region of human H1-RNA promoter and is connected to the downstream RNA coding region through a 7 base pair linker sequence to ensure that the transcription is precisely initiated at the first nucleotide of the RNA coding sequence. The small hairpin RNA coding region contains a 21 nt sequence corresponding to a region of the CCR5 coding sequence and the 21 nt perfect reverse complementary sequence separated by a 4 nt loop region. The terminator is comprised of 5 consecutive thymidine residues linked immediately downstream of the RNA coding sequence.

The retroviral construct is used to transfect a packaging cell line (HEK293 cells) along with a helper virus plasmid and VSVg expression plasmid. The recombinant viral particles are recovered.

CD34-positive hematopoietic stem cells are isolated from a patient's bone marrow using a immunomagnetic approach (see, for example, Choi et al. (1995) Blood 85:402-413; Fehse et al. (1997) Human Gene Therapy 8:1815-1824; Di Nicola et al. (1996) Bone Marrow Transplant. 18:1117-1121; Servida et al. (1996) Stem Cells 14:430-438; de Wynter et al. (1995) Stem Cells 13:524-532; Ye et al. (1996) Bone Marrow Transplant. 18:997-1008.). The cells are cultured and treated with the recombinant virus particles. The infected cells are sorted by FACS based on expression of GFP. Those cells expressing GFP are reintroduced into a patient by injection.

Example 7

Figure 14:
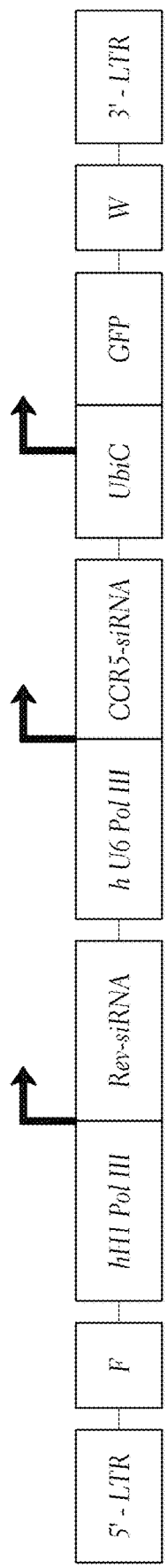
FIG. 14 shows a schematic diagram of a bivalent retroviral vector carrying both anti-HIV Rev and anti-human CCR siRNA expression cassettes. Symbols are the same as depicted in the previous figures.

According to this example, an siRNA lentiviral construct against the HIV genome is constructed by insertion of an siRNA expression cassette into the PacI site of HC-FUGW vector. The siRNA expression cassette comprises a human H1 promoter operatively linked to an RNA coding region encoding an anti-HIV-1 Rev gene specific short hairpin siRNA. The siRNA expression cassette additionally comprises a pol III promoter operatively linked to a small anti-CCR5 hairpin RNA. The retroviral construct is illustrated in FIG. 14.

The retroviral construct is used to transfect a packaging cell line (HEK293 cells) along with a helper virus plasmid and VSVg expression plasmid. The recombinant viral particles are recovered.

CD34-positive hematopoietic stem cells are isolated from a patient's bone marrow using a immunomagnetic approach (see, for example, Choi et al. (1995) Blood 85:402-413; Fehse et al. (1997) Human Gene Therapy 8:1815-1824; Di Nicola et al. (1996) Bone Marrow Transplant. 18:1117-1121; Servida et al. (1996) Stem Cells 14:430-438; de Wynter et al. (1995) Stem Cells 13:524-532; Ye et al. (1996) Bone Marrow Transplant. 18:997-1008.). The cells are cultured and treated with the recombinant virus particles. The infected cells are sorted by FACS based on expression of GFP. Those cells expressing GFP are reintroduced into a patient by injection.

Example 8

Virus production from the lentiviral vector carrying the anti-HIV-1 Rev siRNA expression cassette, as described in Example 6, was tested by co-transfecting 293T cells with the lentiviral vector, a packaging plasmid (pRSV-Rev; Dull, T. et al. J Virol. 72(11): 8463-8471 (1998)) comprising the wild type Rev sequence (SEQ ID NO: 11) and a VSVg expression plasmid. The ability to increase virus production was tested by use of a mutant form of the pRSV-Rev packaging plasmid that is resistant to Rev-siRNA mediated degradation. In this plasmid the mutant Rev nucleotide sequence (SEQ ID NO:

12) comprises two silent mutations that make the Rev mRNA resistant to siRNA mediated degradation, but do not alter the amino acid sequence. In addition, the effect on virus production of expression of one or more siRNA that inhibit RNA interference was tested.

Figure 15:
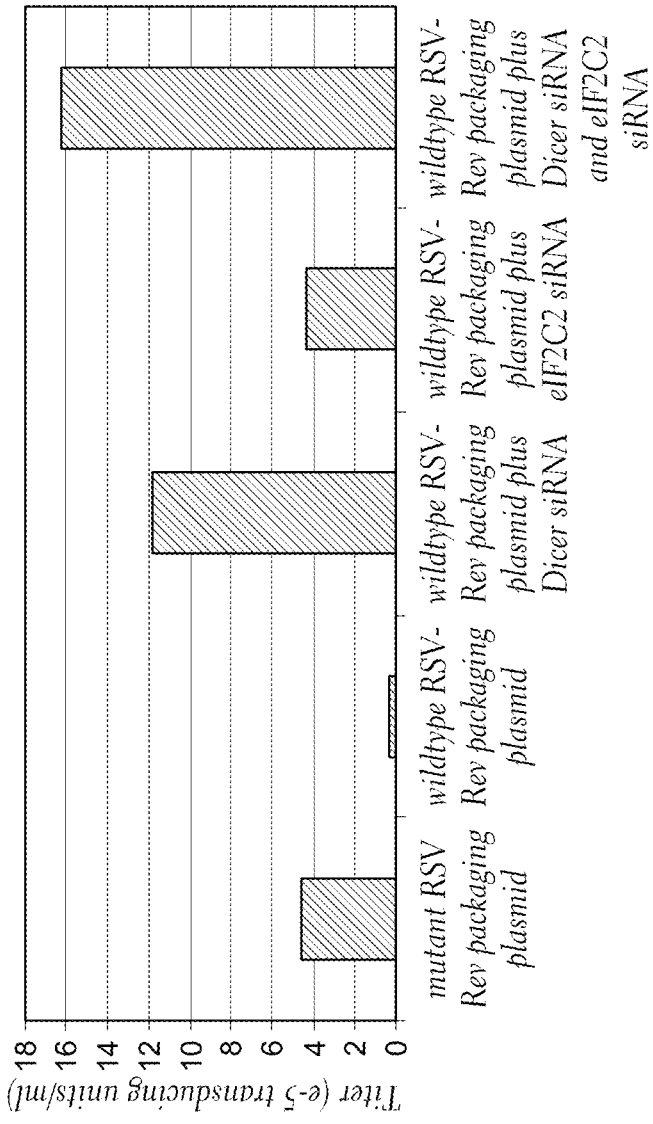
FIG. 15 shows virus production from lentiviral vector comprising the anti-Rev siRNA expression cassette after cotransfection with wild type pRSV-Rev packaging plasmid, mutant pRSV-Rev that is resistant to Rev-siRNA mediated degradation, or wild type pRSV-Rev in the presence of anti-Dicer, anti-eIF2C2 or anti-Dicer and anti-eIF2C2 siRNAs.

Cells were cotransfected with either wild-type pRS V-Rev alone, the mutant form of pRSV-Rev, wild-type pRSV-Rev plus a plasmid that drives expression of anti-Dicer-1 siRNA (SEQ ID NO: 8), wild-type pRSV-Rev plus a plasmid that drives expression of anti-eIF2C2 siRNA (SEQ ID NO: 9), or the wild-type pRSV-Rev plus a plasmid that drives expression of anti-Dicer siRNA and anti-eIF2C2 siRNA. Anti-Dicer-1 and anti-eIF2C2 siRNA expression was under the control of the human H1-RNA pol III promoter (−241 to −9; SEQ ID NO: 10). As can be seen in Table 1 and FIG. 15, virus titer was greatest from 293T cells transfected with pRSV-Rev in the presence of anti-Dicer siRNA and the combination of anti-Dicer siRNA and anti-eIF2C2 siRNA.

TABLE 1

| Transfection | Titer (e-5 TU/ml) |
| --- | --- |
| wild-type pRSV-Rev plasmid | 0.34 |
| mutant pRSV-Rev packaging plasmid | 4.6 |
| wild-type pRSV-Rev plasmid + anti-Dicer-1 siRNA | 11.8 |
| wild-type pRSV-Rev plasmid + anti-eIF2C2 siRNA | 4.5 |
| wild-type pRSV-Rev plasmid + anti-Dicer-1 siRNA + anti-eIF2C2 siRNA | 16.3 |

A packaging cell line that stably expresses both anti-Dicer-1 (SEQ ID NO: 8) and anti-eIF2C2 (SEQ ID NO: 9) siRNAs was created. 293 cells were transfected with a pcDNA4 (Invitrogen) vector comprising anti-eIF2C2 and anti-Dicer expression cassettes as well as a Zeocin resistance gene for drug selection.

Examples 9-11

Experimental Methods

The following experimental methods were used for Examples 9-11 described below.

Construction of CCR5 shRNA Library

A random shRNA library directed to human CCR5 sequences was generated by adapting the method of enzymatic production of RNAi libraries from cDNAs (EPRIL) (D. Shirane et al., Nat. Genet. 36, 190-196 (2004)). Human CCR5 cDNA was PCR amplified from pBABE.CCR5 plasmid DNA (NIH AIDS research and reference reagent program) using primer pairs (5'GATGGATTATCAAGTGT-CAAGTCCA3')(SEQ ID NO: 22); 5'GTCACAAGCCCACAGATATTTCC3')(SEQ ID NO: 23) and KOD hot start DNA polymerase (Novagen). The CCR5 cDNA was partially digested by DNAseI (Qiagen) to generate 100-200 bp DNA fragments. DNA fragments were ligated to a hairpin adapter 1 (Ad1) DNA linker containing a MmeI restriction enzyme site (5' GTCGGACAAT-TGCGACCCGCATGCTGCGGGTCGCAAT-TGTCCGAC3') (SEQ ID NO: 24). The ligated DNA fragments were then treated with T4 DNA polynucleotide kinase (NEB) followed by E. coli DNA ligase treatment (NEB) to fill in a nick between the 5' end of Ad1 and 3' end of CCR5 DNA fragments. The Ad1 ligated DNAs (~40 nt) were digested with MmeI (NEB), and purified from a native PAGE gel. The purified DNA fragments were ligated to an adapter 2 (Ad2) linker (+ strand, 5'GGG-GATCCCTTCGGTACTCCAGACCGTGAGTC3')(SEQ ID NO: 25) (− strand 5'TACCGAAGGGATCCCCNN3') (where N is any nucleotide in the respective position)(SEQ ID NO: 26) and purified from a native PAGE gel. The purified DNA fragments were treated with T4 polynucleotide kinase (NEB) and T4 DNA ligase (NEB) to fill a nick. The Ad2 ligated DNA fragments were subjected to a primer extension reaction using primer (5'GACTCACGGTCTG-GAGTACCGAAG3')(SEQ ID NO: 27) and Bst DNA polymerase large fragment (NEB) and the resulting products purified from a PAGE gel. The purified DNA fragments were digested with BpmI, blunt ended with Klenow fragment (NEB), digested with BamHI, and ligated to pBShH1-5 plasmid DNA which contains an human H1 RNA polymerase III promoter and 4T termination signal. The ligation mixture was introduced into E. coli (XL1 blue) by electroporation and plated on 2×YT agar plate with 10 ug/ml of carbenicillin overnight. Approximately 8000 colonies were combined and plasmid DNAs were prepared. The plasmid DNAs were digested with BcgI, blunt ended with T4 DNA polymerase (NEB) and religated to remove excess DNA sequences. The religated plasmid DNAs were further treated with MfeI to eliminate contamination of BcgI incompletely digested plasmids and used to transform E. coli. Twenty clones of the plasmid DNA were sequenced to confirm the randomness of shRNA sequences targeting CCR5. After sequence confirmation, shRNA expression units consisting of an H1 promoter, shRNA sequence and 4 Ts termination signal were excised from the pBShH1-5 plasmid DNAs by XbaI and XhoI digestion and inserted into XbaI/XhoI sites of the FG12 lentiviral vector (X. F. Qin, D. S. An, I. S. Chen, D. Baltimore, Proc. Natl. Acad. Sci. U.S.A 2003. January 7; 100(1):183-8. 100, 183-188 (2003)). This procedure was also done for rhesus CCR5.

Lentiviral Vector Production and shRNA Library Screening.

Four hundred clones of vesicular stomatitis virus (VSV)-G pseudotyped lentiviral vector were individually produced in 293T cells in 96 well plates. Vector supernatant from each well was harvested at 48 hour post transfection and used to infect CCR5NKRCEM cells in 96 well plates. Reduction of CCR5 expression in EGFP+ cells was analyzed at 3 days post infection by monoclonal staining against human CCR5 (2D7 APC, BD Biosciences) and flow cytometric analysis. siRNAs were identified by their ability to reduce CCR5 expression.

shRNAs Against Human and Rhesus CCR5

Of the siRNAs identified, the human shRNA indicated as (hu1005) and the corresponding rhesus (rh1005) shRNAs directed to CCR5 were found to have particularly desirable properties as described below. The human CCR5 shRNA (hu1005) sequence (RNA) is shown in SEQ ID NO: 17. The target sequence of human CCR5-shRNA (hu1005) identified from a shRNA library screening is 5'GAGCAAG-CUCAGUUUACACC3' (SEQ ID NO: 16); while the human CCR5 shRNA (hu1005) sequence in plasmid DNA is shown in SEQ ID NO: 18. The rhesus CCR5 shRNA (rh1005) sequence (RNA) is shown in SEQ ID NO: 20. The corresponding rhesus shRNA CCR5 (rh1005) target sequence in rhesus CCR5mRNA is 5'GAGCAAGUUCAGUUUA-CACC3' (SEQ ID NO: 19; the rhesus CCR5 shRNA (1005) sequence in plasmid DNA is shown in SEQ ID NO: 21. A rhesus CCR5 shRNA expression unit was generated by inserting hybridized oligo DNAs (sense 5'gatccccGAGCAAGTTCAGTTTACACC-TTGTCCGAC-GTGTAAACTGAACTTGCTC-TTTTTc-3') (SEQ ID NO: 28) (anti sense 3'-gggCTCGTTCAAGTCAAATGTGG-AACAGGCTG-CCACATTTGACTTGAACGAG-AAAAAGAGCT-5') (SEQ ID NO: 29) into pBShH1-3 plasmid DNA (X. F. Qin, D. S. An, I. S. Chen, D. Baltimore, Proc. Natl. Acad. Sci. U.S.A 2003. January 7; 100(1):183-8. 100, 183-188 (2003)). The rhCCR5 shRNA sequence was confirmed by sequencing.

The target sequence of CCR5-shRNA(hu13)(SEQ ID NO: 13) which was used for comparison purposes has been previously described (D. S. An et al., Mol. Ther. 14, 494-504 (2006), hereby incorporated by reference in its entirety). The human CCR5 shRNA (hu13) sequence (RNA) is shown in SEQ ID NO: 14, while the human CCR5 shRNA (hu13) sequence in plasmid DNA is shown in SEQ ID NO: 15.

SIVmac251 Based Lentiviral Vector Construction

To insert a rhCCR5 shRNA expression unit into a SIV based vector for in vitro transduction studies, XbaI and XhoI sites were created by an oligo DNA insertion into a ClaI site in pSIV-R4SAW10, which is derived from pSIV-games4 (P. E. Mangeot et al., J. Virol. 74, 8307-8315 (2000); P. E. Mangeot et al., Mol. Ther. 5, 283-290 (2002)). The rhCCR5 shRNA expression unit was excised from pBShH1-3 by XbaI and XhoI digestion and inserted into the XbaI and XhoI site of pSIV-R4SAW10. To construct a SIV vector for animal transplant studies, a SacII/XhoI DNA fragment was inserted containing the RhMLV RNA polymerase II promoter sequence excised from pCS-Rh-MLV-E plasmid DNA (S. Kung, An D. S., Chen I. S. Y., J. Virol. 74, 3668-3681 (2000)) into the ClaI/S all sites of the SIV vector (pSIV-RMES GAE) using an oligo DNA linker (+ strand 5'CGATACCCTAGGACGGCTGACGC3')(SEQ ID NO: 30)-strand 5'GTCGACCGTCCTAGGGTAT3')(SEQ ID NO: 31)(P. E. Mangeot et al., Mol. Ther. 5, 283-290 (2002)). This resulted in vector pSIV GAE RhMLV-E. EGFP expression has been shown to be efficiently expressed in non-human primate lymphocytes using the RhMLV promoter (S. Kung, An D. S., Chen I. S. Y., J. Virol. 74, 3668-3681 (2000)). An XbaI/XhoI digested DNA fragment containing an H1 promoter-shRNA expression unit was inserted into the AvrII and SalI sites in front of the RhMLV promoter of the pSIV-GAE RhMLV-E vector, resulting in the final pSIV GAE rhCCR5 shRNA RhMLV-E vector.

Lentiviral Vector Transduction

VSV-G pseudotyped retroviral/lentiviral vector stocks were produced by calcium phosphate-mediated transfection of HEK-293 T cells. Briefly, HEK-293 T cells were cultured in Iscove's modified Eagle's medium containing 10% FCS, 100 units of penicillin, and 100 µg/ml streptomycin. The pBabe-rhCCR5 retroviral vector was produced by co-transfecting vector plasmid, the MLV packaging plasmid (pSV-psi-env-MLV)(Landau N R and Littman D R, J. Virol 66, 5110-5113 (1992)) and the VSV-G expression plasmid (pHCMVG)(J. K. Yee, T. Friedmann, J. C. Burns, Methods Cell Biol. 43 Pt A:99-112, 99-112 (1994)). HIV vectors were produced by co-transfecting vector plasmid, the HIV-1 lentiviral packaging plasmids pRSVREV and pMDLg/pRRE (T. Dull et al., J. Virol. 72, 8463-8471 (1998)). The pHCMVG SIV based vector was produced by co-transfecting SIV vector, SIV packaging vector pSIV15, pGREV, pSI-k-VPX plasmid DNAs into HEK 293T cells by Calcium Phosphate transfection as described (P. E. Mangeot et al., Mol. Ther. 5, 283-290 (2002)). Virus culture supernatants were harvested at day 2 post-transfection and concentrated 300-fold by ultracentrifugation. The concentrated virus stocks were titrated on HEK-293 T cells based on EGFP expression.

Cells rhCCR5-293T was created by infecting HEK-293T cells with a VSV-G pseudotyped pBabe-rhCCR5 retroviral vector followed by puromycin selection (1 ug/ml). CCR5-NKR-CEM was obtained from the NIH AIDS reagents program.

Human primary peripheral blood mononuclear cells were isolated from leukopack by Ficoll-Paque™ PLUS (GE healthcare life sciences). Rhesus primary peripheral blood mononuclear cells were isolated from peripheral blood by Ficoll-Paque™ PLUS.

Rhesus Macaque Cell Transduction and Transplant

Animals used were colony-bred rhesus macaques (Macaca mulatta) maintained and used in accordance with guidelines of the National Institutes of Health Guide for the Care and Use of Laboratory Animals (Department of Health and Human Services [DHHS] publication no. NIH85-23). The protocol was approved by the Animal Care and Use Committee of National Heart, Lung, and Blood Institute, NIH/DHHS. The animals were free of specific pathogens (serologically negative for simian T-lymphotropic virus, simian immunodeficiency virus, simian retrovirus, and herpesvirus B).

CD34+ hematopoietic stem/progenitor cells were mobilized into the peripheral blood (PB) and purified as described (W. E. Sander et al., J. Nucl. Med. 47, 1212-1219 (2006)). The PB CD34+ cells from two animals ($7\times10^7$ and $1\times10^8$ for animals RQ3570 and RQ5427, respectively) were transduced ex vivo with the VSV-G pseudotyped SIV rhCCR5 shRNA RhMLV-E vector at an moi of 2.4 once a day for 2 days in the presence of SCF (50 ng/ml) and IL6 (50 ng/ml) in X-Vivo 10 Serum Free Medium (BioWhittaker) with Gentamicin (50 ug/ml, Cambrex Bio Science). Transduction efficiency was analyzed by quantitating EGFP expression by flow cytometry 64 hour post first transduction. 18% and 7.4% of the cells were EGFP positive for animals RQ3570 and RQ5427, respectively. The two animals received autologous transplants with $1.6\times10^8$ transduced PB CD34+ cells. All animals received 10 Gy of total-body gamma-irradiation as a 5-Gy fractionated dose given on 2 consecutive days before transplantation (days −1 and 0, with day 0 being the date of reinfusion) and supported with antibiotic, blood, and fluid support accordingly.

Monoclonal Antibodies and Staining Procedures and Flow Cytometric Analysis.

A whole blood staining method was used to detect CCR5 on the cell surface by monoclonal antibodies in peripheral blood lymphocytes (B. Lee, M. Sharron, L. J. Montaner, D. Weissman, R. W. Doms, Proc. Natl. Acad. Sci. U.S.A. 96, 5215-5220 (1999)). Briefly, EDTA treated whole blood was centrifuged and plasma was removed. 50 µl of packed blood was mixed with monoclonal antibodies and stained at room temperature for 30 min, followed by ammonium chloride mediated red blood cell lysis and fixed with 2% formaldehyde in PBS. For the staining of ex vivo PHA/IL2 stimulated cells, the cells ($1\times10^5$) were mixed with 5 µl of anti-CCR5 monoclonal antibodies (2D7 for human) (3A9 for rhesus) in 100 µl of PBS in 2% FCS, incubated at room temperature for 30 min, washed with PBS with 2% FCS, fixed with 2% formaldehyde in PBS. The monoclonal antibodies used for this study included: anti-human CCR5 (2D7 APC, 556903, BD Biosciences), rhesus CCR5 (3A9 APC, 550586, BD Biosciences), CD4 PerCP (550631, BD Biosciences), CD8PE (555367, BD Biosciences), CXCR4 PE (555974, BD Biosciences), CD45RO PE-Cy7 (337167, BD Biosciences), CD95 PE (556641, BD Biosciences). The stained cells were analyzed by a FACS calibur (BD Biosciences) or a Cytomics FC500 (Beckman Coulter).

Cell Sorting

Peripheral blood derived mononuclear cells were isolated by Ficoll-Paque™ PLUS (GE Healthcare Life Sciences) and EGFP+ and EGFP− lymphocyte populations were isolated by FACS Aria cell sorter (BD Biosciences). The sorting purities of EGFP+ and EGFP− population were 92% and 96%, respectively, as determined by flow cytometric analysis of the sorted cells.

Small RNA Isolation

The small RNA fraction was isolated from PHA/IL2 stimulated rhesus monkey peripheral blood lymphocytes (~4×10$^8$ cells) at day 9 post-stimulation using PureLink™ miRNA isolation kit (Invitrogen) according to the manufacturer's instructions.

Northern Blot Analysis of siRNA

Twenty five micrograms of fractionated small RNA were resolved on a 15% urea-acrylamide-TBE gel (SequaGel; National diagnostics) and electrotransferred to nylon membrane (GeneScreen Plus; NEN) at 80 volts 1 hr in 0.5×TBE. The membrane was dried, UV cross-linked, and baked at 80° C. for 1 hr. Oligonucleotide probes (sense: GAG CAA GTT CAG TTT ACA CC (SEQ ID NO: 32); anti sense: GGT GTA AAC TGA ACT TGC TC)(SEQ ID NO: 33) were labeled using Starfire oligos kit (Integrated DNA Technologies) and α-$^{32}$P dATP (6000 Ci/mmol, PerkinElmer) according to the manufacturer's instructions. The probes were hybridized to the membranes at 37° C. in ULTRAhyb™-Oligo (Ambion) overnight. The membrane was washed 3 times for 15 min at 37° C. in 2×SSC, 0.1% SDS. Signal detection and analysis of Northern blots was performed by exposing the blots to phosphorimaging plates followed by analysis on a phosphorimager (Storm system; Molecular Dynamics) using synthetic rhCCR5 siRNA (GGU GUA AAC UGA ACU UGC UC (SEQ ID NO: 34); Sigma-Proligo) as a standard.

Real Time RT-PCR Analysis

Published primer pairs and probes were utilized to detect rhesus CCR5 mRNA and β2 microglobulin (J. J. Mattapallil et al. 434, 1093-1097, Nature, (2005)). Total RNA (100 ng) was isolated from sorted EGFP+ or EGFP− rhesus PBL by Trizol Reagent (Invitrogen) and subjected to RT PCR reaction using Qiagen one step RT-PCR kit and the following conditions (50C, 30 min and 55 C, 10 min for RT reaction, 95C, 15 min for RT inactivation and activation of HotStar-Taq DNA Polymerase, 50 cycles of 95C, 15 sec, 55C, 30 sec and 60 C, 90 sec for PCR). RNA standards for CCR5 and β2 microglobulin mRNA quantitation were made by serial dilution of in vitro transcribed rhesus CCR5 and β2 microglobulin RNAs using T7 RNA polymerase (MEGAscript T7, Ambion).

RT-PCR Analysis of siRNA

A real time stem-loop RT-PCR method was used to quantitate the levels of the antisense strand of siRNA against rhesus CCR5 (C. Chen et al., *Nucleic Acids Res.* 33, e179 (2005)). Total RNA (500 ng) was isolated from rhesus PBL by Trizol Reagent (Invitrogen) and subjected to RT reaction (16C 30 min, 42C 30 min, 85C 5 min), followed by PCR (95C 10 min 1 cycle. 95C 15 sec and 58 C 1 min, 50 cycles). Primer and probe sequences are as follows. RT stem loop primer: 5' GTCGTATCCAGTGCAGGGTCCGAGGTAT-TCGCACTGGATACGACAAGAGCAA3' (SEQ ID NO: 35). Forward primer: 5'GCGCGGTGTAAACTGAAC3' (SEQ ID NO: 36). Reverse primer: 5'GTGCAGGGTCCGAGGT (SEQ ID NO: 37); probe: 6-FAM-TGGATACGACAAGAGCAA-MGB (SEQ ID NO: 38). A set of serial diluted synthetic 22 nt antisense strand of siRNA against rhCCR5 (GGU GUA AAC UGA ACU UGC UC; Sigma-Proligo)(SEQ ID NO: 39) was used as standards for quantitation.

SIV Production and Infection

Sorted EGFP+ or EGFP− rhesus PBL were stimulated with PHA (5 ug/ml, Sigma) and IL2 (concentration) for 2 days. PHA was then removed and the cells were stimulated with IL2 for another 2 days. The cells (1×10$^5$) were infected with 100 ul of SIVmac239 (moi of 0.04) for 1 hour at 37 C, washed 2 times with PBS with 2% FCS, washed 1 time with medium and resuspended in RPMI 20% FCS with IL2 and cultured.

The virus produced was propagated in CEMX174 cells. The 5' and 3' halves of SIVmac239 plasmid DNAs linearized by SphI digestion were transfected into HEK 293T cells. Infectious titer of virus stocks (4×10$^4$ infectious unit/ml) (p27 value=72 ng/ml) was determined on MAGI CCR5 cells as described (B. Chackerian, E. M. Long, P. A. Luciw, J. Overbaugh, J. Virol. 71, 3932-3939 (1997)).

ELISA

The levels of SIV p27 core antigen in SIV infected culture supernatant were measured using COULTER SIV core antigen assay according to the manufacturer's instructions (cat #6604395, Beckman Coulter).

Example 9

A random library of shRNA directed to human CCR5 sequences was screened, and one siRNA comprising a target sequence was identified (labeled CCR5shRNA (hu1005)) (SEQ ID NO: 16) that had no obvious toxicities in human peripheral blood mononuclear cells (PBMC) and was the most potent at inhibiting CCR5 among shRNAs characterized to date, as shown in FIGS. 16A-B. Unlike potent shRNAs previously described (D. S. An et al., Mol. Ther. 14, 494-504 (2006)), expression of this siRNA (SEQ ID NO: 17) did not alter the growth kinetics of transduced T-lymphocytes over a 12-day period of culture.

CEM-NKR-CCR5 cells were transduced with lentiviral vectors expressing random shRNAs against human CCR5 in 96 well plates, cultured for 3 days and analyzed by flow cytometry for CCR5 expression in a GFP-expressing population. Among the 400 shRNAs screened, shRNA (hu1005) (SEQ ID NO: 17) reduced CCR5 more efficiently than a previously published shRNA (hu13) (SEQ ID NO: 14), as shown in FIG. 16A. FIG. 16B shows data indicating efficient reduction of endogenous CCR5 expression in human primary lymphocytes (huPBL). PHA/IL2 activated huPBL were transduced with lentiviral vectors bearing shRNA (hu1005)(SEQ ID NO: 17) and analyzed 8 days post-infection by monoclonal antibody staining and flow cytometry for CCR5 expression in GFP+ population. The percentage of CCR5 expression in the GFP+ population was calculated and indicated on the top of each panel. As depicted in FIGS. 16-17, the label "Mock" indicates no vector transduction. The label "No shRNA" indicates vector transduction without shRNA expression Example 10

Figure 17A:
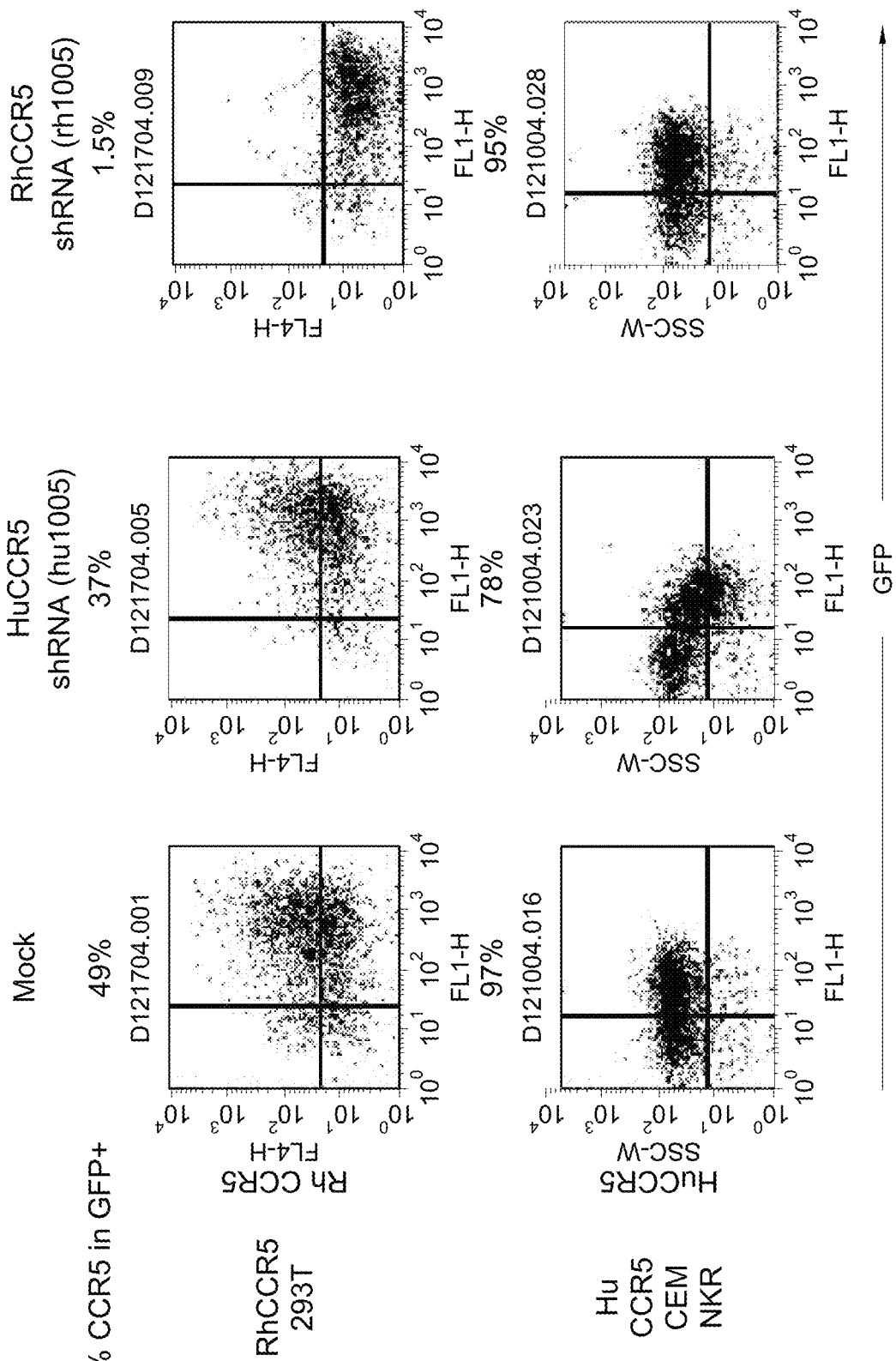
FIG. 17A illustrates the results of a study in which an shRNA against rhesus CCR5 (rh1005)(SEQ ID NO: 20) was tested in rhCCR5 expressing 293T cells. The function and safety of this shRNA was tested by transducing peripheral blood mobilized rhesus CD34+ cells followed by autologous transplant into myeloablated animals. Cells were transduced with a SIV based lentiviral vector bearing shRNA (rh1005) against rhCCR5 and analyzed for CCR5 and GFP expression by monoclonal antibody staining and flow cytometry at 4 days post transduction. As shown, the rhCCR5 shRNA (rh1005) reduced rhCCR5 expression in rhCCR5-293T cells but did not reduce human CCR5 expression in human CCR5 expressing CCR5NKRCEM cells due to a single nucleotide mismatch in target sequence, as shown. Similarly, huCCR5 shRNA reduced human CCR5 expression, but not rhesus CCR5 expression.

In this example, an shRNA against rhesus CCR5 (rh1005) (SEQ ID NO: 20) was tested in rhCCR5 expressing 293T cells. The rhesus CCR5 (rh1005) shRNA (SEQ ID NO: 20) differs from the human CCR5 (hu1005) by two nucleotides; there is a single nucleotide difference in each sense strand and antisense strand of the shRNA. The rhesus macaque hematopoietic stem cell transplant model is arguably the closest model to that of hematopoietic stem cell transplant in humans. Cells were transduced with a SIV based lentiviral vector bearing shRNA (1005)(SEQ ID NO: 20) against rhCCR5 and analyzed for CCR5 and GFP expression by monoclonal antibody staining and flow cytometry at 4 days post transduction. As shown in FIG. 17A, the rhCCR5 shRNA reduced rhCCR5 expression in rhCCR5-293T cells but, did not reduce human CCR5 in human CCR5 expressing CCR5NKRCEM cells due to a single nucleotide mismatch in target sequence, as shown in FIG. 17A. Similarly, huCCR5 shRNA reduced human CCR5, but not rhesus CCR5. Similar to the homologous human CCR5 shRNA, there was no apparent cytotoxicity (data not shown).

Example 11

Figure 17B:
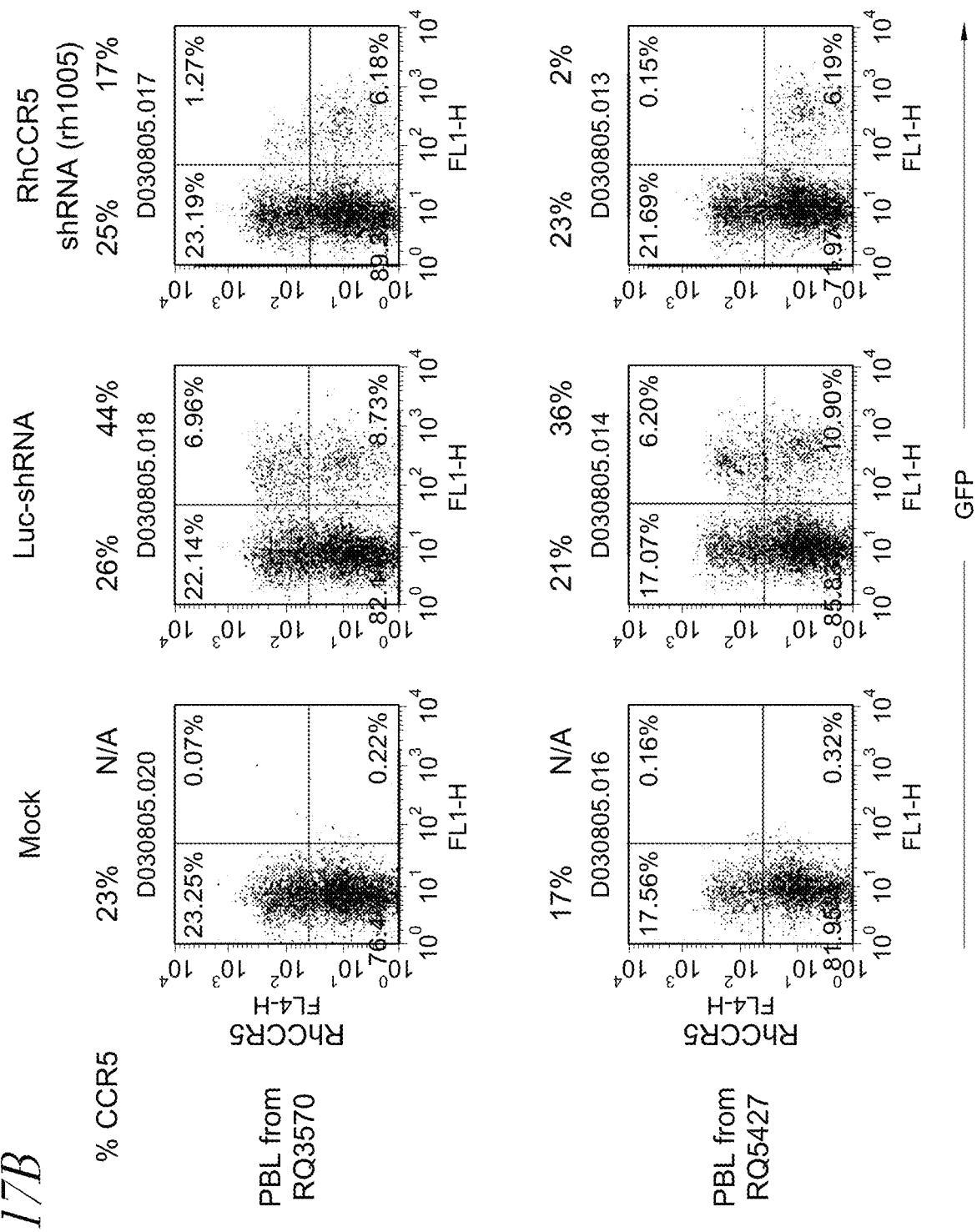
FIG. 17B shows the results of a study in which PHA/IL2 activated primary rhesus macaque lymphocytes were infected with a SIV vector expressing shRNA against rhesus CCR5 (rh1005)(SEQ ID NO: 20). CCR5 expression was analyzed by flow cytometry in GFP+ and GFP− cells. A vector expressing a shRNA against firefly luciferase was used as a control. The figure illustrates that CCR5 expression was inhibited by the RhCCR5 (rh1005) shRNA in primary rhesus PBMC.

The function and safety of the rhesus CCR5 shRNA (rh1005) (SEQ ID NO: 20) was tested by transducing peripheral blood mobilized rhesus CD34+ cells followed by autologous transplant into myeloablated animals. In this example, PHA/IL2 activated primary rhesus macaque lymphocytes were infected with a SIV vector expressing shRNA against rhesus CCR5 (rh1005) (SEQ ID NO: 20) and CCR5 expression was analyzed by flow cytometry in GFP+ and GFP− cells. A vector expressing a shRNA against firefly luciferase was used as a control. As shown in FIG. 17B, CCR5 expression was also inhibited by the RhCCR5 shRNA in primary rhesus PBMC.

Figure 18A:
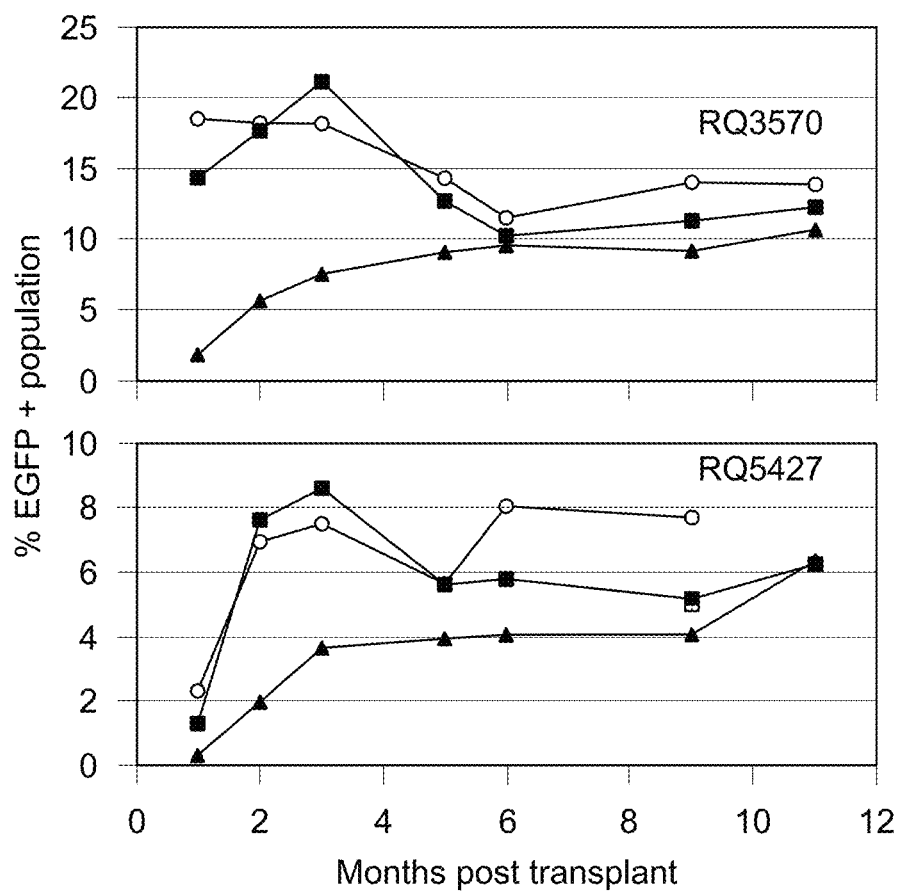
FIG. 18A illustrates stable EGFP marking in peripheral blood cells in transplanted rhesus macaques. Following stem cell transplant, EGFP expression was monitored in Granulocyte (open square), Monocyte (closed square), Lymphocyte (closed triangle) populations by flow cytometric analysis.

Two rhesus macaques (RQ3570 and RQ5427) were subsequently transplanted with CD34+ HSC cells transduced with this vector. Nonhuman primate mobilized and immunoselected PB CD34+ cells from the two animals were transduced ex vivo with the vector (SIV rhCCR5 shRNA RhMLV-E) at an moi of 2.4 once a day for 2 days in the presence of SCF (50 ng/ml) and IL6 (50 ng/ml) in serum free media ex vivo. Transduction efficiency was analyzed by quantitating EGFP expression by flow cytometry 64 hour post first transduction. 18 and 7.4% of the cells were EGFP positive for animals RQ3570 and RQ5427, respectively. The two animals received autologous transplants with $1.6 \times 10^8$ transduced PB CD34+ cells. All animals received 10 Gy of total body irradiation as a 5-Gy fractionated dose given on 2 consecutive days before transplantation (days −1 and 0, with day 0 being the date of reinfusion). Leukocyte counts recovered to 1,000 cells/µl between days 7 and 8, with platelet counts never falling below 50,000 µl). Normal kinetics and marking as monitored in flow cytometric analysis by the EGFP reporter in the vector was observed in granulocyte, monocyte and lymphocyte lineages (depicted as open square, closed square, and closed triangle populations, respectively) for a period of 11 months to date (FIG. 18A).

Figure 18B:
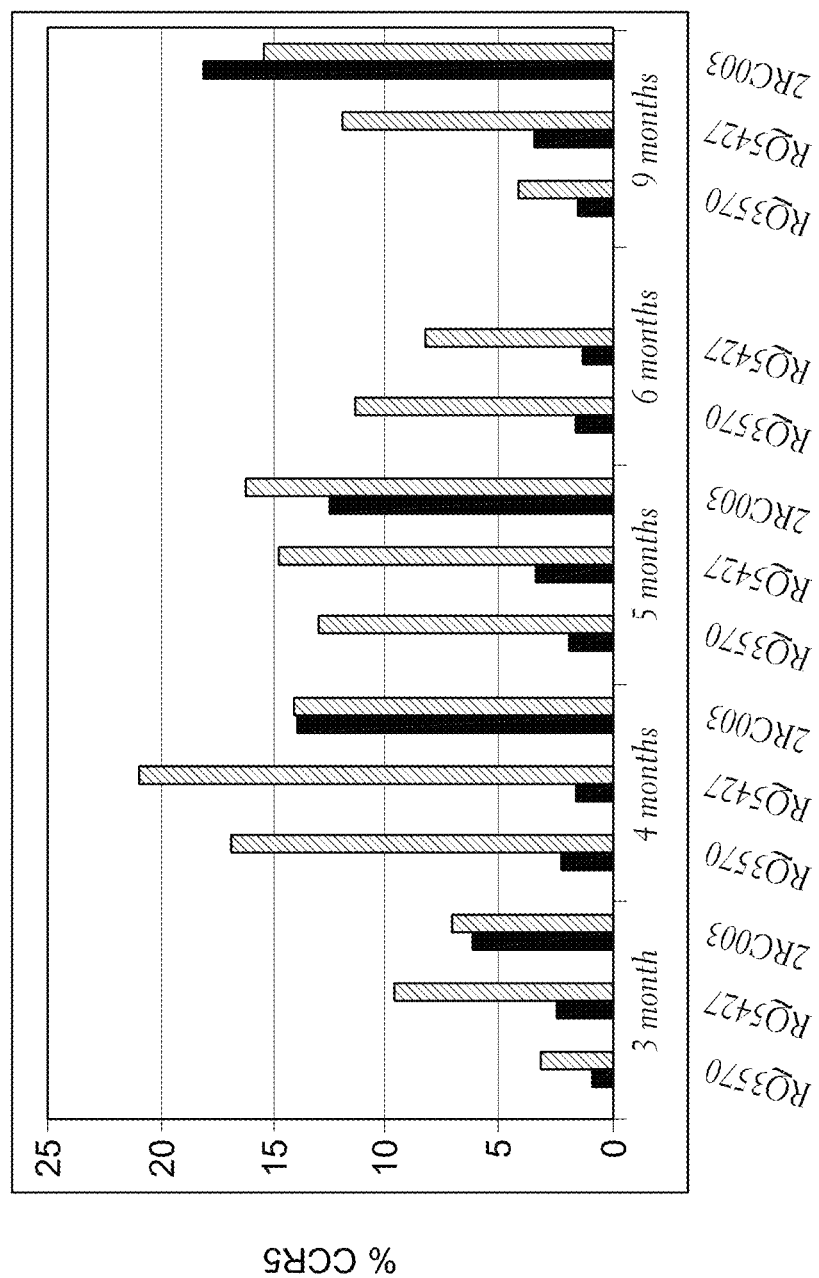
FIG. 18B shows stable CCR5 reduction in GFP+ lymphocytes. The percentage of CCR5 expression in GFP+ (black bar) and in GFP− (gray bar) cells was monitored by flow cytometry. Control animal 2RC003 was previously transplanted with a lentiviral vector bearing GFP, but no shRNA expression unit.

Cell surface expression of CCR5 was reduced in the EGFP+ population relative to the EGFP− population at all time points assayed (up to 9 months following transplant) as shown in FIG. 18B. The extent of CCR5 down-regulation ranged from 3-10 fold. In contrast, a control animal, 2RC003, that was transplanted with a lentiviral vector expressing EGFP but without shRNA, showed no evidence of CCR5 down-regulation at any time point. FIG. 18B indicates the percentage of CCR5 expression in GFP+(black bar) and in GFP− (gray bar) cells as monitored by flow cytometry.

Figure 18C:
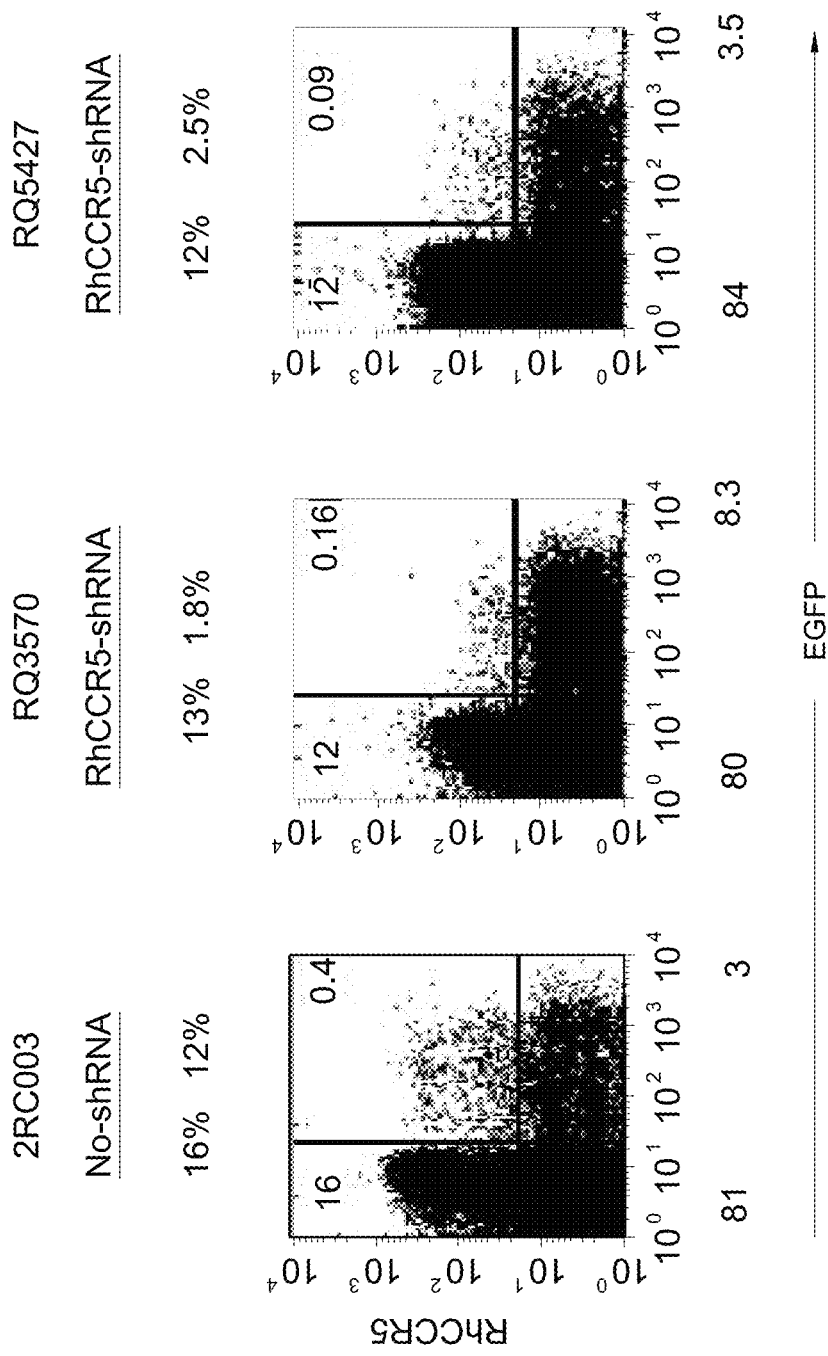
FIG. 18C is a representative CCR5/GFP plot at 5 months post transplant. Peripheral blood from transplanted macaques was stained for CCR5 and CCR5 and EGFP expression in the lymphocyte population and analyzed by flow cytometry. Based on the percentage of events in each quadrant (shown in each quadrant), percent CCR5 expression in GFP+ and GFP− lymphocyte populations were calculated and shown on the top of each panel.

Peripheral blood from transplanted macaques was stained for CCR5 and CCR5 and EGFP expression in the lymphocyte population was analyzed by flow cytometry. Based on the percentage of events in each quadrant (shown in each quadrant) of FIG. 18C, the percentage of CCR5 expression in GFP+ and GFP− lymphocyte populations was calculated and is shown on the top of each panel. 5-10 fold reduction of CCR5 mRNA levels was seen in EGFP+ cells, consistent with the flow cytometric analysis of CCR5 cell surface expression (data not shown).

Figure 18D:
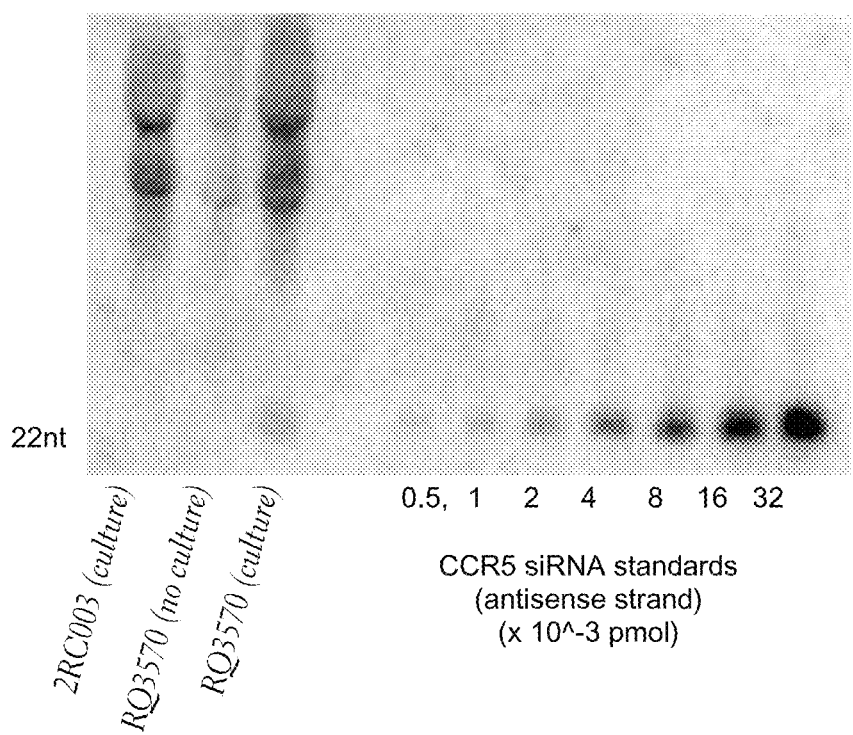
FIG. 18D shows detection of siRNA in rhesus macaque lymphocytes. 22 nt antisense strand siRNA was detected by Northern Blot analysis in the small RNA fraction of PHA/IL2 stimulated lymphocytes from shRNA transduced animal RQ3570 but not in cells from control animal 2RC003.

Micro-Northern blot analysis of lymphocytes from one transplanted rhesus demonstrated the presence of a 22-nucleotide band corresponding to the anti-sense strand of CCR5 siRNA (FIG. 18D) in the small RNA fraction of PHA/IL2 stimulated lymphocytes from shRNA transduced animal RQ3570, but not in cells from control animal 2RC003. Further quantitation of the levels of siRNA by RT-PCR indicated expression of approximately $3 \times 10^4$ siRNA molecules per EGFP+ cell, and was consistent in both animals. This number is also consistent with the level of siRNA expressed from rhesus PBL transduced in vitro (data not shown).

Figure 19A:
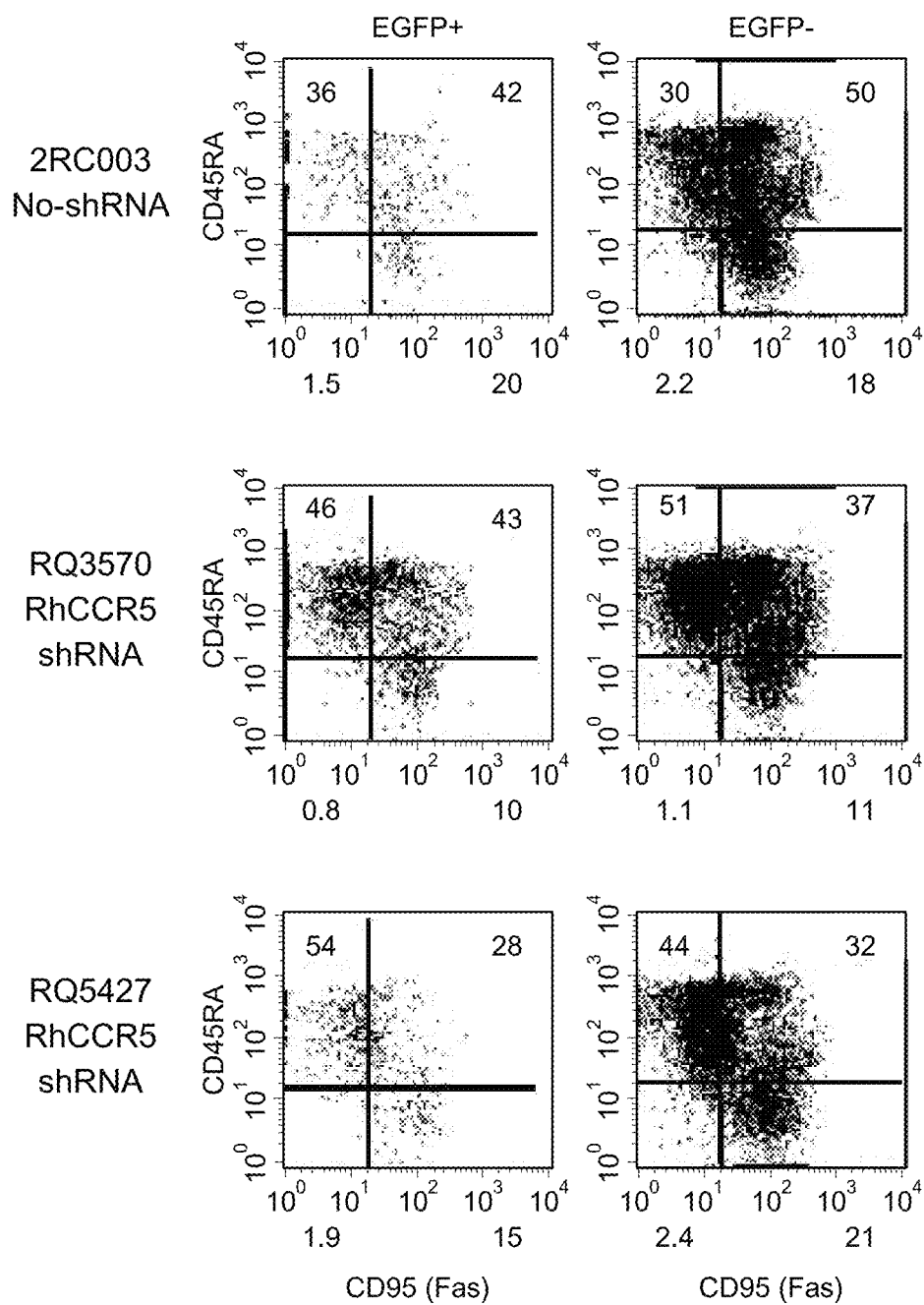
FIGS. 19A-C illustrate lymphocyte cell surface marker expression in EGFP+ or EGFP− lymphocyte population. As shown, peripheral blood from rhesus macaques 2RC003, RQ3570, and RQ5427 at 11 months post transplant was analyzed by flow cytometry for cell surface marker expression on EGFP+ or EGFP− gated lymphocyte populations.
Figure 19B:
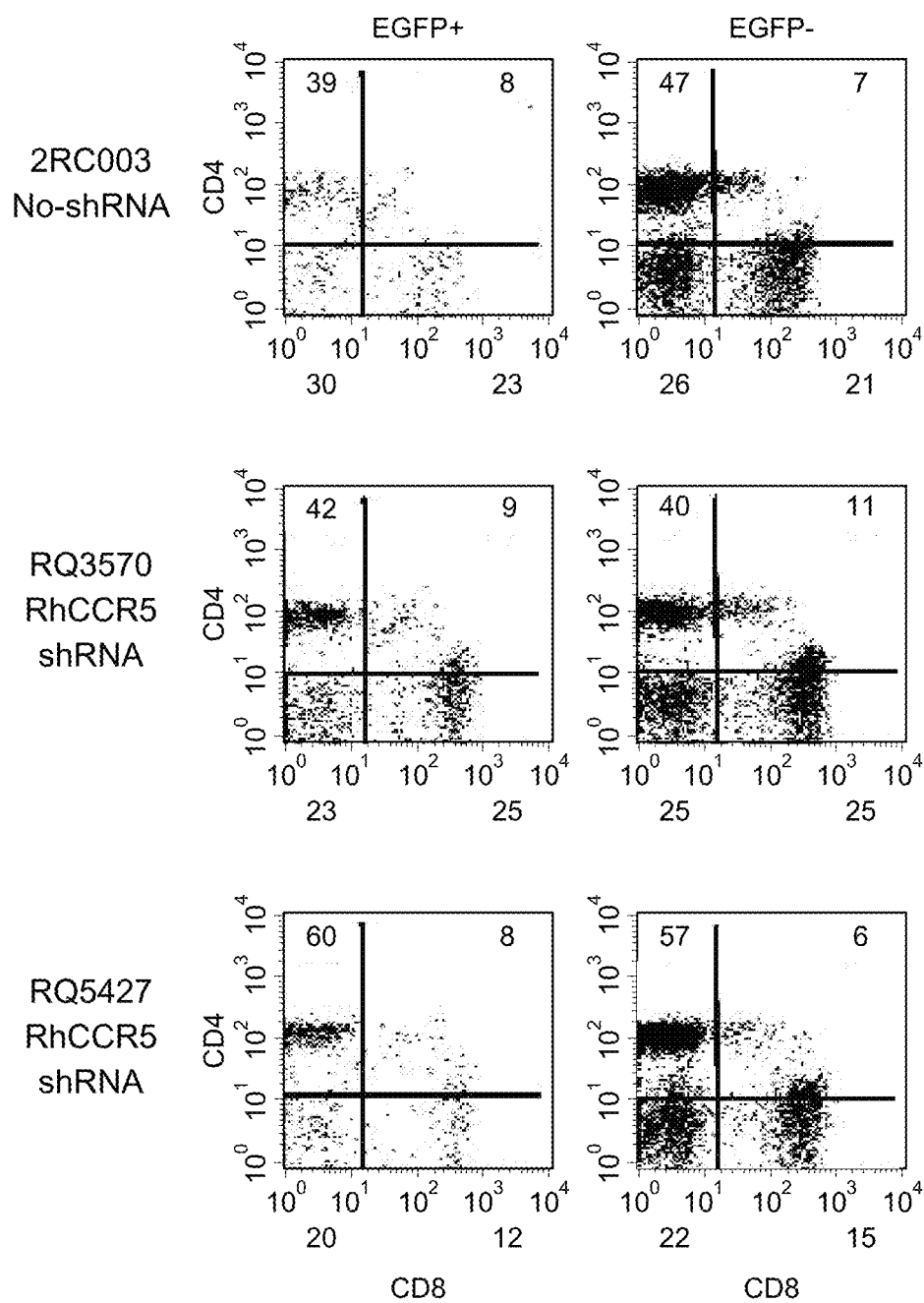
Figure 19C:
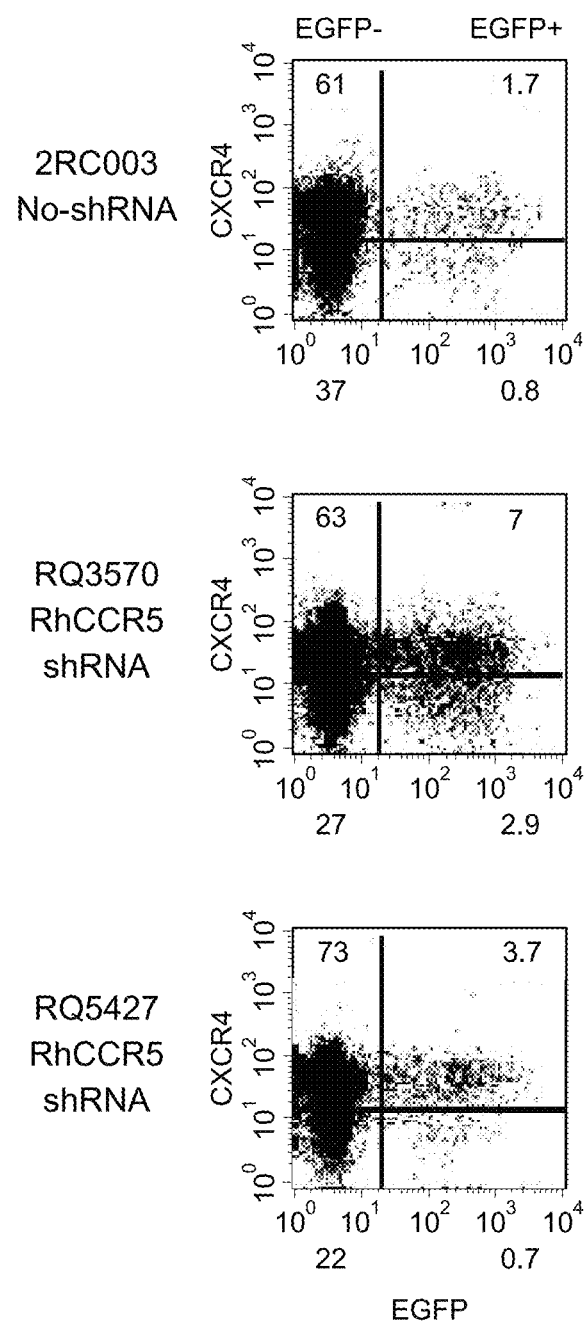
Figure 20:
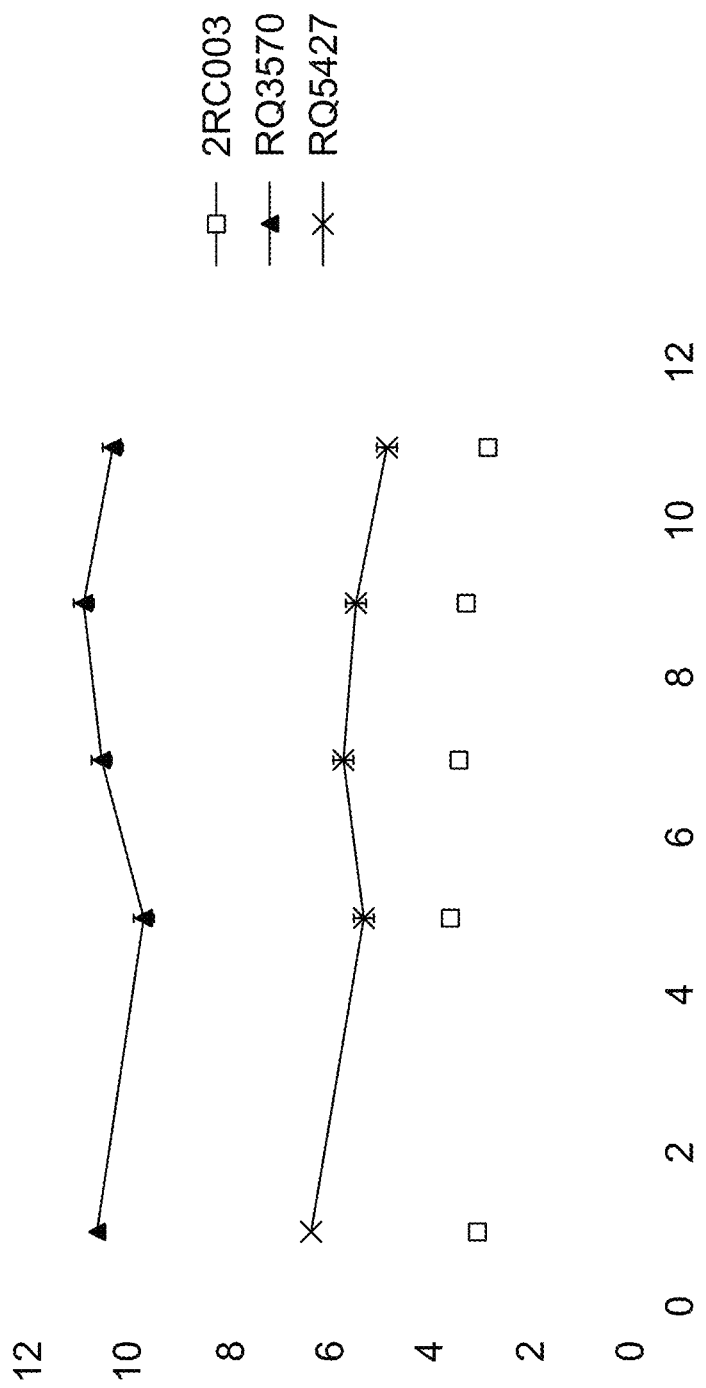
FIG. 20 shows kinetics of percent EGFP+ cells in PHA/IL2 stimulated lymphocytes during ex vivo culture. Peripheral blood lymphocytes were isolated from transplanted animals at 11 months post transplant, stimulated with PHA/IL2 for 2 days and cultured with IL2 for 9 days (total of 11 days). The percent EGFP expression was monitored in lymphocyte population by flow cytometry. The experiment was done in triplicate. Average percentages of EGFP expression in lymphocyte populations and error bars (standard deviation) are shown.
Figure 21:
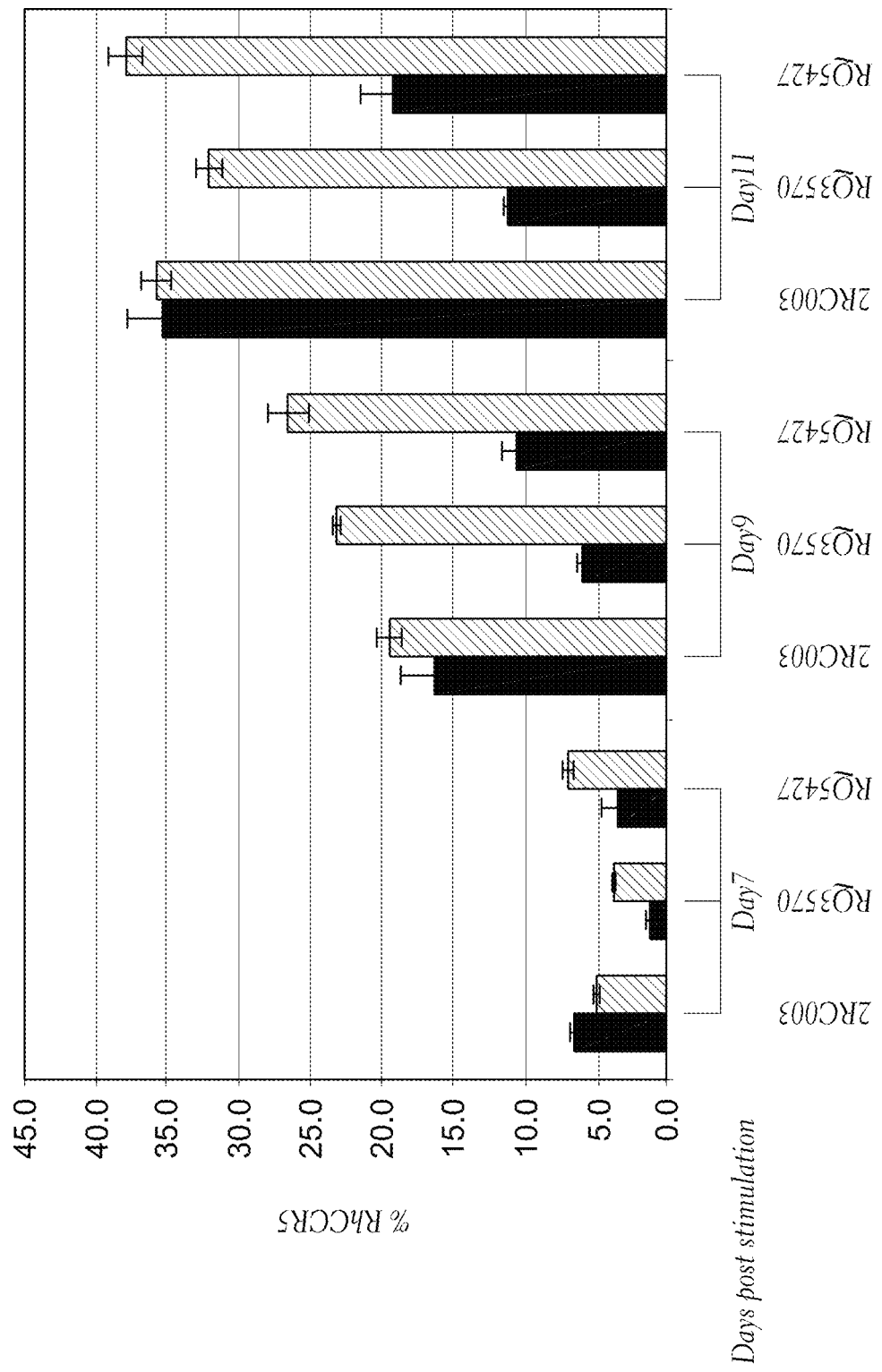
FIG. 21 illustrates stable CCR5 reduction in lymphocytes during ex vivo culture. Cells from the experiments shown in FIGS. 19-20 were analyzed for the percent CCR5 expression in EGFP+(black bar) and in EGFP− (gray bar) by flow cytometry at day 7, 9 and 11 during PHA/IL2 ex vivo culture. Average percentage of CCR5 expression and error bars (standard deviation) are shown. The experiment was done in triplicate.

Importantly, despite expression of CCR5 siRNA throughout hematopoietic cell differentiation and over the 11 month period of this study, no apparent toxicities were observed. The level of marked cells increased following transplant with normal kinetics and remained stable over the course of the study, 14 months. As shown in FIGS. 19A-C, the flow cytometric profiles of CD4, CD8, CXCR4 chemokine (c-x-c motif) receptor 4, CD45RA, and CD95 (fas) are nearly identical for EGFP+ and EGFP− subpopulations. CD45RA+/CD95-cells represent a naive T lymphocytes population whereas CD45RA−/CD95+ represent memory T lymphocytes populations (J. J. Mattapallil et al. 434, 1093-1097, Nature, (2005)). As shown in FIG. 20, the EGFP marked lymphocytes respond normally in culture to PHA and IL2 stimulation with the same kinetics as non-transduced cells and are maintained at the same frequency for up to 12 days. Over the same period of ex vivo culture the reduction of CCR5 surface expression in the EGFP+ population persists even though the overall expression of CCR5 in the EGFP− population increases from 5% to 35% of the cell population, as seen in FIG. 21.

Figure 22A:
FIG. 22A illustrates inhibition of SIV replication ex vivo. Peripheral blood lymphocytes from RQ3570 at 13 months post transplant were sorted for GFP+ and GFP− populations, stimulated with PHA/IL2 for 2 days and IL2 for 2 days. Following the stimulation, $1 \times 10^5$ GFP+ or GFP− cells were infected with 100 µl of SIVmac239 at moi of 0.04 (infectious unit of the virus stock was $4 \times 10^4$/ml by titrating on MAGI-CCR5 cells) for 1 hour, and monitored for p27 production for 11 days in culture. The infection experiment was done in triplicate. Average p27 production (ng/ml) in culture supernatant and error bars (standard deviation) are shown.

Next, the susceptibility of the rhesus PBL to simian immunodeficiency virus infection was tested. Peripheral blood lymphocytes from RQ3570 at 13 months post transplant were sorted for GFP+ and GFP− populations, stimulated with PHA/IL2 for 2 days and IL2 for 2 days. Sorting purity of GFP+ and GFP− was 93.4% and 99.9%, respectively. Following the stimulation, $1 \times 10^5$ GFP+ or GFP− cells were infected with 100 µl of SIVmac239 at moi of 0.04 (Infectious unit of the virus stock was $4 \times 10^4$/ml by titrating on MAGI-CCR5 cells) for 1 hour, and monitored for p27 production for 11 days in culture. The infection experiment was done in triplicate. Average p27 production (ng/ml) in culture supernatant and error bar (standard deviation) are shown in FIG. 22A. Both sub-populations were proliferated at comparable efficiencies based on cell counts.

Figure 22B:
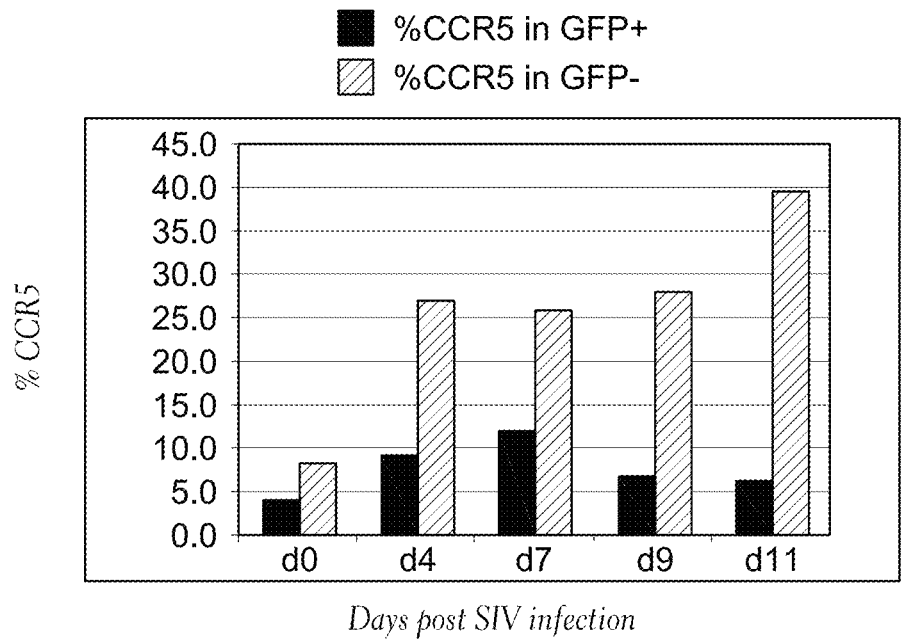
FIG. 22B shows the percentage of CCR5 expression in GFP+ and GFP-sorted lymphocytes. CCR5 expression was monitored during ex vivo culture by flow cytometric analysis and compared between GFP+(black bar) and GFP− sorted (gray bar) lymphocyte populations.
Figure 22C:
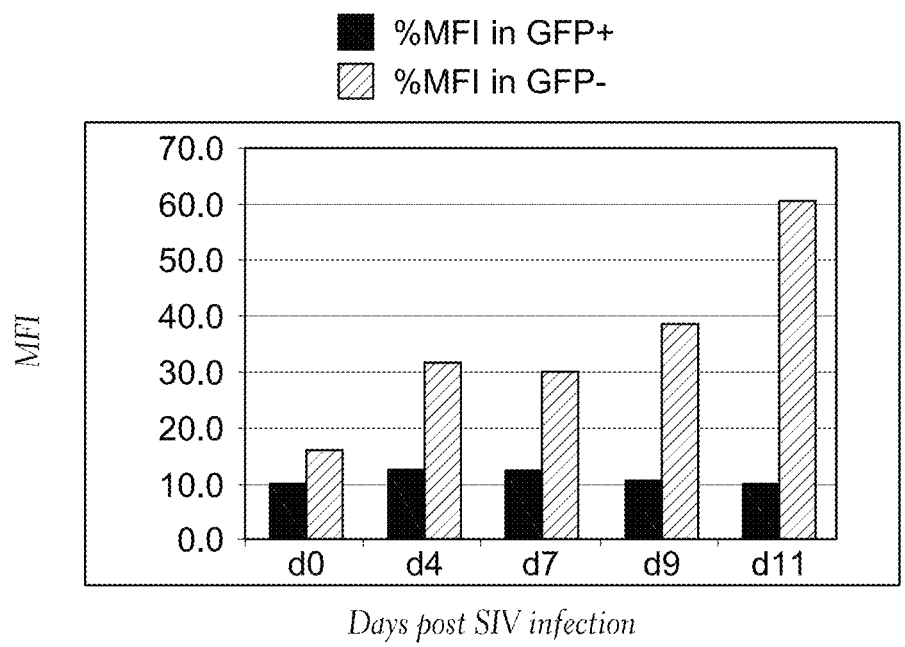
FIG. 22C illustrates the mean fluorescent intensity (MFI) of CCR5 expression in GFP+ sorted (black bar) and GFP− sorted (gray bar) PHA/IL2 activated lymphocytes.

FIG. 22B shows CCR5 expression monitored during ex vivo culture by flow cytometric analysis and compared between GFP+(black bar) and GFP− sorted (gray bar) lymphocyte populations. At the time of infection the percent and MFI of CCR5 expression was 4% and 9.9% in the GFP+ population and 8% and 16.2% in the GFP− population. As shown in FIG. 22C, over a nine day period of culture the GFP+ population of cells produced about 3 fold lower levels of SIVmac239 p27 antigen than did the GFP− population. Mean fluorescent intensity (MFI) of CCR5 expression is shown as a black bar in GFP+ sorted cells and a gray bar in GFP− sorted cells (PHA/IL2 activated lymphocytes). While the degree of resistance was relatively modest (3-fold over the course of the culture), it is important to note that the CCR5 levels significantly increased ex vivo due to lectin/IL-2 stimulation. In addition, although CCR5 has been reported as a primary and the most efficient co-receptor for SIV entry, SIV has been reported to utilize other co-receptors when CCR5 is not present (see, e.g., P. A. Marx and Z. Chen, Semin. Immunol. 10, 215-223 (1998)).

What is claimed is:

1. A retroviral construct for expressing an RNA within a cell, comprising:
   a nucleic acid having the R and U5 sequences from a 5' lentiviral long terminal repeat (LTR);
   a self-inactivating lentiviral 3' LTR; and
   a first promoter configured to be operably linked to a first RNA coding region encoding a first RNA,
   wherein the first promoter is located between the 5' LTR and the 3' LTR, and wherein the first RNA comprises a RNA duplex.

2. The retroviral construct of claim 1, wherein the first RNA comprises a sequence that is at least about 90% complementary to a target region of a pathogenic virus genome or genome transcript.

3. The retroviral construct of claim 2, wherein the pathogenic virus is human immunodeficiency virus (HIV), hepatitis A virus (HAV), hepatitis B virus (HBV), hepatitis C virus (HCV), cytomegalovirus (CMV), herpes simplex virus (HSV), influenza virus, adeno virus, human papillomavirus, Coxsackieviruses, Measles virus, or poliovirus.

4. The retroviral construct of claim 3, wherein the pathogenic virus is HIV-1 or HIV-2.

5. The retroviral construct of claim 2, wherein the target region of the pathogenic virus genome or genome transcript is a region in HIV vif gene, HIV nef gene, HIV rev gene, HIV gag gene, HIV pol gene, HIV LTRs, HIV trans-activation response (TAR) element, HIV Rev response element (RRE), or a transcript thereof.

6. The retroviral construct of claim 2, wherein the target region comprises a DNA cis-regulatory element, a RNA cis-regulatory element, or a combination thereof.

7. The retroviral construct of claim 1, wherein the first RNA comprises a sequence that is at least about 90% complementary to a cellular target sequence that encodes a protein involved in viral life cycle.

8. The retroviral construct of claim 7, wherein the protein involved in viral life cycle is selected from the group consisting of a cell surface receptors involved in viral entry, a transcription factor involved in the transcription of a viral genome, a protein involved in viral integration into a host chromosome, a protein involved in translation of viral gene expression, and a combination thereof.

9. The retroviral construct of claim 7, wherein the protein involved in viral life cycle is a protein selected from the group consisting of CAR, an Integrins, MHC I, Heparan sulfate glycoaminoglycan, Siliac Acid, Heparan sulfate glycosaminoglycan, ICAM-1, murine-like class I integral membrane glycoprotein, CD81, Low density lipoprotein receptor, CD4, PVR, HveB, HveC, CD46, and CD55.

10. The retroviral construct of claim 7, wherein the protein involved in viral life cycle is a protein selected from the group consisting of CC chemokine receptor 5 (CCR5), CXC chemokine receptor 4 (CXCR4), cyclophilin, CRM-1, importin-β, and HP68.

11. The retroviral construct of claim 7, wherein the protein involved in viral life cycle is a cellular receptor involved in recognition by a virus selected from the group consisting of adenoviruses, cytomegalovirus, coxsackieviruses, hepatitis A virus, hepatitis C virus, HIV, HSV, influenza virus, measles virus, poliovirus, and human papillomavirus.

12. The retroviral construct of claim 7, wherein the protein involved in viral life cycle is a co-receptor necessary for viral replication.

13. The retroviral construct of claim 1, wherein the RNA duplex is at least about 15 nucleotides in length.

14. The retroviral construct of claim 1, wherein the first RNA is a single stranded RNA comprising a stem-loop.

15. The retroviral construct of claim 1, wherein the RNA duplex is flanked by a single stranded region on one side or both sides.

16. The retroviral construct of claim 1, wherein the first promoter is a RNA polymerase III promoter.

17. The retroviral construct of claim 1, wherein the first RNA coding region is followed by at least one termination sequence.

18. The retroviral construct of claim 1, wherein the first RNA coding region encodes a self-complementary RNA molecule having a sense region, an antisense region and a loop region.

19. The retroviral construct of claim 18, wherein the sense region and the antisense region are about 15 and about 30 nucleotides in length.

20. The retroviral construct of claim 1, wherein the target region is about 15 to about 30 nucleotides in length.

* * * * *

SEQUENCE LISTING

<160> NUMBER OF SEQ ID NOS: 39

<210> SEQ ID NO 1
<211> LENGTH: 56
<212> TYPE: DNA
<213> ORGANISM: Artificial Sequence
<220> FEATURE:
<223> OTHER INFORMATION: This represents an anti-human specific siRNA
      cassette comprising human sequence and synthetic
      linker, loop and terminator sequences.

<400> SEQUENCE: 1
accgagcatg actgacatct acttcaagag agtagatgtc agtcatgctc tttttc        56

<210> SEQ ID NO 2
<211> LENGTH: 50
<212> TYPE: DNA
<213> ORGANISM: Artificial Sequence
<220> FEATURE:
<223> OTHER INFORMATION: This represents an anti-human immune deficiency
      virus specific siRNA cassette comprising human
      immune deficiency virus sequence and synthetic
      linker, loop and terminator sequences.

<400> SEQUENCE: 2
ggtggagaga gagacattca agagatgtct ctctctccac cttcttttc                50

<210> SEQ ID NO 3
<211> LENGTH: 9941
<212> TYPE: DNA
<213> ORGANISM: Artificial Sequence
<220> FEATURE:
<223> OTHER INFORMATION: This sequence represents a lentiviral vector
      comprising a human immunodeficiency virus flap sequence, a green
      fluorescent protein variant sequence, a human ubiquitin promoter
      sequence and a woodchuck hepatitis regulator element sequence.

<400> SEQUENCE: 3
gtcgacggat cgggagatct cccgatcccc tatggtgcac tctcagtaca atctgctctg      60
atgccgcata gttaagccag tatctgctcc ctgcttgtgt gttggaggtc gctgagtagt     120
gcgcgagcaa aatttaagct acaacaaggc aaggcttgac cgacaattgc atgaagaatc     180
tgcttagggt taggcgtttt cgctgcttc gcgatgtacg ggccagatat acgcgttgac      240
attgattatt gactagttat taatagtaat caattacggg gtcattagtt catagcccat     300
atatggagtt ccgcgttaca taacttacgg taaatggccc gcctggctga ccgcccaacg     360
acccccgccc attgacgtca ataatgacgt atgttcccat agtaacgcca atagggactt     420
tccattgacg tcaatgggtg gagtatttac ggtaaactgc ccacttggca gtacatcaag     480
tgtatcatat gccaagtacg ccccctattg acgtcaatga cggtaaatgg cccgcctggc     540
attatgccca gtacatgacc ttatgggact ttcctacttg gcagtacatc tacgtattag     600
tcatcgctat taccatggtg atgcggtttt ggcagtacat caatgggcgt ggatagcggt     660
ttgactcacg gggatttcca agtctccacc ccattgacgt caatgggagt ttgttttggc     720
accaaaatca acgggacttt ccaaaatgtc gtaacaactc cgccccattg acgcaaatgg     780
gcggtaggcg tgtacggtgg gaggtctata taagcagcgc gttttgcctg tactgggtct     840
ctctggttag accagatctg agcctgggag ctctctggct aactagggaa cccactgctt     900
aagcctcaat aaagcttgcc ttgagtgctt caagtagtgt gtgcccgtct gttgtgtgac     960
tctggtaact agagatccct cagacccttt tagtcagtgt ggaaaatctc tagcagtggc    1020
gcccgaacag ggacttgaaa gcgaaaggga accagagga gctctctcga cgcaggactc    1080

```
ggcttgctga agcgcgcacg gcaagaggcg aggggcggcg actggtgagt acgccaaaaa    1140
ttttgactag cggaggctag aaggagagag atgggtgcga gagcgtcagt attaagcggg    1200
ggagaattag atcgcgatgg gaaaaaattc ggttaaggcc aggggggaaag aaaaaatata   1260 aattaaaaca tatagtatgg gcaagcaggg agctagaacg attcgcagtt aatcctggcc    1320
tgttagaaac atcagaaggc tgtagacaaa tactgggaca gctacaacca tcccttcaga    1380
caggatcaga agaacttaga tcattatata atacagtagc aaccctctat tgtgtgcatc    1440
aaaggataga gataaaagac accaaggaag ctttagacaa gatagaggaa gagcaaaaca    1500
aaagtaagac caccgcacag caagcggccg ctgatcttca gacctggagg aggagatatg    1560
agggacaatt ggagaagtga attatataaa tataaagtag taaaaattga accattagga    1620
gtagcaccca ccaaggcaaa gagaagagtg gtgcagagag aaaaaagagc agtgggaata    1680
ggagctttgt tccttgggtt cttgggagca gcaggaagca ctatgggcgc agcgtcaatg    1740
acgctgacgg tacaggccag acaattattg tctggtatag tgcagcagca gaacaatttg    1800
ctgagggcta ttgaggcgca acagcatctg ttgcaactca cagtctgggg catcaagcag    1860
ctccaggcaa gaatcctggc tgtggaaaga tacctaaagg atcaacagct cctggggatt    1920
tggggttgct ctggaaaact catttgcacc actgctgtgc cttggaatgc tagttggagt    1980
aataaatctc tggaacagat ttggaatcac acgacctgga tggagtggga cagagaaatt    2040
aacaattaca caagcttaat acactcctta attgaagaat cgcaaaacca gcaagaaaag    2100
aatgaacaag aattattgga attagataaa tgggcaagtt tgtggaattg gtttaacata    2160
acaaattggc tgtggtatat aaaattattc ataatgatag taggaggctt ggtaggttta    2220
agaatagttt ttgctgtact ttctatagtg aatagagtta ggcagggata ttcaccatta    2280
tcgtttcaga cccacctccc aaccccgagg ggacccgaca ggcccgaagg aatagaagaa    2340
gaaggtggag agagagacag agacagatcc attcgattag tgaacggatc ggcactgcgt    2400
gcgccaattc tgcagacaaa tggcagtatt catccacaat tttaaaagaa aagggggggat   2460 tggggggtac agtgcagggg aaagaatagt agacataata gcaacagaca tacaaactaa    2520
agaattacaa aaacaaatta caaaaattca aaattttcgg gtttattaca gggacagcag    2580
agatccagtt tggttaatta agggtgcagc ggcctccgcg ccgggttttg gcgcctcccg    2640
cgggcgcccc cctcctcacg gcgagcgctg ccacgtcaga cgaagggcgc aggagcgttc    2700
ctgatccttc cgcccggacg ctcaggacag cggcccgctg ctcataagac tcggccttag    2760
aaccccagta tcagcagaag gacattttag gacgggactt gggtgactct agggcactgg    2820
ttttctttcc agagagcgga acaggcgagg aaaagtagtc ccttctcggc gattctgcgg    2880
agggatctcc gtgggcggt gaacgccgat gattatataa ggacgcgccg ggtgtggcac     2940
agctagttcc gtcgcagccg ggatttgggt cgcggttctt gtttgtggat cgctgtgatc    3000
gtcacttggt gagttgcggg ctgctgggct ggccggggct ttcgtggccg ccgggccgct    3060
cggtgggacg gaagcgtgtg gagagaccgc caagggctgt agtctgggtc cgcgagcaag    3120
gttgccctga actgggggtt ggggggagcg cacaaaatgg cggctgttcc cgagtcttga    3180
atggaagacg cttgtaaggc gggctgtgag gtcgttgaaa caaggtgggg gcatggtgg     3240 gcggcaagaa cccaaggtct tgaggccttc gctaatgcgg gaaagctctt attcgggtga    3300
gatgggctgg ggcaccatct ggggaccctg acgtgaagtt tgtcactgac tggagaactc    3360
gggtttgtcg tctggttgcg ggggcggcag ttatgcggtg ccgttgggca gtgcacccgt    3420
```

```
accctttggga gcgcgcgcct cgtcgtgtcg tgacgtcacc cgttctgttg gcttataatg    3480
cagggtgggg ccacctgccg gtaggtgtgc ggtaggcttt tctccgtcgc aggacgcagg    3540
gttcgggcct agggtaggct ctcctgaatc gacaggcgcc ggacctctgg tgagggagg     3600 gataagtgag gcgtcagttt cttttggtcgg ttttatgtac ctatcttctt aagtagctga   3660
agctccggtt ttgaactatg cgctcggggt tggcgagtgt gttttgtgaa gttttttagg    3720
caccttttga aatgtaatca tttgggtcaa tatgtaattt tcagtgttag actagtaaag    3780
cttctgcagg tcgactctag aaaattgtcc gctaaattct ggccgttttt ggcttttttg    3840
ttagacagga tccccgggta ccggtcgcca ccatggtgag caagggcgag gagctgttca    3900
ccggggtggt gcccatcctg gtcgagctgg acggcgacgt aaacggccac aagttcagcg    3960
tgtccggcga gggcgagggc gatgccacct acggcaagct gaccctgaag ttcatctgca    4020
ccaccggcaa gctgcccgtg ccctggccca cccctcgtgac caccctgacc tacggcgtgc  4080
agtgcttcag ccgctacccc gaccacatga agcagcacga cttcttcaag tccgccatgc    4140
ccgaaggcta cgtccaggag cgcaccatct tcttcaagga cgacggcaac tacaagaccc    4200
gcgccgaggt gaagttcgag ggcgacaccc tggtgaaccg catcgagctg aagggcatcg    4260
acttcaagga ggacggcaac atcctggggc acaagctgga gtacaactac aacagccaca    4320
acgtctatat catggccgac aagcagaaga cggcatcaa ggtgaacttc aagatccgcc     4380
acaacatcga ggacggcagc gtgcagctcg ccgaccacta ccagcagaac ccccatcg      4440 gcgacggccc cgtgctgctg cccgacaacc actacctgag cacccagtcc gccctgagca    4500
aagaccccaa cgagaagcgc gatcacatgg tcctgctgga gttcgtgacc gccgccggga    4560
tcactctcgg catggacgag ctgtacaagt aaagcggccg cgactctaga attcgatatc    4620
aagcttatcg ataatcaacc tctggattac aaaatttgtg aaagattgac tggtattctt    4680
aactatgttg ctccttttac gctatgtgga tacgctgctt taatgccttt gtatcatgct    4740
attgcttccc gtatggcttt cattttctcc tccttgtata aatcctggtt gctgtctctt    4800
tatgaggagt tgtggcccgt tgtcaggcaa cgtggcgtgg tgtgcactgt gtttgctgac    4860
gcaaccccca ctggttgggg cattgccacc acctgtcagc tcctttccgg gactttcgct    4920
ttccccctcc ctattgccac ggcggaactc atcgccgcct gccttgcccg ctgctggaca    4980
ggggctcggc tgttgggcac tgacaattcc gtggtgttgt cggggaaatc atcgtccttt    5040
ccttggctgc tcgcctgtgt tgccacctgg attctgcgcg gacgtccttc tgctacgtc    5100 ccttcggccc tcaatccagc ggaccttcct tcccgcggcc tgctgccggc tctgcggcct    5160
cttccgcgtc ttcgccttcg ccctcagacg agtcggatct ccctttgggc cgcctccccg    5220
catcgatacc gtcgacctcg agacctagaa aaacatggag caatcacaag tagcaataca    5280
gcagctacca atgctgattg tgcctggcta aagcacaag aggaggagga ggtgggtttt    5340
ccagtcacac ctcaggtacc tttaagacca atgacttaca aggcagctgt agatcttagc    5400
cactttttaa aagaaaaggg gggactggaa gggctaattc actcccaacg aagacaagat    5460
atccttgatc tgtggatcta ccacacacaa ggctacttcc ctgattggca gaactacaca    5520
ccagggccag ggatcagata tccactgacc tttggatggt gctacaagct agtaccagtt    5580
gagcaagaga aggtagaaga agccaatgaa ggagagaaca cccgcttgtt acaccctgtg    5640
agcctgcatg ggatggatga cccggagaga gaagtattag agtggaggtt tgacagccgc    5700
ctagcatttc atcacatggc ccgagagctg catccggact gtactgggtc tctctggtta    5760
gaccagatct gagcctggga gctctctggc taactaggga acccactgct taagcctcaa    5820
```

```
taaagcttgc cttgagtgct tcaagtagtg tgtgcccgtc tgttgtgtga ctctggtaac    5880
tagagatccc tcagaccctt ttagtcagtg tggaaaatct ctagcagggc ccgtttaaac    5940
ccgctgatca gcctcgactg tgccttctag ttgccagcca tctgttgttt gcccctcccc    6000
cgtgccttcc ttgaccctgg aaggtgccac tcccactgtc ctttcctaat aaaatgagga    6060
aattgcatcg cattgtctga gtaggtgtca ttctattctg ggggtgggg tggggcagga     6120 cagcaagggg gaggattggg aagacaatag caggcatgct ggggatgcgg tgggctctat    6180
ggcttctgag gcggaaagaa ccagctgggg ctctaggggg tatccccacg cgccctgtag    6240
cggcgcatta agcgcggcgg gtgtggtggt tacgcgcagc gtgaccgcta cacttgccag    6300
cgccctagcg cccgctcctt tcgctttctt cccttccttt ctcgccacgt tcgccggctt    6360
tccccgtcaa gctctaaatc gggggctccc tttagggttc cgatttagtg ctttacggca    6420
cctcgacccc aaaaaacttg attagggtga tggttcacgt agtgggccat cgccctgata    6480
gacggttttt cgccctttga cgttggagtc acgttctttt aatagtggac tcttgttcca    6540
aactggaaca acactcaacc ctatctcggt ctattctttt gatttataag ggattttgcc    6600
gatttcggcc tattggttaa aaaatgagct gatttaacaa aaatttaacg cgaattaatt    6660
ctgtggaatg tgtgtcagtt agggtgtgga aagtccccag gctccccagc aggcagaagt    6720
atgcaaagca tgcatctcaa ttagtcagca accaggtgtg gaaagtcccc aggctcccca    6780
gcaggcagaa gtatgcaaag catgcatctc aattagtcag caaccatagt cccgccccta    6840
actccgccca tcccgcccct aactccgccc agttccgccc attctccgcc ccatggctga    6900
ctaatttttt ttatttatgc agaggccgag gccgcctctg cctctgagct attccagaag    6960
tagtgaggag gcttttttgg aggcctaggc ttttgcaaaa agctcccggg agcttgtata    7020
tccattttcg gatctgatca gcacgtgttg acaattaatc atcggcatag tatatcggca    7080
tagtataata cgacaaggtg aggaactaaa ccatggccaa gttgaccagt gccgttccgg    7140
tgctcaccgc gcgcgacgtc gccggagcgg tcgagttctg gaccgaccgg ctcgggttct    7200
cccgggactt cgtggaggac gacttcgccg gtgtggtccg ggacgacgtg accctgttca    7260
tcagcgcggt ccaggaccag gtggtgccgg acaacaccct ggcctgggtg tgggtgcgcg    7320
gcctggacga gctgtacgcc gagtggtcgg aggtcgtgtc cacgaacttc cgggacgcct    7380
ccgggccggc catgaccgag atcggcgagc agccgtgggg cgggagttc gccctgcgcg     7440 acccggccgg caactgcgtg cacttcgtgg ccgaggagca ggactgacac gtgctacgag    7500
atttcgattc caccgccgcc ttctatgaaa ggttgggctt cggaatcgtt ttccgggacg    7560
ccggctggat gatcctccag cgcggggatc tcatgctgga gttcttcgcc cacccaact      7620 tgtttattgc agcttataat ggttacaaat aaagcaatag catcacaaat ttcacaaata    7680
aagcattttt ttcactgcat tctagttgtg gtttgtccaa actcatcaat gtatcttatc    7740
atgtctgtat accgtcgacc tctagctaga gcttggcgta atcatggtca tagctgtttc    7800
ctgtgtgaaa ttgttatccg ctcacaattc cacacaacat acgagccgga agcataaagt    7860
gtaaagcctg gggtgcctaa tgagtgagct aactcacatt aattgcgttg cgctcactgc    7920
ccgctttcca gtcgggaaac ctgtcgtgcc agctgcatta atgaatcggc caacgcgcgg    7980
ggagaggcgg tttgcgtatt gggcgctctt ccgcttcctc gctcactgac tcgctgcgct    8040
cggtcgttcg gctgcggcga gcggtatcag ctcactcaaa ggcggtaata cggttatcca    8100
cagaatcagg ggataacgca ggaaagaaca tgtgagcaaa aggccagcaa aaggccagga    8160
```

-continued

```
accgtaaaaa ggccgcgttg ctggcgtttt tccataggct ccgccccct gacgagcatc      8220
acaaaaatcg acgctcaagt cagaggtggc gaaacccgac aggactataa agataccagg      8280
cgtttccccc tggaagctcc ctcgtgcgct ctcctgttcc gaccctgccg cttaccggat      8340
acctgtccgc ctttctccct cgggaagcg tggcgctttc tcatagctca cgctgtaggt       8400
atctcagttc ggtgtaggtc gttcgctcca agctgggctg tgtgcacgaa ccccccgttc      8460
agcccgaccg ctgcgcctta ccggtaact atcgtcttga gtccaacccg gtaagacacg       8520
acttatcgcc actggcagca gccactggta acaggattag cagagcgagg tatgtaggcg      8580
gtgctacaga gttcttgaag tggtggccta actacggcta cactagaaga acagtatttg      8640
gtatctgcgc tctgctgaag ccagttacct tcggaaaaag agttggtagc tcttgatccg      8700
gcaaacaaac caccgctggt agcggtggtt ttttgtttg caagcagcag attacgcgca       8760
gaaaaaaagg atctcaagaa gatcctttga tcttttctac ggggtctgac gctcagtgga      8820
acgaaaactc acgttaaggg attttggtca tgagattatc aaaaaggatc ttcacctaga      8880
tccttttaaa ttaaaaatga agttttaaat caatctaaag tatatatgag taaacttggt      8940
ctgacagtta ccaatgctta atcagtgagg cacctatctc agcgatctgt ctatttcgtt      9000
catccatagt tgcctgactc cccgtcgtgt agataactac gatacgggag gcttaccat       9060
ctggccccag tgctgcaatg ataccgcgag acccacgctc accggctcca gatttatcag      9120
caataaacca gccagccgga agggccgagc gcagaagtgg tcctgcaact ttatccgcct      9180
ccatccagtc tattaattgt tgccgggaag ctagagtaag tagttcgcca gttaatagtt      9240
tgcgcaacgt tgttgccatt gctacaggca tcgtggtgtc acgctcgtcg tttggtatgg      9300
cttcattcag ctccggttcc caacgatcaa ggcgagttac atgatccccc atgttgtgca      9360
aaaaagcggt tagctccttc ggtcctccga tcgttgtcag aagtaagttg gccgcagtgt      9420
tatcactcat ggttatggca gcactgcata attctcttac tgtcatgcca tccgtaagat      9480
gcttttctgt gactggtgag tactcaacca agtcattctg agaatagtgt atgcggcgac      9540
cgagttgctc ttgcccggcg tcaatacggg ataataccgc gccacatagc agaactttaa      9600
aagtgctcat cattggaaaa cgttcttcgg ggcgaaaact ctcaaggatc ttaccgctgt      9660
tgagatccag ttcgatgtaa cccactcgtg cacccaactg atcttcagca tcttttactt      9720
tcaccagcgt ttctgggtga gcaaaaacag gaaggcaaaa tgccgcaaaa aagggaataa      9780
gggcgacacg gaaatgttga atactcatac tcttcctttt tcaatattat tgaagcattt      9840
atcagggtta ttgtctcatg agcggataca tatttgaatg tatttagaaa aataaacaaa      9900
tagggggttcc gcgcacattt ccccgaaaag tgccacctga c                         9941
```

<210> SEQ ID NO 4
<211> LENGTH: 334
<212> TYPE: DNA
<213> ORGANISM: Homo sapiens

<400> SEQUENCE: 4

```
ccccagtgga agacgcgca ggcaaaacgc accacgtgac ggagcgtgac cgcgcgccga        60
gcgcgcgcca aggtcgggca ggaagagggc ctatttccca tgattccttc atatttgcat      120
atacgataca aggctgttag agagataatt agaattaatt tgactgtaaa cacaaagata      180
ttagtacaaa atacgtgacg tagaaagtaa taatttcttg ggtagtttgc agttttaaaa      240
ttatgttttta aaatggacta tcatatgctt accgtaactt gaaagtattt cgatttcttg      300
gctttatata tcttgtggaa aggacgaaac accg                                  334
```

<210> SEQ ID NO 5
<211> LENGTH: 246
<212> TYPE: DNA
<213> ORGANISM: Homo sapiens

<400> SEQUENCE: 5

```
tctagaccat ggaattcgaa cgctgacgtc atcaacccgc tccaaggaat cgcgggccca      60
gtgtcactag gcgggaacac ccagcgcgcg tgcgccctgg caggaagatg gctgtgaggg     120
acaggggagt ggcgccctgc aatatttgca tgtcgctatg tgttctggga aatcaccata     180
aacgtgaaat gtctttggat ttgggaatct tataagttct gtatgagacc acggatccaa     240
aagctt                                                               246
```

<210> SEQ ID NO 6
<211> LENGTH: 355
<212> TYPE: DNA
<213> ORGANISM: Artificial Sequence
<220> FEATURE:
<223> OTHER INFORMATION: This represents a mutant human sequence having an introduced bacterial tet01 binding site.

<400> SEQUENCE: 6

```
gggaattccc ccagtggaaa gacgcgcagg caaaacgcac cacgtgacgg agcgtgaccg      60
cgcgccgagc ccaaggtcgg gcaggaagag ggcctatttc ccatgattcc ttcatatttg     120
catatacgat acaaggctgt tagagagata attagaatta atttgactgt aaacacaaag     180
atattagtac aaaatacgtg acgtagaaag taataatttc ttgggtagtt tgcagtttta     240
aaattatgtt ttaaaatgga ctatcatatg cttaccgtaa cttgaaagta ctctatcatt     300
gatagagtta tatatcttgt ggaaaggacg aaacaccgtg gtcttcaagc ttccg          355
```

<210> SEQ ID NO 7
<211> LENGTH: 634
<212> TYPE: DNA
<213> ORGANISM: E. coli

<400> SEQUENCE: 7

```
gctagccacc atgtccagat tagataaaag taaagtgatt aacagcgcat tagagctgct      60
taatgaggtc ggaatcgaag gtttaacaac ccgtaaactc gcccagaagc taggtgtaga     120
gcagcctaca ttgtattggc atgtaaaaaa taagcgggct ttgctcgacg ccttagccat     180
tgagatgtta gataggcacc atactcactt ttgcccttta gaaggggaaa gctggcaaga     240
ttttttacgt aataacgcta aagttttag atgtgcttta ctaagtcatc gcgatggagc     300
aaaagtacat ttaggtacac ggcctacaga aaaacagtat gaaactctcg aaaatcaatt     360
agccttttta tgccaacaag ttttttcact agagaatgca ttatatgcac tcagcgctgt     420
ggggcatttt actttaggtt gcgtattgga agatcaagag catcaagtcg ctaaagaaga     480
aagggaaaca cctactactg atagtatgcc gccattatta cgacaagcta tcgaattatt     540
tgatcaccaa ggtgcagagc cagccttctt attcggcctt gaattgatca tatgcggatt     600
agaaaaacaa cttaaatgtg aaagtgggtc ttaa                                 634
```

<210> SEQ ID NO 8
<211> LENGTH: 60
<212> TYPE: DNA
<213> ORGANISM: Artificial Sequence
<220> FEATURE:
<223> OTHER INFORMATION: This represents an anti-human specific siRNA cassette comprising human sequence and synthetic
linker, loop and terminator sequences.

<400> SEQUENCE: 8
gatccccgaa gatacacagc agttgtttca agagaacaac tgctgtgtat cttctttttc    60

<210> SEQ ID NO 9
<211> LENGTH: 60
<212> TYPE: DNA
<213> ORGANISM: Artificial Sequence
<220> FEATURE:
<223> OTHER INFORMATION: This represents an anti-human specific siRNA
      cassette comprising human sequence and synthetic
      linker, loop and terminator sequences.

<400> SEQUENCE: 9
gatccccgta ccgtgtctgc aatgtgttca agagacacat gcagacacg gtactttttc    60

<210> SEQ ID NO 10
<211> LENGTH: 246
<212> TYPE: DNA
<213> ORGANISM: Homo sapiens

<400> SEQUENCE: 10
tctagaccat ggaattcgaa cgctgacgtc atcaacccgc tccaaggaat cgcgggccca    60
gtgtcactag gcgggaacac ccagcgcgcg tgcgccctgg caggaagatg gctgtgaggg   120
acaggggagt ggcgccctgc aatatttgca tgtcgctatg tgttctggga aatcaccata   180
aacgtgaaat gtctttggat ttgggaatct tataagttct gtatgagacc acggatccaa   240
aagctt                                                              246

<210> SEQ ID NO 11
<211> LENGTH: 348
<212> TYPE: DNA
<213> ORGANISM: Homo sapiens

<400> SEQUENCE: 11
atggcaggaa gaagcggaga cagcgacgaa gagctcatca gaacagtcag actcatcaag    60
cttctctatc aaagcccacc tcccaatccc gaggggaccc gacaggcccg aaggaataga   120
agaagaaggt ggagagagag acagagacag atccattcga ttagtgaacg gatccttagc   180
acttatctgg gacgatctgc ggagcctgtg cctcttcagc taccaccgct tgagagactt   240
actcttgatt gtaacgagga ttgtggaact tctgggacgc aggggtggg aagccctcaa   300 atattggtgg aatctcctac agtattggag tcaggaacta aagaatag               348

<210> SEQ ID NO 12
<211> LENGTH: 348
<212> TYPE: DNA
<213> ORGANISM: Artificial Sequence
<220> FEATURE:
<223> OTHER INFORMATION: This sequence represents mutant human sequence.

<400> SEQUENCE: 12
atggcaggaa gaagcggaga cagcgacgaa gagctcatca gaacagtcag actcatcaag    60
cttctctatc aaagcccacc tcccaatccc gaggggaccc gacaggcccg aaggaataga   120
agaagaaggt ggcgtgagag acagagacag atccattcga ttagtgaacg gatccttagc   180
acttatctgg gacgatctgc ggagcctgtg cctcttcagc taccaccgct tgagagactt   240
actcttgatt gtaacgagga ttgtggaact tctgggacgc aggggtggg aagccctcaa   300

```
atattggtgg aatctcctac agtattggag tcaggaacta aagaatag                    348
```

<210> SEQ ID NO 13
<211> LENGTH: 19
<212> TYPE: RNA
<213> ORGANISM: Artificial Sequence
<220> FEATURE:
<223> OTHER INFORMATION: This sequence represents a target sequence of
      human CCR5 shRNA (hu13) in human CCR5 mRNA.

<400> SEQUENCE: 13

```
gugucaaguc caaucuaug                                                    19
```

<210> SEQ ID NO 14
<211> LENGTH: 49
<212> TYPE: RNA
<213> ORGANISM: Artificial Sequence
<220> FEATURE:
<223> OTHER INFORMATION: This sequence is human CCR5 shRNA (hu13).

<400> SEQUENCE: 14

```
gugucaaguc caaucuaugu uguccgacca uagauuggac uugacacuu                   49
```

<210> SEQ ID NO 15
<211> LENGTH: 47
<212> TYPE: DNA
<213> ORGANISM: Artificial Sequence
<220> FEATURE:
<223> OTHER INFORMATION: This sequence is human CCR5 shRNA (hu13) in
      plasmid DNA.

<400> SEQUENCE: 15

```
gtgtcaagtc caatctatgt tgtccgacca tagattggac ttgacac                     47
```

<210> SEQ ID NO 16
<211> LENGTH: 20
<212> TYPE: RNA
<213> ORGANISM: Artificial Sequence
<220> FEATURE:
<223> OTHER INFORMATION: This is the human CCR5 shRNA (hu1005) target
      sequence in human CCR5 mRNA.

<400> SEQUENCE: 16

```
gagcaagcuc aguuuacacc                                                   20
```

<210> SEQ ID NO 17
<211> LENGTH: 51
<212> TYPE: RNA
<213> ORGANISM: Artificial Sequence
<220> FEATURE:
<223> OTHER INFORMATION: This is the sequence of human CCR5 shRNA
      (hu1005).

<400> SEQUENCE: 17

```
gagcaagcuc aguuuacacc uuguccgacg guguaaacug agcuugcucu u                51
```

<210> SEQ ID NO 18
<211> LENGTH: 49
<212> TYPE: DNA
<213> ORGANISM: Artificial Sequence
<220> FEATURE:
<223> OTHER INFORMATION: This is the sequence of human CCR5 shRNA
      (hu1005) in plasmid DNA.

<400> SEQUENCE: 18

```
gagcaagctc agtttacacc ttgtccgacg gtgtaaactg agcttgctc                   49
```

```
<210> SEQ ID NO 19
<211> LENGTH: 20
<212> TYPE: RNA
<213> ORGANISM: Artificial Sequence
<220> FEATURE:
<223> OTHER INFORMATION: This is the target sequence of rhesus CCR5
      shRNA (rh1005) in rhesus CCR5 mRNA.

<400> SEQUENCE: 19
gagcaaguuc aguuuacacc                                              20

<210> SEQ ID NO 20
<211> LENGTH: 51
<212> TYPE: RNA
<213> ORGANISM: Artificial Sequence
<220> FEATURE:
<223> OTHER INFORMATION: This is the sequence of rhesus CCR5 shRNA
      (rh1005).

<400> SEQUENCE: 20
gagcaaguuc aguuuacacc uuguccgacg guguaaacug aacuugcucu u           51

<210> SEQ ID NO 21
<211> LENGTH: 49
<212> TYPE: DNA
<213> ORGANISM: Artificial Sequence
<220> FEATURE:
<223> OTHER INFORMATION: This is the sequence of rhesus CCR5 shRNA
      (rh1005) in plasmid DNA.

<400> SEQUENCE: 21
gagcaagttc agtttacacc ttgtccgacg gtgtaaactg aacttgctc              49

<210> SEQ ID NO 22
<211> LENGTH: 25
<212> TYPE: DNA
<213> ORGANISM: Artificial Sequence
<220> FEATURE:
<223> OTHER INFORMATION: This is the sequence of one of the primer pairs
      that can be used to amplify human CCR5 cDNA from
      pBABE.CCR5 plasmid DNA.

<400> SEQUENCE: 22
gatggattat caagtgtcaa gtcca                                        25

<210> SEQ ID NO 23
<211> LENGTH: 23
<212> TYPE: DNA
<213> ORGANISM: Artificial Sequence
<220> FEATURE:
<223> OTHER INFORMATION: This is the sequence of one of the primer pairs
      that can be used to amplify human CCR5 cDNA from
      pBABE.CCR5 plasmid DNA.

<400> SEQUENCE: 23
gtcacaagcc cacagatatt tcc                                          23

<210> SEQ ID NO 24
<211> LENGTH: 45
<212> TYPE: DNA
<213> ORGANISM: Artificial Sequence
<220> FEATURE:
<223> OTHER INFORMATION: This is the sequence of a hairpin adopter 1 DNA
      linker containing a MmeI restriction enzyme site.

<400> SEQUENCE: 24
gtcggacaat tgcgacccgc atgctgcggg tcgcaattgt ccgac                  45
```

```
<210> SEQ ID NO 25
<211> LENGTH: 32
<212> TYPE: DNA
<213> ORGANISM: Artificial Sequence
<220> FEATURE:
<223> OTHER INFORMATION: This is the sequence of the +strand of an
      adopter 2 (Ad2) linker.

<400> SEQUENCE: 25 gggatccct tcggtactcc agaccgtgag tc                                   32

<210> SEQ ID NO 26
<211> LENGTH: 18
<212> TYPE: DNA
<213> ORGANISM: Artificial Sequence
<220> FEATURE:
<223> OTHER INFORMATION: This is the sequence of the -strand of an
      adopter 2 (Ad2) linker. n can be any nucleotide in the position.
<220> FEATURE:
<221> NAME/KEY: misc_feature
<222> LOCATION: 17, 18
<223> OTHER INFORMATION: n = A,T,C or G

<400> SEQUENCE: 26
taccgaaggg atccccnn                                                  18

<210> SEQ ID NO 27
<211> LENGTH: 24
<212> TYPE: DNA
<213> ORGANISM: Artificial Sequence
<220> FEATURE:
<223> OTHER INFORMATION: This is the sequence of a primer that can be
      used to subject Ad2 ligated DNA fragments to a primer extension
      reaction.

<400> SEQUENCE: 27
gactcacggt ctggagtacc gaag                                           24

<210> SEQ ID NO 28
<211> LENGTH: 61
<212> TYPE: DNA
<213> ORGANISM: Artificial Sequence
<220> FEATURE:
<223> OTHER INFORMATION: This is the sequence of a sense strand of a
      hybridized oligoDNA for generation of a rhesus
      CCR4 shRNA expression unit.

<400> SEQUENCE: 28
gatccccgag caagttcagt ttacaccttg tccgacgtgt aaactgaact tgctcttttt    60
c                                                                    61

<210> SEQ ID NO 29
<211> LENGTH: 62
<212> TYPE: DNA
<213> ORGANISM: Artificial Sequence
<220> FEATURE:
<223> OTHER INFORMATION: This is the sequence of an anti-sense strand of
      a hybridized oligoDNA for generation of a rhesus CCR4 shRNA
      expression unit.

<400> SEQUENCE: 29
gggctcgttc aagtcaaatg tggaacaggc tgccacattt gacttgaacg agaaaaagag    60
ct                                                                   62

<210> SEQ ID NO 30
```

```
<211> LENGTH: 23
<212> TYPE: DNA
<213> ORGANISM: Artificial Sequence
<220> FEATURE:
<223> OTHER INFORMATION: This is the sequence of the + strand of an
      oligo DNA linker.

<400> SEQUENCE: 30 cgataccctag ggacggctga cgc                                            23

<210> SEQ ID NO 31
<211> LENGTH: 19
<212> TYPE: DNA
<213> ORGANISM: Artificial Sequence
<220> FEATURE:
<223> OTHER INFORMATION: This is the sequence of the - strand of an
      oligo DNA linker.

<400> SEQUENCE: 31
gtcgaccgtc ctagggtat                                                  19

<210> SEQ ID NO 32
<211> LENGTH: 20
<212> TYPE: DNA
<213> ORGANISM: Artificial Sequence
<220> FEATURE:
<223> OTHER INFORMATION: This is the sequence of the sense portion of an
      oligonucletoide probe used for Northern blot
      analysis of siRNA.

<400> SEQUENCE: 32
gagcaagttc agtttacacc                                                 20

<210> SEQ ID NO 33
<211> LENGTH: 20
<212> TYPE: DNA
<213> ORGANISM: Artificial Sequence
<220> FEATURE:
<223> OTHER INFORMATION: This is the sequence of the anti-sense portion
      of an oligonucletoide probe used for Northern blot analysis of
      siRNA.

<400> SEQUENCE: 33 ggtgtaaaact gaacttgctc                                                20

<210> SEQ ID NO 34
<211> LENGTH: 20
<212> TYPE: RNA
<213> ORGANISM: Artificial Sequence
<220> FEATURE:
<223> OTHER INFORMATION: This is the sequence of a synthetic rhCCR5
      siRNA from Sigma-Proligo.

<400> SEQUENCE: 34
gguguaaacu gaacuugcuc                                                 20

<210> SEQ ID NO 35
<211> LENGTH: 52
<212> TYPE: DNA
<213> ORGANISM: Artificial Sequence
<220> FEATURE:
<223> OTHER INFORMATION: This is the sequence of an RT stem loop primer
      used to quantitate the levels of the antisense
      strand of siRNA against rhesus CCR5.

<400> SEQUENCE: 35
gtcgtatcca gtgcagggtc cgaggtattc gcactggata cgacaagagc aa             52
```

```
<210> SEQ ID NO 36
<211> LENGTH: 18
<212> TYPE: DNA
<213> ORGANISM: Artificial Sequence
<220> FEATURE:
<223> OTHER INFORMATION: This is the sequence of a forward primer used
      in a real time stem-llop RT-PCR method used to quantitate the
      levels of the antisense strand of siRNA against rhesus CCR5.

<400> SEQUENCE: 36
gcgcggtgta aactgaac                                                    18

<210> SEQ ID NO 37
<211> LENGTH: 16
<212> TYPE: DNA
<213> ORGANISM: Artificial Sequence
<220> FEATURE:
<223> OTHER INFORMATION: This is the sequence of a reverse primer used
      in a real time stem-llop RT-PCR method used to quantitate the
      levels of the antisense strand of siRNA against rhesus CCR5.

<400> SEQUENCE: 37
gtgcagggtc cgaggt                                                      16

<210> SEQ ID NO 38
<211> LENGTH: 23
<212> TYPE: DNA
<213> ORGANISM: Artificial Sequence
<220> FEATURE:
<223> OTHER INFORMATION: This is the sequence of a probe used in a real
      time stem-llop RT-PCR method used to quantitate
      the levels of the antisense strand of siRNA
      against rhesus CCR5.

<400> SEQUENCE: 38
amtggatacg acaagagcaa mgb                                              23

<210> SEQ ID NO 39
<211> LENGTH: 20
<212> TYPE: RNA
<213> ORGANISM: Artificial Sequence
<220> FEATURE:
<223> OTHER INFORMATION: This is the sequence of a serial diluted
      synthetic 22nt antisense strand of siRNA against rhCCR5.

<400> SEQUENCE: 39
gguguaaacu gaacuugcuc                                                  20
```